US008795298B2

(12) United States Patent  
Hernlund et al.

(10) Patent No.: US 8,795,298 B2  
(45) Date of Patent: Aug. 5, 2014

(54) TETHER TENSIONING DEVICES AND RELATED METHODS

(75) Inventors: Jonathan D. Hernlund, Santa Clara, CA (US); Tenny C. Calhoun, Sunnyvale, CA (US); Brian Tang, Fremont, CA (US); John To, Newark, CA (US); Clyde Henry Booth, III, San Francisco, CA (US)

(73) Assignee: Guided Delivery Systems Inc., Santa Clara, CA (US)

( * ) Notice: Subject to any disclaimer, the term of this patent is extended or adjusted under 35 U.S.C. 154(b) by 683 days.

(21) Appl. No.: 12/576,955

(22) Filed: Oct. 9, 2009

(65) Prior Publication Data

US 2010/0094314 A1   Apr. 15, 2010

Related U.S. Application Data

(60) Provisional application No. 61/104,681, filed on Oct. 10, 2008, provisional application No. 61/104,686, filed on Oct. 10, 2008.

(51) Int. Cl.
 *A61B 17/10* (2006.01)

(52) U.S. Cl.
 USPC .......................................... 606/148; 606/139

(58) Field of Classification Search
 CPC .............................................. A61B 2017/0496
 USPC .................. 606/103, 139, 144, 146, 148; 242/378.1–378.3
 See application file for complete search history.

(56) References Cited

U.S. PATENT DOCUMENTS 2,618,137 A * 11/1952 White .......................... 464/40
3,537,666 A    11/1970 Lewis
3,656,185 A    4/1972  Carpentier
3,727,614 A    4/1973  Kniazuk
3,773,034 A    11/1973 Burns et al.
3,961,419 A    6/1976  Schwartz
3,976,079 A    8/1976  Samuels et al.
4,014,492 A    3/1977  Rothfuss
4,034,473 A    7/1977  May
4,042,979 A    8/1977  Angell (Continued)

FOREIGN PATENT DOCUMENTS

EP       0 669 101 A1    8/1995
WO    WO-94/03227 A1    2/1994

(Continued)

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.

(Continued)

*Primary Examiner* — Gregory Anderson  
(74) *Attorney, Agent, or Firm* — Morrison & Foerster LLP

(57) ABSTRACT

Devices, methods, and kits for tensioning tethers during a tissue modification procedure are described. In some variations, a tether coupled to anchors embedded in tissue may be tensioned to provide a cinching effect that tightens or compresses the tissue by bringing two pieces or sections of the tissue together. In certain variations, the tether may then be locked (e.g., to maintain the tension), and/or excess tether may be severed. The devices, methods, and/or kits may be used, for example, in minimally invasive procedures.

30 Claims, 38 Drawing Sheets

(56) References Cited

U.S. PATENT DOCUMENTS

| | | | |
|---|---|---|---|
| 4,043,504 | A | 8/1977 | Hueil et al. |
| 4,053,979 | A | 10/1977 | Tuthill et al. |
| 4,055,861 | A | 11/1977 | Carpentier et al. |
| 4,069,825 | A | 1/1978 | Akiyama |
| 4,290,151 | A | 9/1981 | Massana |
| 4,373,923 | A * | 2/1983 | Kilwin .......................... 464/36 |
| 4,384,406 | A | 5/1983 | Tischlinger |
| 4,445,892 | A | 5/1984 | Hussein et al. |
| 4,489,446 | A | 12/1984 | Reed |
| 4,494,542 | A | 1/1985 | Lee |
| 4,510,934 | A | 4/1985 | Batra |
| 4,549,545 | A | 10/1985 | Levy |
| 4,619,247 | A | 10/1986 | Inoue et al. |
| 4,700,250 | A | 10/1987 | Kuriyama |
| 4,705,040 | A | 11/1987 | Mueller et al. |
| 4,726,371 | A | 2/1988 | Gibbens |
| 4,750,492 | A | 6/1988 | Jacobs |
| 4,758,221 | A | 7/1988 | Jureidini |
| 4,784,133 | A | 11/1988 | Mackin |
| 4,845,851 | A | 7/1989 | Warthen |
| 4,848,341 | A | 7/1989 | Ahmad |
| 4,850,354 | A | 7/1989 | McGurk-Burleson et al. |
| 4,961,738 | A | 10/1990 | Mackin |
| 4,969,893 | A | 11/1990 | Swor |
| 4,976,710 | A | 12/1990 | Mackin |
| 5,035,701 | A | 7/1991 | Kabbara |
| 5,053,047 | A | 10/1991 | Yoon |
| 5,064,431 | A | 11/1991 | Gilbertson et al. |
| 5,078,731 | A | 1/1992 | Hayhurst |
| 5,084,058 | A | 1/1992 | Li |
| 5,087,263 | A | 2/1992 | Li |
| 5,103,804 | A | 4/1992 | Abele et al. |
| 5,133,723 | A | 7/1992 | Li et al. |
| RE34,021 | E | 8/1992 | Mueller et al. |
| 5,221,255 | A | 6/1993 | Mahurkar et al. |
| 5,242,456 | A | 9/1993 | Nash et al. |
| 5,242,457 | A | 9/1993 | Akopov et al. |
| 5,242,459 | A | 9/1993 | Buelna |
| 5,257,975 | A | 11/1993 | Foshee |
| 5,282,832 | A | 2/1994 | Toso et al. |
| 5,312,341 | A | 5/1994 | Turi |
| 5,312,423 | A | 5/1994 | Rosenbluth et al. |
| 5,324,298 | A | 6/1994 | Phillips et al. |
| 5,346,500 | A | 9/1994 | Suchart |
| 5,350,133 | A | 9/1994 | Morimoto |
| 5,358,479 | A | 10/1994 | Wilson |
| 5,358,514 | A | 10/1994 | Schulman et al. |
| 5,364,407 | A | 11/1994 | Poll |
| 5,366,479 | A | 11/1994 | McGarry et al. |
| 5,368,591 | A | 11/1994 | Lennox et al. |
| 5,383,905 | A | 1/1995 | Golds et al. |
| 5,409,483 | A | 4/1995 | Campbell et al. |
| 5,409,499 | A | 4/1995 | Yi |
| 5,417,700 | A | 5/1995 | Egan |
| 5,423,837 | A | 6/1995 | Mericle et al. |
| 5,431,659 | A | 7/1995 | Ross, Jr. et al. |
| 5,437,680 | A | 8/1995 | Yoon |
| 5,439,470 | A | 8/1995 | Li |
| 5,450,860 | A | 9/1995 | O'Connor |
| 5,452,513 | A | 9/1995 | Zinnbauer et al. |
| 5,474,572 | A | 12/1995 | Hayhurst |
| 5,520,702 | A | 5/1996 | Sauer et al. |
| 5,522,873 | A | 6/1996 | Jackman et al. |
| 5,524,630 | A | 6/1996 | Crowley |
| 5,527,323 | A | 6/1996 | Jervis et al. |
| 5,531,686 | A | 7/1996 | Lundquist et al. |
| 5,531,763 | A | 7/1996 | Mastri et al. |
| 5,545,134 | A | 8/1996 | Hilaire et al. |
| 5,545,168 | A | 8/1996 | Burke |
| 5,565,122 | A | 10/1996 | Zinnbauer et al. |
| 5,571,215 | A | 11/1996 | Sterman et al. |
| 5,584,835 | A | 12/1996 | Greenfield |
| 5,591,194 | A | 1/1997 | Berthiaume |
| 5,626,590 | A | 5/1997 | Wilk |
| 5,626,614 | A | 5/1997 | Hart |
| 5,630,824 | A | 5/1997 | Hart |
| 5,643,289 | A | 7/1997 | Sauer et al. |
| 5,665,109 | A | 9/1997 | Yoon |
| 5,669,917 | A | 9/1997 | Sauer et al. |
| 5,674,279 | A | 10/1997 | Wright et al. |
| 5,690,655 | A | 11/1997 | Hart et al. |
| 5,702,397 | A | 12/1997 | Goble et al. |
| 5,709,695 | A | 1/1998 | Northrup, III |
| 5,716,370 | A | 2/1998 | Williamson, IV et al. |
| 5,718,725 | A | 2/1998 | Sterman et al. |
| 5,725,542 | A | 3/1998 | Yoon |
| 5,733,308 | A | 3/1998 | Daugherty et al. |
| 5,735,290 | A | 4/1998 | Sterman et al. |
| 5,741,260 | A | 4/1998 | Songer et al. |
| 5,741,301 | A | 4/1998 | Pagedas |
| 5,752,518 | A | 5/1998 | McGee et al. |
| 5,752,964 | A | 5/1998 | Mericle |
| 5,752,966 | A | 5/1998 | Chang |
| 5,755,730 | A | 5/1998 | Swain et al. |
| 5,766,240 | A | 6/1998 | Johnson |
| 5,769,812 | A | 6/1998 | Stevens et al. |
| 5,810,848 | A | 9/1998 | Hayhurst |
| 5,810,853 | A | 9/1998 | Yoon |
| 5,817,107 | A | 10/1998 | Schaller |
| 5,827,171 | A | 10/1998 | Dobak, III et al. |
| 5,843,169 | A | 12/1998 | Taheri |
| 5,848,969 | A | 12/1998 | Panescu et al. |
| 5,860,992 | A | 1/1999 | Daniel et al. |
| 5,860,993 | A | 1/1999 | Thompson et al. |
| 5,861,003 | A | 1/1999 | Latson et al. |
| 5,868,733 | A | 2/1999 | Ockuly et al. |
| 5,879,371 | A | 3/1999 | Gardiner et al. |
| 5,885,238 | A | 3/1999 | Stevens et al. |
| 5,888,240 | A | 3/1999 | Carpentier et al. |
| 5,902,321 | A | 5/1999 | Caspari et al. |
| 5,904,651 | A | 5/1999 | Swanson et al. |
| 5,919,208 | A | 7/1999 | Valenti |
| 5,935,149 | A | 8/1999 | Ek |
| 5,947,983 | A | 9/1999 | Solar et al. |
| 5,961,440 | A | 10/1999 | Schweich, Jr. et al. |
| 5,961,539 | A | 10/1999 | Northrup, III et al. |
| 5,972,004 | A | 10/1999 | Williamson, IV et al. |
| 5,989,284 | A | 11/1999 | Laufer |
| 5,991,650 | A | 11/1999 | Swanson et al. |
| 6,010,531 | A | 1/2000 | Donlon et al. |
| 6,015,428 | A | 1/2000 | Pagedas |
| 6,045,497 | A | 4/2000 | Schweich, Jr. et al. |
| 6,050,936 | A | 4/2000 | Schweich, Jr. et al. |
| 6,059,715 | A | 5/2000 | Schweich, Jr. et al. |
| 6,066,160 | A | 5/2000 | Colvin et al. |
| 6,074,401 | A | 6/2000 | Gardiner et al. |
| 6,077,989 | A | 6/2000 | Kandel et al. |
| 6,080,182 | A | 6/2000 | Shaw et al. |
| 6,086,608 | A | 7/2000 | Ek et al. |
| 6,099,553 | A | 8/2000 | Hart et al. |
| 6,125,852 | A | 10/2000 | Stevens et al. |
| 6,149,658 | A | 11/2000 | Gardiner et al. |
| 6,152,934 | A | 11/2000 | Harper et al. |
| 6,162,168 | A | 12/2000 | Schweich, Jr. et al. |
| 6,165,183 | A | 12/2000 | Kuehn et al. |
| 6,171,317 | B1 | 1/2001 | Jackson et al. |
| 6,197,017 | B1 | 3/2001 | Brock et al. |
| 6,200,329 | B1 | 3/2001 | Fung et al. |
| 6,221,084 | B1 | 4/2001 | Fleenor |
| 6,228,096 | B1 | 5/2001 | Marchand |
| 6,250,308 | B1 | 6/2001 | Cox |
| 6,254,620 | B1 | 7/2001 | Koh et al. |
| 6,258,118 | B1 | 7/2001 | Baum et al. |
| 6,260,552 | B1 | 7/2001 | Mortier et al. |
| 6,269,819 | B1 | 8/2001 | Oz et al. |
| 6,283,993 | B1 | 9/2001 | Cosgrove et al. |
| 6,306,149 | B1 | 10/2001 | Meade |
| 6,312,447 | B1 | 11/2001 | Grimes |
| 6,328,727 | B1 | 12/2001 | Frazier et al. |
| 6,332,893 | B1 | 12/2001 | Mortier et al. |
| 6,355,030 | B1 | 3/2002 | Aldrich et al. |
| 6,378,289 | B1 | 4/2002 | Trudeau et al. |
| 6,406,420 | B1 | 6/2002 | McCarthy et al. |
| 6,409,743 | B1 | 6/2002 | Fenton, Jr. |

(56) References Cited

U.S. PATENT DOCUMENTS

| | | | |
|---|---|---|---|
| 6,423,088 B1 | 7/2002 | Fenton, Jr. | |
| 6,432,123 B2 | 8/2002 | Schwartz et al. | |
| 6,461,327 B1 | 10/2002 | Addis et al. | |
| 6,471,715 B1 * | 10/2002 | Weiss | 606/216 |
| 6,506,190 B1 | 1/2003 | Walshe | |
| 6,514,265 B2 | 2/2003 | Ho et al. | |
| 6,524,328 B2 | 2/2003 | Levinson | |
| 6,524,338 B1 | 2/2003 | Gundry | |
| 6,533,753 B1 | 3/2003 | Haarstad et al. | |
| 6,551,332 B1 | 4/2003 | Nguyen et al. | |
| 6,575,971 B2 | 6/2003 | Hauck et al. | |
| 6,575,987 B2 | 6/2003 | Gellman et al. | |
| 6,589,160 B2 | 7/2003 | Schweich, Jr. et al. | |
| 6,602,288 B1 | 8/2003 | Cosgrove et al. | |
| 6,602,289 B1 | 8/2003 | Colvin et al. | |
| 6,607,541 B1 | 8/2003 | Gardiner et al. | |
| 6,613,059 B2 | 9/2003 | Schaller et al. | |
| 6,616,667 B1 | 9/2003 | Steiger et al. | |
| 6,619,291 B2 | 9/2003 | Hlavka et al. | |
| 6,626,899 B2 | 9/2003 | Houser et al. | |
| 6,629,534 B1 | 10/2003 | St. Goar et al. | |
| 6,641,593 B1 | 11/2003 | Schaller et al. | |
| 6,648,903 B1 | 11/2003 | Pierson, III | |
| 6,651,671 B1 | 11/2003 | Donlon et al. | |
| 6,652,562 B2 | 11/2003 | Collier et al. | |
| 6,655,386 B1 | 12/2003 | Makower et al. | |
| 6,669,687 B1 | 12/2003 | Saadat | |
| 6,676,702 B2 | 1/2004 | Mathis | |
| 6,689,164 B1 | 2/2004 | Seguin | |
| 6,699,263 B2 | 3/2004 | Cope | |
| 6,702,826 B2 | 3/2004 | Liddicoat et al. | |
| 6,716,243 B1 | 4/2004 | Colvin et al. | |
| 6,718,985 B2 | 4/2004 | Hlavka et al. | |
| 6,723,038 B1 | 4/2004 | Schroeder et al. | |
| 6,723,107 B1 | 4/2004 | Skiba et al. | |
| 6,733,509 B2 | 5/2004 | Nobles et al. | |
| 6,752,813 B2 | 6/2004 | Goldfarb et al. | |
| 6,790,231 B2 | 9/2004 | Liddicoat et al. | |
| 6,793,618 B2 | 9/2004 | Schweich, Jr. et al. | |
| 6,908,424 B2 | 6/2005 | Mortier et al. | |
| 6,923,818 B2 | 8/2005 | Muramatsu et al. | |
| 6,932,792 B1 | 8/2005 | St. Goar et al. | |
| 6,986,775 B2 | 1/2006 | Morales et al. | |
| 6,991,643 B2 | 1/2006 | Saadat | |
| 6,997,931 B2 | 2/2006 | Sauer et al. | |
| 7,004,958 B2 | 2/2006 | Adams et al. | |
| 7,037,334 B1 | 5/2006 | Hlavka et al. | |
| 7,044,957 B2 | 5/2006 | Foerster et al. | |
| 7,048,754 B2 | 5/2006 | Martin et al. | |
| 7,094,246 B2 | 8/2006 | Anderson et al. | |
| 7,101,395 B2 | 9/2006 | Tremulis et al. | |
| 7,125,421 B2 | 10/2006 | Tremulis et al. | |
| 7,166,127 B2 | 1/2007 | Spence et al. | |
| 7,186,262 B2 | 3/2007 | Saadat | |
| 7,189,199 B2 | 3/2007 | McCarthy et al. | |
| 7,235,086 B2 | 6/2007 | Sauer et al. | |
| 7,241,310 B2 | 7/2007 | Taylor et al. | |
| 7,326,231 B2 | 2/2008 | Phillips et al. | |
| 7,374,530 B2 | 5/2008 | Schaller | |
| 7,381,210 B2 | 6/2008 | Zarbatany et al. | |
| 7,390,329 B2 | 6/2008 | Westra et al. | |
| 7,452,325 B2 | 11/2008 | Schaller | |
| 7,588,582 B2 | 9/2009 | Starksen et al. | |
| 7,618,449 B2 | 11/2009 | Tremulis et al. | |
| 7,666,193 B2 | 2/2010 | Starksen et al. | |
| 7,699,892 B2 | 4/2010 | Rafiee et al. | |
| 7,727,247 B2 | 6/2010 | Kimura et al. | |
| 7,815,659 B2 * | 10/2010 | Conlon et al. | 606/198 |
| 7,883,538 B2 | 2/2011 | To et al. | |
| 7,993,368 B2 | 8/2011 | Gambale et al. | |
| 2001/0005787 A1 | 6/2001 | Oz et al. | |
| 2001/0014800 A1 | 8/2001 | Frazier et al. | |
| 2001/0023332 A1 | 9/2001 | Hahnen | |
| 2001/0031979 A1 | 10/2001 | Ricci | |
| 2001/0041821 A1 | 11/2001 | Wilk | |
| 2002/0013621 A1 | 1/2002 | Stobie et al. | |
| 2002/0029080 A1 | 3/2002 | Mortier et al. | |
| 2002/0035361 A1 | 3/2002 | Houser et al. | |
| 2002/0042621 A1 | 4/2002 | Liddicoat et al. | |
| 2002/0065536 A1 | 5/2002 | Hart et al. | |
| 2002/0072757 A1 | 6/2002 | Ahmed et al. | |
| 2002/0077524 A1 | 6/2002 | Schweich, Jr. et al. | |
| 2002/0087048 A1 | 7/2002 | Brock et al. | |
| 2002/0087049 A1 | 7/2002 | Brock et al. | |
| 2002/0087148 A1 | 7/2002 | Brock et al. | |
| 2002/0087169 A1 | 7/2002 | Brock et al. | |
| 2002/0095167 A1 | 7/2002 | Liddicoat et al. | |
| 2002/0095175 A1 | 7/2002 | Brock et al. | |
| 2002/0095180 A1 | 7/2002 | West, Jr. et al. | |
| 2002/0116012 A1 | 8/2002 | May et al. | |
| 2002/0138044 A1 | 9/2002 | Streeter et al. | |
| 2002/0156526 A1 | 10/2002 | Hlavka et al. | |
| 2002/0161378 A1 | 10/2002 | Downing | |
| 2002/0165486 A1 | 11/2002 | Bertolero et al. | |
| 2002/0173841 A1 | 11/2002 | Ortiz et al. | |
| 2002/0183835 A1 | 12/2002 | Taylor et al. | |
| 2002/0193815 A1 | 12/2002 | Foerster et al. | |
| 2003/0009196 A1 | 1/2003 | Peterson | |
| 2003/0018358 A1 | 1/2003 | Saadat | |
| 2003/0032979 A1 | 2/2003 | Mortier et al. | |
| 2003/0033006 A1 | 2/2003 | Phillips et al. | |
| 2003/0060813 A1 | 3/2003 | Loeb et al. | |
| 2003/0069593 A1 | 4/2003 | Tremulis et al. | |
| 2003/0074012 A1 | 4/2003 | Nguyen et al. | |
| 2003/0078465 A1 | 4/2003 | Pai et al. | |
| 2003/0078603 A1 | 4/2003 | Schaller et al. | |
| 2003/0093118 A1 | 5/2003 | Ho et al. | |
| 2003/0105520 A1 | 6/2003 | Alferness et al. | |
| 2003/0125739 A1 | 7/2003 | Bagga et al. | |
| 2003/0125767 A1 | 7/2003 | Collier et al. | |
| 2003/0130731 A1 | 7/2003 | Vidlund et al. | |
| 2003/0144673 A1 | 7/2003 | Onuki et al. | |
| 2003/0144697 A1 | 7/2003 | Mathis et al. | |
| 2003/0158464 A1 | 8/2003 | Bertolero | |
| 2003/0158581 A1 | 8/2003 | Levinson | |
| 2003/0167062 A1 | 9/2003 | Gambale et al. | |
| 2003/0167071 A1 | 9/2003 | Martin et al. | |
| 2003/0181800 A1 | 9/2003 | Bonutti | |
| 2003/0191497 A1 | 10/2003 | Cope | |
| 2003/0195562 A1 | 10/2003 | Collier et al. | |
| 2003/0199974 A1 | 10/2003 | Lee et al. | |
| 2003/0204205 A1 | 10/2003 | Sauer et al. | |
| 2003/0220659 A1 | 11/2003 | Schmieding et al. | |
| 2003/0220685 A1 | 11/2003 | Hlavka et al. | |
| 2003/0225420 A1 | 12/2003 | Wardle | |
| 2003/0229361 A1 | 12/2003 | Jackson | |
| 2003/0233105 A1 | 12/2003 | Gayton | |
| 2003/0233142 A1 | 12/2003 | Morales et al. | |
| 2003/0236535 A1 | 12/2003 | Onuki et al. | |
| 2004/0003819 A1 | 1/2004 | St. Goar et al. | |
| 2004/0019378 A1 | 1/2004 | Hlavka et al. | |
| 2004/0030382 A1 | 2/2004 | St. Goar et al. | |
| 2004/0039442 A1 | 2/2004 | St. Goar et al. | |
| 2004/0044365 A1 | 3/2004 | Bachman | |
| 2004/0092962 A1 | 5/2004 | Thornton et al. | |
| 2004/0093023 A1 | 5/2004 | Allen et al. | |
| 2004/0097788 A1 | 5/2004 | Mourlas et al. | |
| 2004/0122450 A1 | 6/2004 | Oren et al. | |
| 2004/0133274 A1 | 7/2004 | Webler et al. | |
| 2004/0148020 A1 | 7/2004 | Vidlund et al. | |
| 2004/0152947 A1 | 8/2004 | Schroeder et al. | |
| 2004/0162465 A1 | 8/2004 | Carrillo | |
| 2004/0172046 A1 | 9/2004 | Hlavka et al. | |
| 2004/0181238 A1 | 9/2004 | Zarbatany et al. | |
| 2004/0193191 A1 | 9/2004 | Starksen et al. | |
| 2004/0204724 A1 | 10/2004 | Kissel et al. | |
| 2004/0210238 A1 | 10/2004 | Nobles et al. | |
| 2004/0225300 A1 | 11/2004 | Goldfarb et al. | |
| 2004/0236354 A1 | 11/2004 | Seguin | |
| 2004/0236372 A1 | 11/2004 | Anspach, III et al. | |
| 2004/0236419 A1 | 11/2004 | Milo | |
| 2004/0243227 A1 | 12/2004 | Starksen et al. | |
| 2005/0033325 A1 | 2/2005 | May et al. | |
| 2005/0055052 A1 | 3/2005 | Lombardo et al. | |

(56) References Cited

U.S. PATENT DOCUMENTS

| | | |
|---|---|---|
| 2005/0055087 A1 | 3/2005 | Starksen |
| 2005/0065550 A1 | 3/2005 | Starksen et al. |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0119735 A1 | 6/2005 | Spence et al. |
| 2005/0125011 A1 | 6/2005 | Spence et al. |
| 2005/0137639 A1 | 6/2005 | Havel |
| 2005/0143762 A1 | 6/2005 | Paraschac et al. |
| 2005/0165424 A1 | 7/2005 | Gallagher et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0106422 A1 | 5/2006 | Del Rio et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0200199 A1 | 9/2006 | Bonutti et al. |
| 2006/0207606 A1 | 9/2006 | Roue et al. |
| 2006/0235413 A1 | 10/2006 | Denham et al. |
| 2006/0241656 A1 | 10/2006 | Starksen et al. |
| 2006/0264975 A1 | 11/2006 | Pipenhagen et al. |
| 2006/0265010 A1 | 11/2006 | Paraschac et al. |
| 2006/0271060 A1* | 11/2006 | Gordon ............... 606/103 |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010852 A1 | 1/2007 | Blaeser et al. |
| 2007/0010857 A1 | 1/2007 | Sugimoto et al. |
| 2007/0016250 A1 | 1/2007 | Blaeser et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0066994 A1 | 3/2007 | Blaeser et al. |
| 2007/0106310 A1 | 5/2007 | Goldin et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2007/0112425 A1 | 5/2007 | Schaller et al. |
| 2007/0156172 A1 | 7/2007 | Alvarado |
| 2007/0213746 A1 | 9/2007 | Hahn et al. |
| 2007/0276437 A1 | 11/2007 | Call et al. |
| 2008/0004622 A1 | 1/2008 | Coe et al. |
| 2008/0033460 A1* | 2/2008 | Ziniti et al. ............... 606/148 |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058868 A1 | 3/2008 | To et al. |
| 2008/0065156 A1 | 3/2008 | Hauser et al. |
| 2008/0097484 A1 | 4/2008 | Lim et al. |
| 2008/0172035 A1 | 7/2008 | Starksen et al. |
| 2008/0177304 A1 | 7/2008 | Westra et al. |
| 2008/0177380 A1 | 7/2008 | Starksen et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0234701 A1 | 9/2008 | Morales et al. |
| 2008/0234702 A1 | 9/2008 | Morales et al. |
| 2008/0234728 A1 | 9/2008 | Starksen et al. |
| 2008/0234815 A1 | 9/2008 | Starksen |
| 2008/0294177 A1 | 11/2008 | To et al. |
| 2009/0182417 A1 | 7/2009 | Tremulis et al. |
| 2009/0204125 A1 | 8/2009 | Onishi et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2009/0292353 A1 | 11/2009 | Yoganathan et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0121349 A1 | 5/2010 | Meier et al. |

FOREIGN PATENT DOCUMENTS

| | | |
|---|---|---|
| WO | WO-95/15715 A1 | 6/1995 |
| WO | WO-96/08208 A1 | 3/1996 |
| WO | WO-96/39942 A1 | 12/1996 |
| WO | WO-97/27799 A1 | 8/1997 |
| WO | WO-97/27807 A1 | 8/1997 |
| WO | WO-97/30639 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/051329 A1 | 7/2002 |
| WO | WO-02/074178 A2 | 9/2002 |
| WO | WO-02/074178 A3 | 9/2002 |
| WO | WO-02/085251 A1 | 10/2002 |
| WO | WO-02/085252 A1 | 10/2002 |
| WO | WO-03/049648 A2 | 6/2003 |
| WO | WO-03/049648 A3 | 6/2003 |
| WO | WO-03/073913 A2 | 9/2003 |
| WO | WO-03/073913 A3 | 9/2003 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/045367 A2 | 6/2004 |
| WO | WO-2004/045367 A3 | 6/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/025644 A3 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2005/110241 A1 | 11/2005 |
| WO | WO-2006/037073 A2 | 4/2006 |
| WO | WO-2006/037073 A3 | 4/2006 |
| WO | WO-2006/039296 A2 | 4/2006 |

(56) References Cited

FOREIGN PATENT DOCUMENTS

| WO | WO-2006/039296 A3 | 4/2006 |
|---|---|---|
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2006/128092 A2 | 11/2006 |
| WO | WO-2006/128092 A3 | 11/2006 |
| WO | WO-2007/001936 A2 | 1/2007 |
| WO | WO-2007/001936 A3 | 1/2007 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2007/100409 A3 | 9/2007 |
| WO | WO-2008/028135 A2 | 3/2008 |
| WO | WO-2008/028135 A3 | 3/2008 |
| WO | WO-2008/112740 A2 | 9/2008 |
| WO | WO-2008/112740 A3 | 9/2008 |
| WO | WO-2009/061611 A1 | 5/2009 |

OTHER PUBLICATIONS

De Simone, R. et al. (Apr. 1, 1994). "Adjustable Annuloplasty for Tricuspid Insufficiency with External Control," *Reader's Comments and Reply, Am. J. Cardiol.* 73(9):721-722.
Downing, S.W. et al. (2002). "Feasibility of Off-Pump ASD Closure Using Real-Time 3-D Echocardiography," *The Heart Surgery Forum* 5(2):96-99, Abstract 7025.
European Examination Communication mailed on Dec. 8, 2009, for EP Application No. 06 837 222.6 filed on Nov. 8, 2006, three pages.
Final Office Action mailed on Aug. 30, 2007, for U.S. Appl. No. 11/232,190, filed Sep. 20, 2005, 9 pages.
Final Office Action mailed on May 28, 2008, for U.S. Appl. No. 11/270,034, filed Nov. 8, 2005, 10 pages.
Final Office Action mailed on Aug. 1, 2008, for U.S. Appl. No. 11/232,190, filed Sep. 20, 2005, 8 pages.
Final Office Action mailed on Jul. 21, 2009, for U.S. Appl. No. 11/270,034, filed Nov. 8, 2005, 8 pages.
Final Office Action mailed on Sep. 2, 2009, for U.S. Appl. No. 11/232,190, filed Sep. 20, 2005, 8 pages.
International Search Report mailed on Jan. 12, 2010, for PCT Patent Application No. PCT/US09/60227, filed on Oct. 9, 2009, 4 pages.
Nagy, Z.L. et al. (Dec. 2000). "Mitral Annuloplasty with a Suture Technique," *European Journal of Cardio-thoracic Surgery* 18(6):739-740.
Non-Final Office Action mailed on Dec. 27, 2006, for U.S. Appl. No. 11/270,034, filed Nov. 8, 2005, 8 pages.
Non-Final Office Action mailed on Mar. 12, 2007, for U.S. Appl. No. 11/232,190, filed Sep. 20, 2005, 11 pages.
Non-Final Office Action mailed on Aug. 30, 2007, for U.S. Appl. No. 11/270,034, filed Nov. 8, 2005, 10 pages.
Non-Final Office Action mailed Jan. 9, 2008, for U.S. Appl. No. 11/232,190, filed Sep. 20, 2005, 8 pages.
Non-Final Office Action mailed on Jan. 23, 2009, for U.S. Appl. No. 11/270,034, filed Nov. 8, 2005, 8 pages.
Non-Final Office Action mailed on Jan. 23, 2009, for U.S. Appl. No. 11/232,190, filed Sep. 20, 2005, 8 pages.
Non-Final Office Action mailed on Jan. 19, 2010, for U.S. Appl. No. 11/270,034, filed Nov. 8, 2005, 10 pages.
Shumway, S.J. et al. (Dec. 1988). "A 'Designer' Annuloplasty Ring for Patients with Massive Mitral Annular Dilatation," *Ann. Thorac. Surg.* 46(6):695-696.
U.S. Appl. No. 12/581,040, filed Oct. 16, 2009, by Starksen et al.
U.S. Appl. No. 12/480,568, filed Jun. 8, 2009, by Serina et al.
U.S. Appl. No. 12/577,044, filed Oct. 9, 2009, by Meier et al.
Final Office Action mailed on Jul. 26, 2010, for U.S. Appl. No. 11/270,034, filed Nov. 8, 2005, 8 pages.
Final Office Action mailed on Sep. 15, 2010, for U.S. Appl. No. 11/894,401, filed Aug. 20, 2007, 6 pages.
Final Office Action mailed on Jun. 11, 2012, for U.S. Appl. No. 12/187,331, filed Aug. 6, 2008, 7 pages.
Non-Final Office Action mailed on Feb. 18, 2010, for U.S. Appl. No. 11/894,401, filed Aug. 20, 2007, 6 pages.
Non-Final Office Action mailed on Oct. 29, 2010, for U.S. Appl. No. 11/894,530, filed Aug. 20, 2007, 11 pages.
Non-Final Office Action mailed on Feb. 11, 2011, for U.S. Appl. No. 12/132,328, filed Jun. 3, 2008, 9 pages.
Non-Final Office Action mailed on Oct. 13, 2011, for U.S. Appl. No. 12/187,331, filed Aug. 6, 2008, 5 pages.
Non-Final Office Action mailed on Dec. 22, 2011, for U.S. Appl. No. 11/270,034, filed Nov. 8, 2005, 8 pages.
Non-Final Office Action mailed on Jan. 27, 2012, for U.S. Appl. No. 12/480,568, filed Jun. 8, 2009, 5 pages.
Notice of Allowance mailed on Nov. 17, 2010, for U.S. Appl. No. 11/232,190, filed Sep. 20, 2005, 11 pages.
Notice of Allowance mailed on Jul. 26, 2011, for U.S. Appl. No. 11/894,530, filed Aug. 20, 2007, 10 pages.
Notice of Allowance mailed on Jun. 8, 2012, for U.S. Appl. No. 11/894,401, filed Aug. 20, 2007, 9 pages.
Australian First Examination Report mailed Mar. 4, 2013, for Australian Patent Application No. 2008311822 filed on Apr. 17, 2010, 4 pages.
Final Office Action mailed on Jan. 22, 2013, for U.S. Appl. No. 12/480,568, filed Jun. 8, 2009, 6 pages.
Final Office Action mailed on Mar. 20, 2013, for U.S. Appl. No. 12/577,044, filed Oct. 9, 2009, 7 pages.
Non-Final Office Action mailed on Jun. 28, 2012, for U.S. Appl. No. 12/577,044, filed Oct. 9, 2009, 7 pages.

* cited by examiner

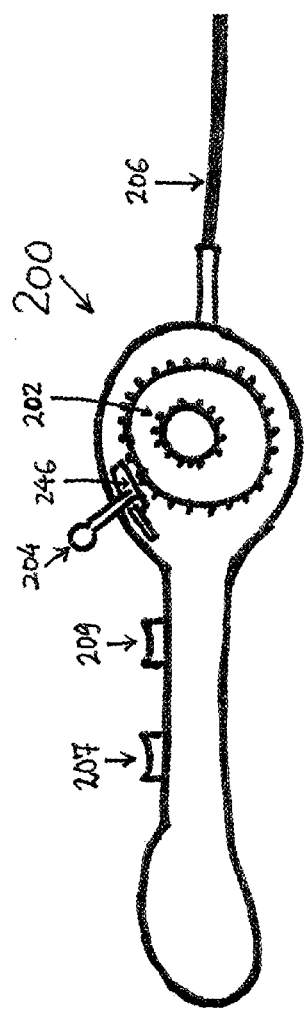
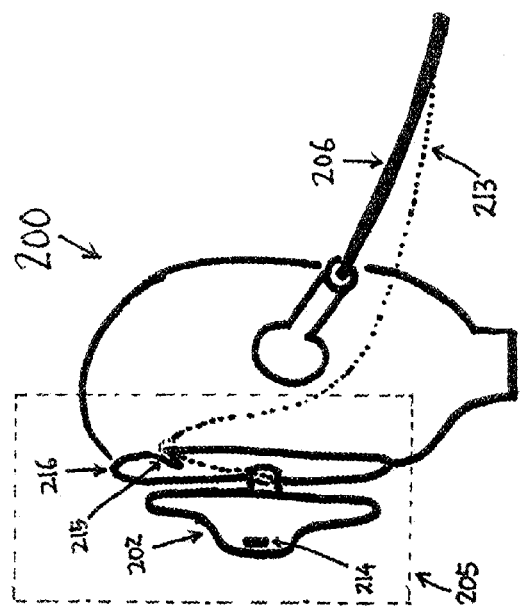
FIG. 2B
FIG. 2C

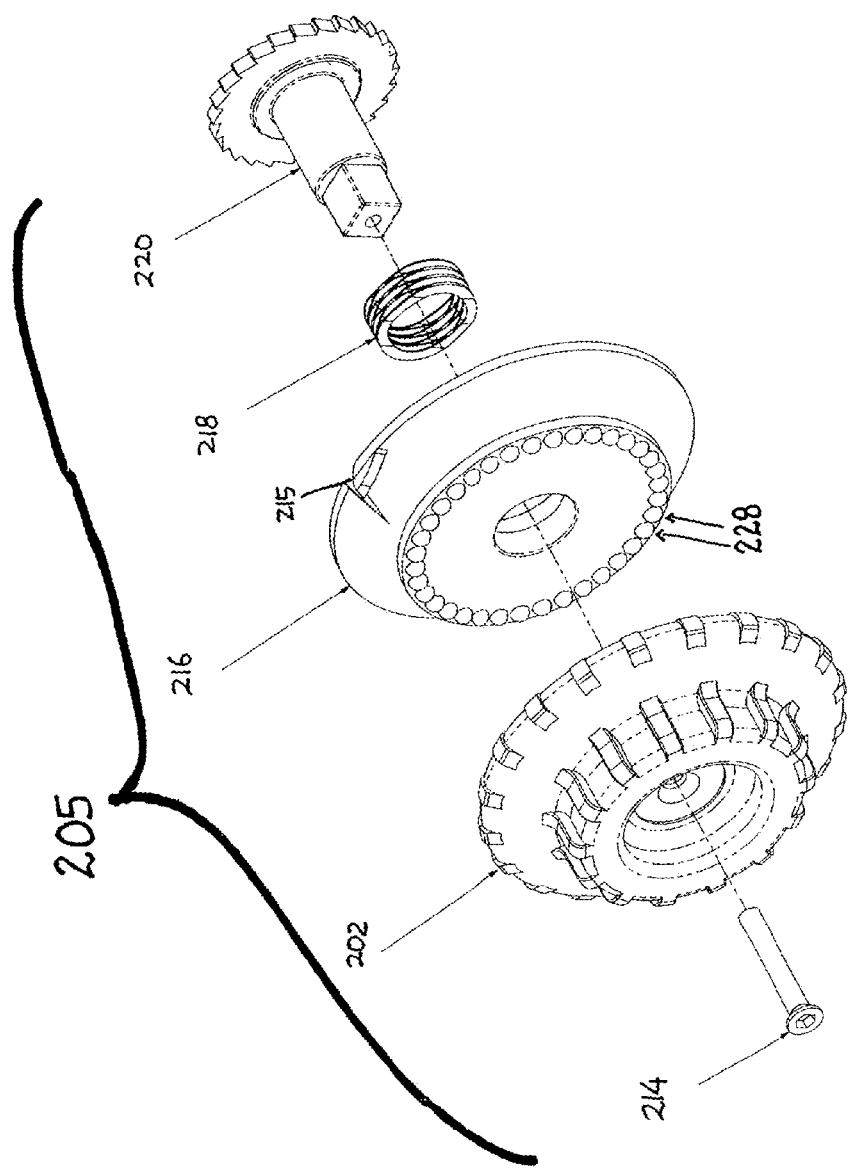

TETHER TENSIONING DEVICES AND RELATED METHODS

CROSS-REFERENCE TO RELATED APPLICATIONS

This application claims the benefit of U.S. Provisional Application No. 61/104,681, filed Oct. 10, 2008, and of U.S. Provisional Application No. 61/104,686, filed Oct. 10, 2008, the disclosures of both of which are incorporated herein by reference in their entirety.

TECHNICAL FIELD

The devices, methods, and kits described herein relate generally to tensioning tethers that have been deployed to a target site in a body of a subject. More specifically, the devices, methods, and kits described here relate to tensioning tethers during procedures for tightening or compressing tissue, and may in some variations allow for adjustable tensioning of such tethers.

BACKGROUND

Many different medical procedures involve the use of tethers, and some such medical procedures further involve tensioning the tethers. For example, tethers may be used to tighten or compress tissue (e.g., by bringing two pieces or sections of tissue together). The tissue may, for example, be soft tissue, such as muscle tissue or fat tissue. In some cases, a mitral valve that is experiencing mitral regurgitation may be repaired by deploying tethered anchors into tissue in the vicinity of the valve, and tensioning the tether. Tensioning the tether can provide a cinching effect that brings the anchors closer together, thereby reducing the circumference of the valve and alleviating the mitral regurgitation. Exemplary devices and methods for mitral valve repair are described, for example, in U.S. Patent Application Publication Nos. US 2006/0190030 A1, US 2006/0122633 A1, and US 2008/0172035 A1, all of which are hereby incorporated by reference in their entirety.

If a tether is tensioned too much in a tissue repair procedure, then the tissue may become damaged. Alternatively, if a tether is not sufficiently tensioned, then the underlying problem may not be fixed. Additionally, in minimally invasive catheter-based procedures in which the target site is located remotely from the incision site, it may be difficult to control the tension of a tether that is deployed at the remote site.

Accordingly, it would be desirable to provide devices, methods, and kits for tensioning a tether relatively precisely and/or efficiently. Moreover, it would be desirable to provide devices, methods, and kits that allow for adjustable tether tensioning. It would further be desirable for such devices, methods, and kits to provide for other forms of manipulation of the tether (e.g., by locking and/or cutting the tether).

SUMMARY

Described here are devices, methods, and kits for tensioning tethers. A tether may be tensioned, for example, to result in a tightening or compression of tissue, such as soft tissue (e.g., by pulling two or more pieces or sections of the tissue together). In some variations, the methods described here may be used on heart tissue. In certain variations, the methods may be used on heart tissue while the heart is still beating (e.g., making the overall heart repair procedure and/or recovery easier on the patient). Devices for locking and/or cutting such tethers (prior to, during, and/or after tensioning the tethers) are also described here.

Certain variations of the tensioning devices described here comprise a handle portion comprising a housing and a rotatable tensioning member coupled to the housing and configured to engage a tether. Rotating the rotatable tensioning member in one direction may increase the tension of a tether engaged by the rotatable tensioning member, and rotating the rotatable tensioning member in another direction (e.g., opposite the first direction) may decrease the tension of a tether engaged by the rotatable tensioning member. The rotatable tensioning member may comprise a lock-out mechanism that provides for a maximum amount of tensioning of a tether engaged by the rotatable tensioning member. Some variations of methods described here may comprise engaging a tether with the rotatable tensioning member, rotating the rotatable tensioning member to tension the tether, and releasing at least some of the tension in the tether without cutting the tether (e.g., by rotating the rotatable tensioning member in a different direction).

In some variations, the device may comprise a gear that is configured to rotate the rotatable tensioning member. In some such variations, the device may further comprise a lever configured to activate the rotatable tensioning member to rotate in one of two directions. The lever may have a first position in which the lever engages the gear, and a second position in which the lever releases the gear. When the lever is in the first position, it may maintain the tension of a tether engaged by the rotatable tensioning member in a static state.

Certain variations of the rotatable tensioning member may comprise a tensioning wheel that is coupled to a bobbin configured to engage a tether. Some variations of the methods may comprise engaging a tether with a notch on the bobbin and/or winding the tether around the bobbin. In some variations, the bobbin may be coupled to the tensioning wheel by a compression spring. The compression spring may have a spring constant of at least about 10 lb/inch and/or at most about 30 lb/inch. The compression spring may exert a force on the bobbin that determines the rotatability of the bobbin. Alternatively or additionally, the bobbin and the tensioning wheel may be coupled by a high-friction element. The high-friction element may apply a frictional force on the bobbin that determines the rotatability of the bobbin. The tensioning wheel may be configured to disengage from the bobbin when the tension of a tether engaged by the rotatable tensioning member reaches a predetermined value.

Certain variations of the tensioning devices described here may comprise an elongated member, such as a catheter, coupled to a distal portion of the handle portion. Some variations of the tensioning devices may comprise a locking and/or cutting element. The locking element may comprise, for example, a plug (e.g., a compressible plug) and a locking member configured to receive the plug. The locking member may comprise a lumen configured to receive the plug, and the plug may be rotatable when at least partially disposed within the lumen. The locking and/or cutting element may be located at (e.g., coupled to) a distal portion of the elongated member, and/or may be actuated by one or more controls in the handle portion of the device. In some variations, the locking element may be releasably coupled to a distal portion of the elongated member. Other variations of the tensioning device may not have a locking or cutting element at the distal portion of the elongated member.

Certain variations of the devices may comprise a pushing member. In such variations, the devices may comprise a button slider that is coupled to the pushing member such that sliding the button slider translates the pushing member. Other variations of pushing member actuators may alternatively or additionally be used. In some variations, the pushing member may be translated toward the plug of a locking element to push the plug into a lumen of a locking member of the locking element. The device may alternatively or additionally comprise another actuator (e.g., a button slider) that may be actuated to decouple a locking element from a distal portion of an elongated member of the device. The elongated member may comprise a sheath having a lumen, and the pushing member may be disposed within the lumen. In such cases, a button slider may be coupled to the sheath, and sliding the button slider may proximally withdraw the sheath to decouple a locking element from a distal portion of the elongated member. Of course, other variations of sheath-withdrawing mechanisms may alternatively or additionally be used.

Some variations of the devices that comprise a cutting element may also comprise one or more button sliders (e.g., that are configured to slide along an outer surface of the handle portion). A button slider may be coupled to the cutting element such that sliding the button slider moves the cutting element. Other variations of cutting element actuators may alternatively or additionally be used.

In some variations, the handle portion may comprise one or more retainers (e.g., that may be positioned to control actuation of one or more locking and/or cutting elements). The retainers may, for example, be configured to fit within one or more apertures in a housing of the handle portion. In certain variations, the retainers may block actuation of one or more controls (e.g., button sliders), while permitting actuation of one or more other controls. In some variations, the retainers may regulate the sequence in which the controls in the handle portion are actuated.

Some variations of the methods described here may comprise tensioning a tether that is fixedly coupled to a first anchor and slidably coupled to a second anchor, while both anchors are engaging a portion of body tissue. Tensioning the tether may provide a cinching effect that decreases the distance between the first and second anchors. The methods may also comprise releasing at least some of the tension in the tether without cutting the tether. The tether tension may be increased or decreased depending on the desired effect upon the tissue. Some tensioning methods may be used for heart valve repair (e.g., on a beating heart). In certain variations, after the desired tension has been achieved, the tether may be secured by a locking element to retain the tension. In some variations, the tether may then be cut, either by the same device that tensioned and/or locked the tether, or by a separate cutting device. In some cases, additional tension may be applied to the tether prior to cutting the tether.

Some variations of the kits described here may comprise an anchor delivery device and at least one tether tensioning device. Additional tether tensioning devices may be included (e.g., to allow for different ranges of tension to be applied to a tether). Some kits may also include a tether locking device and/or a tether cutting device.

BRIEF DESCRIPTION OF THE DRAWINGS

FIG. 2B is a side view of a handle portion of the device of FIG. 2A, FIG. 2C is a front view of the handle portion of the device shown in FIG. 2B.

FIG. 2G is another front perspective exploded view of the rotatable tensioning member of FIGS. 2E and 2F.

DETAILED DESCRIPTION

Described here are methods and devices for tensioning a tether. In some variations, the tether may be tensioned to tighten or compress tissue, such as soft tissue. Soft tissue includes, for example, muscle tissue and fat tissue, while hard tissue includes, for example, bone tissue. Methods and devices for locking and/or cutting a tether are also described. The devices and methods described here may be used in any appropriate procedures and locations for which such tether tensioning, locking, and/or cutting is desired. While not so limited, the devices and methods described here may be used, for example, in Natural Orifice Transluminal Endoscopic Surgery ("NOTES") procedures, heart valve repair procedures (e.g., mitral valve annulus repair procedures), and/or endoscopic procedures (e.g., laparoscopy and/or arthroscopy). Some of the devices described here may be used to tension a tether, while other devices described here may be used to both tension a tether and lock and/or cut the tether. Specific examples of methods and devices will now be described in further detail below.

Figure 1A:
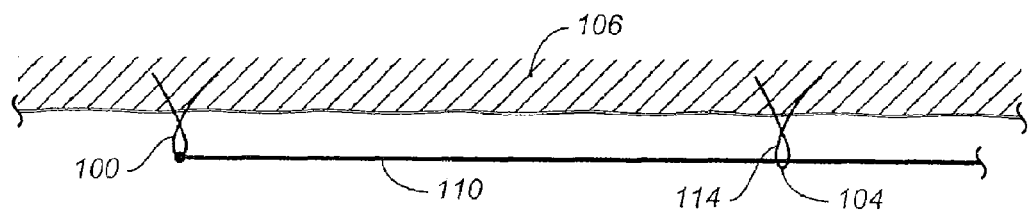
FIGS. 1A and 1B illustrate the tightening of tissue of a subject using a tether.
Figure 1B:
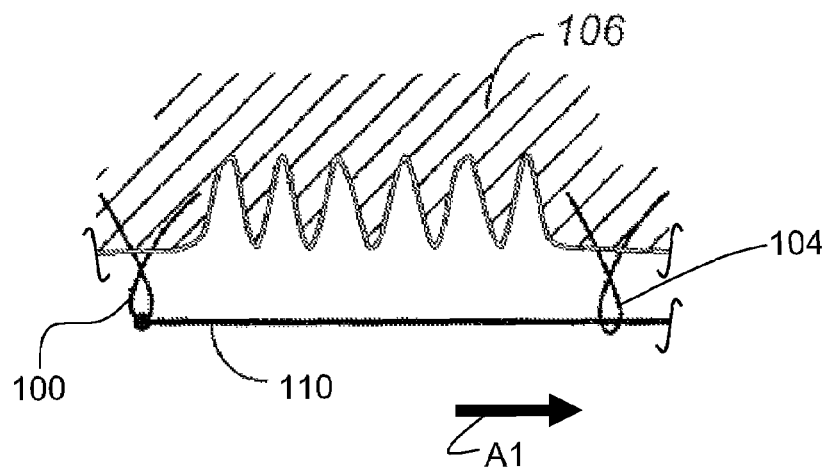

Turning now to the figures, FIG. 1A shows two anchors (100) and (104) anchored into tissue (106) of a subject. A tether (110) is fixedly attached to anchor (100), and is threaded through a loop region (114) of anchor (104). As shown in FIG. 1B, when tether (110) is pulled upon in the direction of arrow (A1), a cinching effect results, such that anchors (100) and (104) are brought closer together, and the tissue length between anchors (100) and (104) is reduced. In this way, tissue (106) is compressed between anchors (100) and (104). While two anchors are shown in FIGS. 1A and 1B, in some cases multiple anchors may be used. After tether (110) has been tensioned by a desired amount, tether (110) may be locked to maintain the tension, and in some cases, excess portions of tether (110) may be cut and removed.

The above-described process may be used in a wide variety of tissues. For example, in some variations, anchors that are connected to each other by a tether may be deployed into tissue in the region of a mitral valve annulus. The tether may then be tensioned to help provide a cinching effect, which restructures the mitral valve annulus (e.g., to reduce mitral valve regurgitation). Thereafter, the tether may be locked in place to maintain the cinching effect. Finally, excess portions of the tether may be cut and removed. Mitral valve repair is described, for example, in U.S. Patent Application Publication Nos. US 2006/0190030 A1, US 2006/0122633 A1, and US 2008/0172035 A1, which were previously incorporated by reference in their entirety, and of U.S. Patent Application Publication No. US 2008/0177380 A1, which is hereby incorporated by reference in its entirety. In certain variations, the above-described process may be used in a heart reshaping procedure, such as a ventricular remodeling procedure that is used to repair a heart experiencing valve dysfunction. Heart repair procedures, including heart reshaping procedures, are described, for example, in U.S. Patent Application Publication No. US 2009/0234318 A1, which is hereby incorporated by reference in its entirety.

As discussed above, the devices and methods described herein may be used, as appropriate, in any of a number of different sites within the body and/or to assist with any of a number of different types of procedures. As an example, the devices and methods described herein may be used in NOTES procedures. As another example, the devices and methods described herein may be used in heart procedures other than those involving mitral valve repair. For example, they may be used to repair an aortic valve or a tricuspid valve, or to secure a prosthetic heart valve, or they may be used in heart ports. As another example, the devices and methods may be employed in a procedure in which one or more tethers are used to reinforce an annuloplasty ring. Additionally, the devices and methods described herein may be used, for example, in a variety of open surgical procedures.

Anchors for use with the methods and devices described here may be any suitable anchor. The anchors may be made of any suitable material, may be any suitable size, and may be of any suitable shape. The anchors may be made of one material or more than one material. Examples of anchor materials include super-elastic or shape memory materials, such as nickel-titanium alloys and spring stainless steel. Examples of anchor shapes include T-tags, rivets, staples, hooks (e.g., C-shaped or semicircular hooks, curved hooks of other shapes, straight hooks, barbed hooks), multiple looped anchors, clips, and the like. The anchors may be configured to self-expand and self-secure into tissue, but need not be configured in such a fashion. Multiple anchors of the same shape may be used, or multiple anchors having different shapes may be used. Similarly, multiple anchors of the same size may be used, or multiple anchors having different sizes may be used. Illustrative examples of suitable anchors are described in more detail, for example, in U.S. Patent Application Publication Nos. US 2005/0273138 A1, US 2008/0058868 A1, US 2008/0045982 A1, US 2008/0045983 A1, US 2008/0051810 A1, and US 2008/0051832 A1, all of which are hereby incorporated by reference in their entirety. Moreover, while anchors have been described, any other type of suitable fasteners or implants (e.g., leads, electrodes, etc.) may be used with one or more of the devices and/or methods described here. Additionally, some procedures employing the devices and methods described herein may not involve any anchors or other types of fasteners. As an example, certain variations of the devices and methods described here may be used to lock and/or cut a tether that has been sewn through tissue.

Tethers may be one long piece of material or two or more pieces, and may comprise any suitable material, such as suture, suture-like material, a DACRON® polyester strip or the like. In some variations, tethers may be in the form of monofilament or multifilament textile yarns or fibers. Tethers may also have various braided textile configurations. While a tissue-tightening or -compressing procedure using one tether has been described, other procedures for modifying tissue may involve the use of multiple tethers, such as 2, 3, 4, 5, or 10 tethers. When multiple tethers are used, at least some of the tethers may be associated with (e.g., fixedly attached to) different anchors, and/or at least some of the tethers may be associated with (e.g., fixedly attached to) the same anchor. The devices and methods described herein may apply to single tether procedures, or to multiple tether procedures. As an example, a tensioning, locking and/or cutting device may be used to tension, lock, and/or cut more than one tether, either simultaneously, or at different times.

Figure 2A:
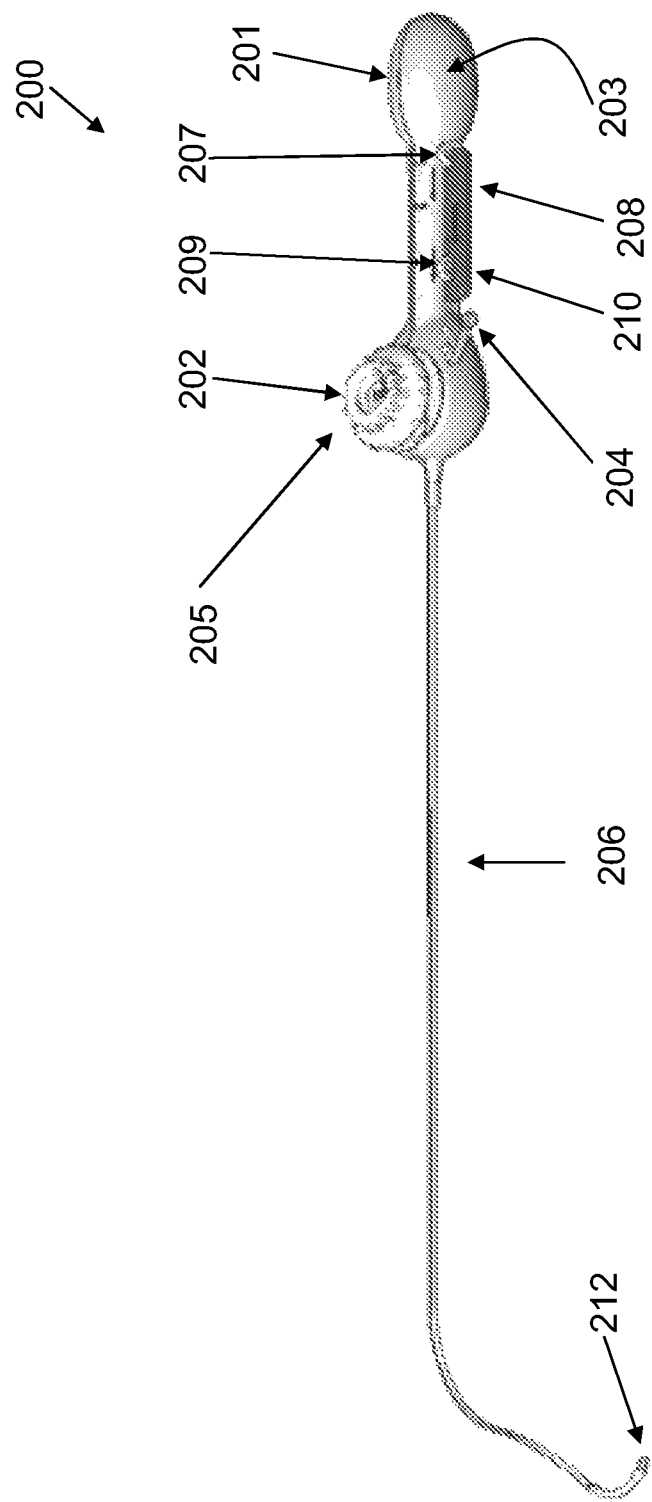
FIG. 2A is a perspective view of a variation of a device for tensioning and/or locking a tether.

In some cases, a tether may be tensioned by hand. Alternatively or additionally, one or more tensioning devices may be used to tension the tether. For example, FIGS. 2A-2Z show a variation of a tether tensioning device (200) and its components. As shown in FIGS. 2A-2C, tether tensioning device (200) comprises a handle portion (201) coupled to an elongated member (206) having a locking element (212) in its distal portion. While locking element (212) is located in the distal portion of elongated member (206), locking elements may alternatively or additionally be located in other portions of an elongated member. Elongated member (206) may, for example, be in the form of a catheter. Handle portion (201) comprises a housing (203), a rotatable tensioning member (205) coupled to housing (203), and a release lever (204) protruding from a double-notched aperture (246) in housing (203). Referring specifically to FIG. 2C, rotatable tensioning member (205) comprises a tensioning wheel (202) and a bobbin (216) coupled by a screw (214). Rotatable tensioning member (205) further comprises a compression spring (218) and a gear (220) (FIGS. 2D-2G). Handle portion (201) also comprises a small-hole button slider (207) and a large-hole button slider (209). The button sliders are configured to actuate and release the locking element in the distal portion of elongated member (206), as described in further detail below.

The motion of button sliders (207) and (209) may be restricted by removable retainers configured to fit into slots within which the sliders are slidably disposed. For example, FIG. 2A shows a first retainer (208) that limits or prevents motion by small-hole button slider (207) when in place, and a second retainer (210) that limits or prevents motion by large-hole button slider (209) when in place. (FIG. 2B shows handle portion (201) when first and second retainers (208) and (210) have been removed.) When in place, retainers (208) and (210) physically obstruct the track on which button sliders (207) and (209) slide. While retainers having specific configurations have been shown, it should be understood that retainers having any configuration suitable to temporarily obstruct or restrain the button sliders (or any other appropriate actuators) may be used.

Figure 2D:
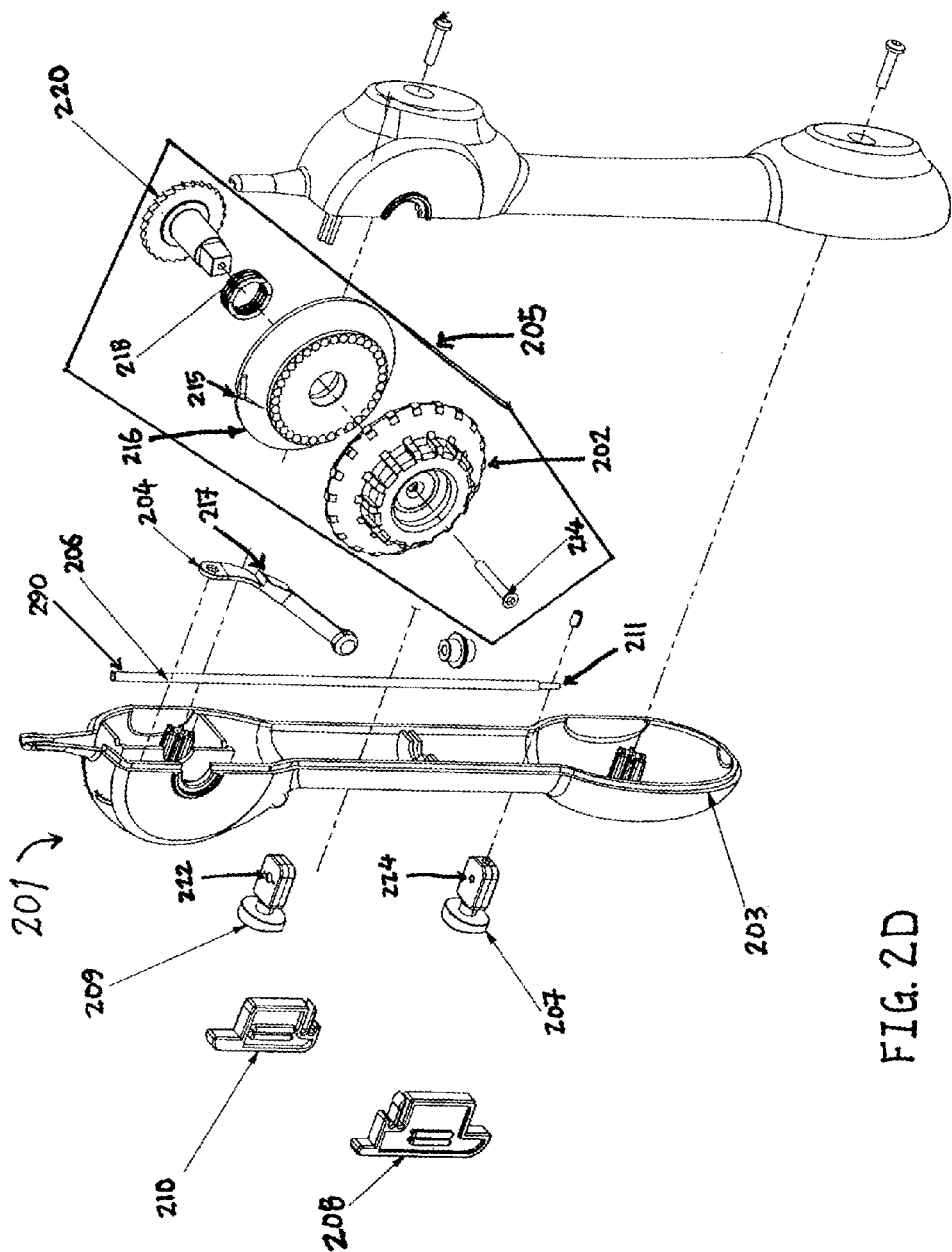
FIG. 2D is an exploded view of the handle portion of FIGS. 2B and 2C.
Figure 2E:
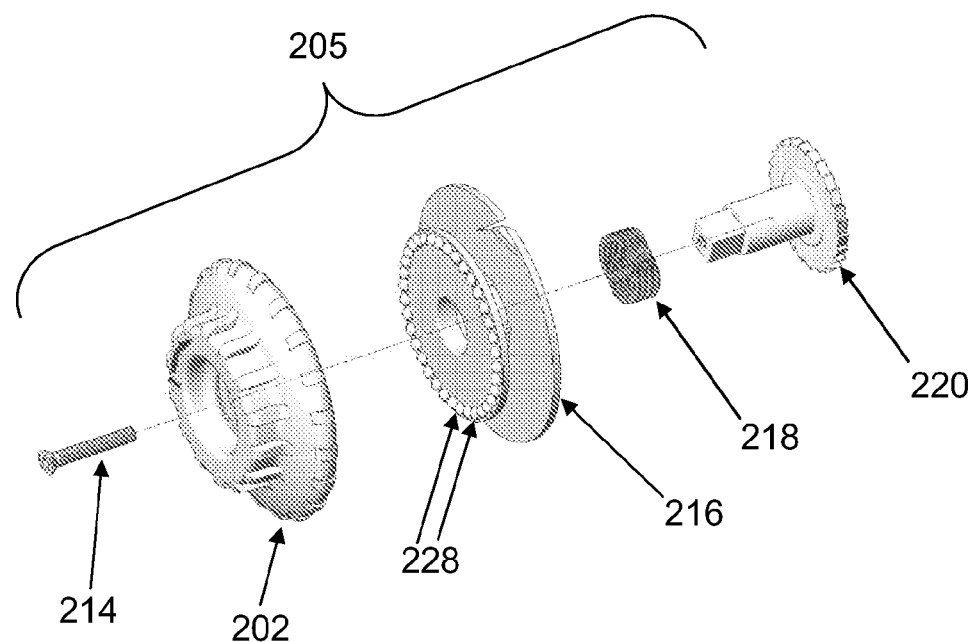
FIG. 2E is a front perspective exploded view of a rotatable tensioning member of the handle portion of FIGS. 2B-2D.
Figure 2F:
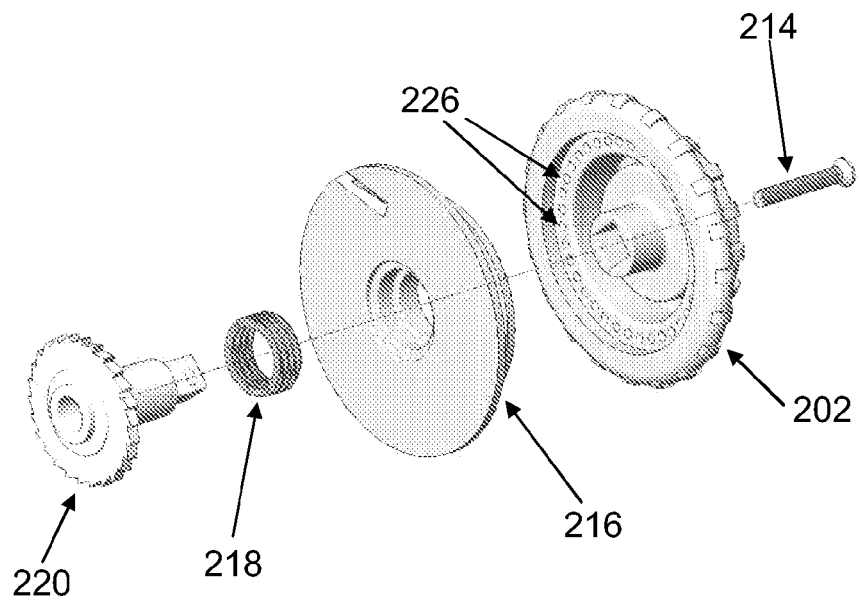
FIG. 2F is a back perspective exploded view of the rotatable tensioning member of FIG. 2E.
Figure 2H:
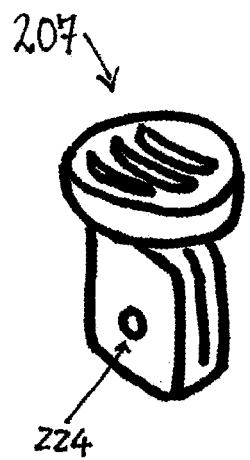
FIG. 2H is a perspective view of a first button slider of the handle portion of FIGS. 2B-2D.
Figure 2I:
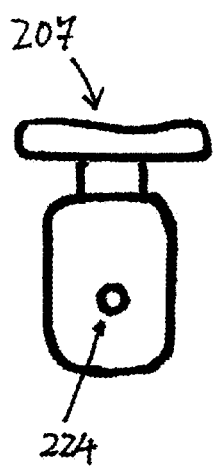
FIG. 2I is a side view of the first button slider of FIG. 2H.
Figure 2J:
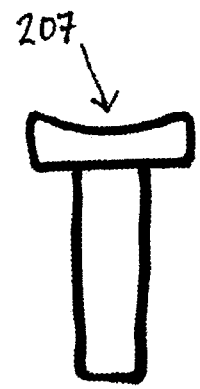
FIG. 2J is a front view of the first button slider of FIGS. 2H and 2I.
Figure 2K:
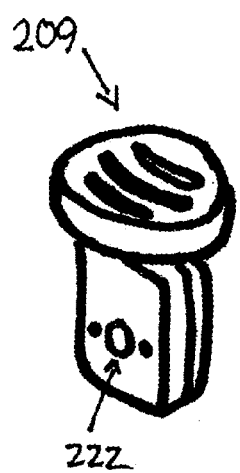
FIG. 2K is a perspective view of a second button slider of the handle portion of FIGS. 2B-2D.
Figure 2L:
FIG. 2L is a side view of the second button slider of FIG. 2K.
Figure 2M:
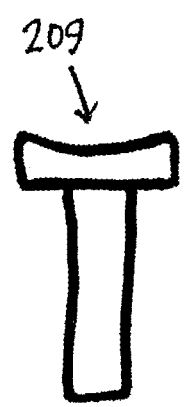
FIG. 2M is a front view of the second button slider of FIGS. 2K and 2L.

FIG. 2D shows an exploded view of tether tensioning device (200). As shown there, release lever (204) comprises a shoulder portion (217) that can engage with the individual teeth of gear (220) of rotatable tensioning member (205). As also shown there, the proximal portion of elongated member (206) is disposed within housing (203). Elongated member (206) comprises an outer member (290) and an inner member (211) at least partially disposed within a lumen of the outer member. Outer member (290) passes through an aperture (222) in large-hole button slider (209), and inner member (211) passes through an aperture (224) in small-hole button slider (207). As shown, the diameter of aperture (222) may be larger than the diameter of aperture (224). Moreover, the diameter of outer member (290) may be larger than the diameter of aperture (224), such that outer member (290) is not able to pass through aperture (224).

Tether tensioning device (200) may be used to tension and/or lock a tether. In some variations, a tether tensioning method may comprise coupling a tether to rotatable tensioning member (205), as shown in FIG. 2C, and rotating the rotatable tensioning member to tension tether (213) by a desired amount. More specifically, tether (213) may be secured to bobbin (216) by threading the tether into a notch (215) in bobbin (216), and then winding the tether around the bobbin. Tensioning wheel (202) and bobbin (216) are coupled such that they rotate in unison. Thus, tether (213) may be tensioned by rotating tensioning wheel (202) in one direction, and some or all of the tension in tether (213) may be released by rotating tensioning wheel (202) in the opposite direction. Tether (213) may be tensioned in continuous and/or discrete increments. In certain variations, the amount of tension that has been applied to a tether may be measured. As an example, a torque gauge may be positioned in tensioning wheel (202), and the tether tension may be measured based on the radial distance from the center of bobbin (216) to notch (215).

Rotatable tensioning member (205) is depicted in additional detail in FIGS. 2E-2Q. As shown there, tensioning wheel (202) is coupled to bobbin (216) and gear (220) via screw (214). Compression spring (218), which is disposed between bobbin (216) and gear (220), allows the entire rotatable tensioning member to rotate when tensioning wheel (202) is rotated. In some variations, compression spring (218) may have a spring constant of from about 10 lb/inch to about 30 lb/inch. Compression spring (218) may be made of any suitable material or materials, such as but not limited to, steel, aluminum, and/or ELGILOY® alloy. Examples of suitable materials for tensioning wheel (202), bobbin (216), and/or gear (220) include polymers, such as polycarbonate and acrylonitrile butadiene styrene (ABS). Other suitable materials may alternatively or additionally be used. The tensioning wheel, bobbin, and gear may be made of the same material or different materials. Screw (214) may be made of, for example, one or more metal alloys (e.g., stainless steel) and/or polymers such as polycarbonate and acrylonitrile butadiene styrene (ABS).

Tensioning wheel (202) comprises detents (226) that correspond to bearings (228) on bobbin (216). In use, compression spring (218) pushes gear (220), bobbin (216) and tensioning wheel (202) together. When these components are compressed together, bearings (228) engage detents (226), which allows tensioning wheel (202) and bobbin (216) to rotate in unison. The detents and bearings may be of any size or shape such that they are able to engage each other. Moreover, any suitable number of detents and bearings may be used.

Once the tether has been coupled to bobbin (216), turning the tensioning wheel causes the bobbin to turn as well, thereby tensioning the tether. Additionally, a torque is generated that opposes the spring force of compression spring (218). If the torque force surpasses the spring force, then bearings (228) will be forced out of detents (226), and bobbin (216) will slip and become disengaged from tensioning wheel (202). As a result, rotation of the tensioning wheel will no longer result in rotation of the bobbin. Thus, the configuration of rotatable tensioning member (205) sets a maximum tension that can be applied to a tether, after which point the bobbin becomes disengaged from the tensioning wheel, and the device may not be used to further increase the tension of the tether.

The spring force of compression spring (218) depends on the stiffness of the compression spring. Thus, the stiffness of the compression spring may be selected based on the desired maximum tension to be applied to the tether. A rotatable tensioning member with high compression spring stiffness may generally allow for a higher maximum tether tension than a rotatable tensioning member with low compression spring stiffness. The stiffness of a compression spring is related to the spring constant of the compression spring. As the spring constant increases, the stiffness also increases.

The use of a compression spring is only one variation of a mechanism by which a device may restrict the level of tension applied to a tether, thereby preventing unintentional over-tensioning of the tether. Other mechanisms that perform the same function may also be used. For example, in certain variations, a high-traction element, such as a rubber washer, may be used to engage the tensioning wheel to the bobbin, in place of the compression spring. Once the tension on the tether exceeds the opposing frictional force generated by the high-traction element, the bobbin is no longer rotatable with the tensioning wheel, and the tensioning device is unable to further increase the tension on the tether. It should be understood that these are only a few examples of mechanisms that set a maximum tension threshold that can be applied with a tensioning device, and other methods and configurations may alternatively or additionally be used.

Figure 2N:
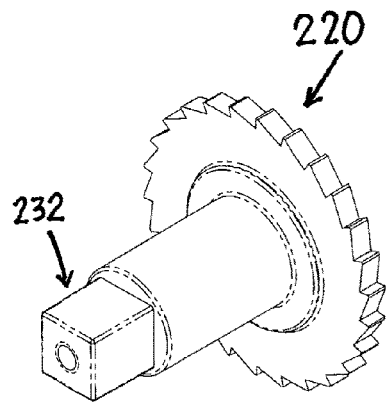
FIG. 2N is a rear perspective view of a gear of the rotatable tensioning member of FIGS. 2E-2G.
Figure 2O:
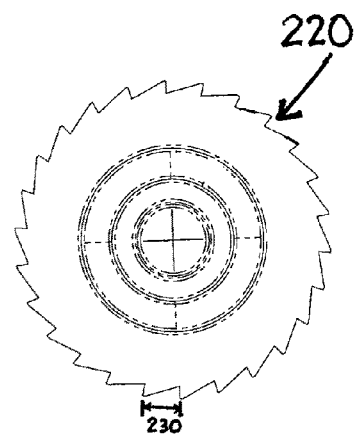
FIG. 2O is a front view of the gear of FIG. 2N.

FIGS. 2N-2U show various components of rotatable tensioning member (205) in greater detail. Referring first to FIGS. 2N and 2O, gear (220) has an inter-tooth distance (230) between each of its teeth. This inter-tooth distance establishes the discrete intervals by which tension can be increased when the tether is being tensioned. While the inter-tooth distance between each tooth of gear (220) is shown as uniform, in some variations, a gear may comprise teeth that are separated from each other by different distances (i.e., at least two of the distances may be different from each other—for example, the distances may vary along the entire circumference of the gear). In certain variations, inter-tooth distance (230) may be from about 0.1 inch to about 0.3 inch. Inter-tooth distance (230) may be selected, for example, based on the desired level of precision of tether tensioning. It should be appreciated that the smaller the inter-tooth distance, the more precisely the tension on the tether may be adjusted (i.e., because the tether tension is adjusted in smaller increments). Referring specifically now to FIG. 2N, a rectangular element (232) on the central axis of gear (220) couples gear (220) to tensioning wheel (202). However, other shapes and/or methods of attachment may be used to couple a gear to a tensioning wheel. For example, a gear may be coupled to a tensioning wheel using permanent adhesives, welding, and/or screws.

Figure 2P:
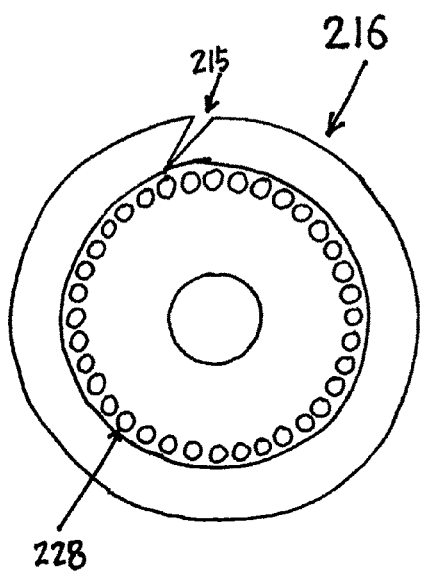
FIG. 2P is a front view of a bobbin of the rotatable tensioning member of FIGS. 2E-2G.
Figure 2Q:
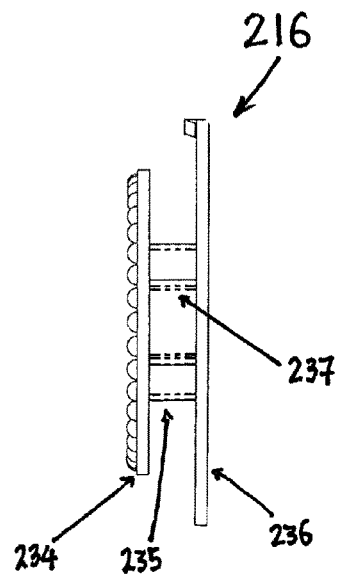
FIG. 2Q is a side view of the bobbin of FIG. 2P.

FIGS. 2P and 2Q show bobbin (216) in enhanced detail. As shown there, bobbin (216) comprises a first surface (234) including protruding bearings (228), a second surface (236) including notch (215), and an axis element (235) connecting the two surfaces. The surfaces may be of any suitable shape (e.g., circular, rectangular, etc.). First surface (234) includes thirty-six hemispherical bearings (228) arranged radially on first surface (234). However, any appropriate number of bearings of any shape may be used, as long as they are capable of engaging with detents (226) in tensioning wheel (202). The first surface, second surface, axis element, and bearings (228) may be made of any material or combination of materials, such as one or more polymers (e.g., polycarbonate, acrylonitrile butadiene styrene (ABS)), and metal alloys (e.g., stainless steel). The different components of bobbin (216) may be made of the same material or materials, or may be made of different materials. For example, in some variations, the first surface, second surface, and axis may be made of polycarbonate, and the bearings may be made of stainless steel.

As described above, bobbin (216) includes notch (215) on second surface (236) which aids in the securing of a tether wound around axis element (235). In certain variations, the tether may be further secured using one or more temporary adhesives. While bobbin (216) includes just one notch (215), some variations of bobbins may include multiple notches, such as 2, 3, 4, or 5 notches. Additionally, in certain variations, axis element (235) may comprise friction-enhancing features. For example, and as shown in FIG. 2Q, axis element (235) may comprise ridges (237). Alternatively or additionally, an axis element may comprise one or more sticky or tacky coatings on its surface (e.g., formed of one or more soft elastomeric materials, such as KRATON™ polymers). An axis element of a bobbin, as well as a tether being tensioned by the bobbin, may comprise any number of features, coatings, or combinations thereof that enhance the engagement between the axis element and the tether.

Figure 2R:
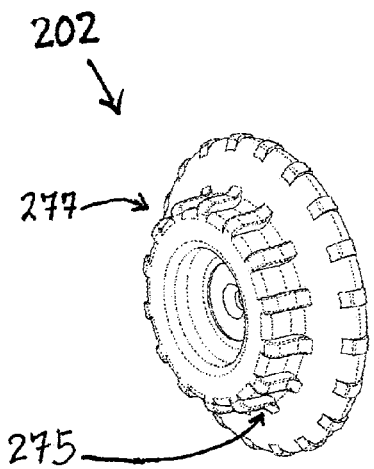
FIG. 2R is a front perspective view of a tensioning wheel of the rotatable tensioning member of FIGS. 2E-2G.
Figure 2S:
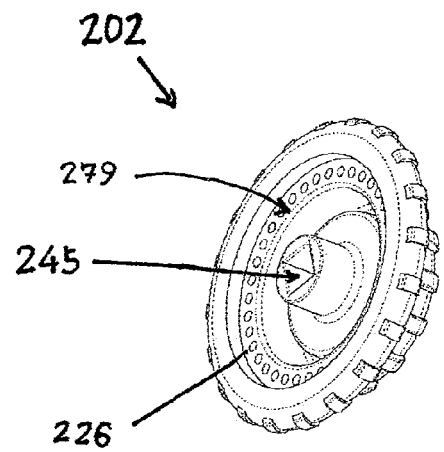
FIG. 2S is a back perspective view of the tensioning wheel of FIG. 2R.
Figure 2T:
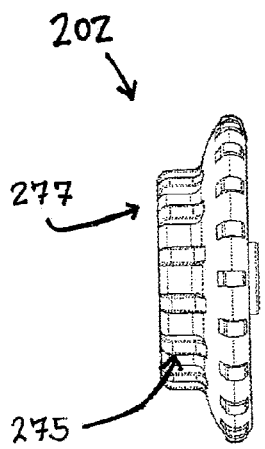
FIG. 2T is a side view of the tensioning wheel of FIGS. 2R and 2S.
Figure 2U:
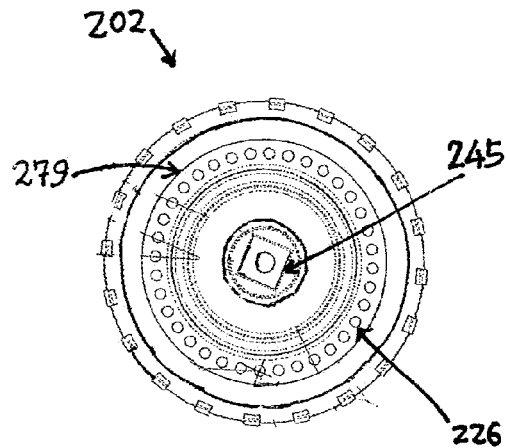
FIG. 2U is a back view of the tensioning wheel of FIGS. 2R-2T.
Figure 2V:
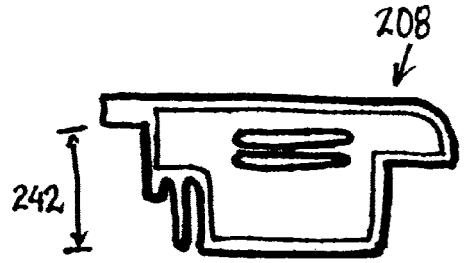
FIG. 2V is a side view of a first retainer of the handle portion of FIGS. 2B-2D.
Figure 2W:
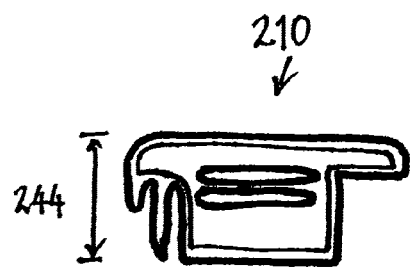
FIG. 2W is a side view of a second retainer of the handle portion of FIGS. 2B-2D.

FIGS. 2R-2U show tensioning wheel (202) in greater detail. As shown in FIGS. 2R and 2T, tensioning wheel (202) may comprise protruding features such as ridges (275) and/or grips on its outer surface (277) to provide greater traction. The inner surface (279) of tensioning wheel (202) contains radially-arranged detents (226), as shown in FIGS. 2S and 2U. While detents (226) are in an evenly spaced radial arrangement, other suitable arrangements may be used. As an example, in some variations, a tensioning wheel may comprise detents that are not uniformly spaced apart from each other and/or that do not form a radial configuration. Detents (226) are configured to engage with bearings (228) in bobbin (216). Additionally, in this variation, the center axis of tensioning wheel (202) comprises a rectangular-shaped detent (245) which engages with rectangular element (232) of gear (220) (FIG. 2N). However, other variations of a tensioning wheel and gear may comprise one or more detents and corresponding elements of different sizes and/or shapes that are configured to engage with each other. Moreover, in some variations, a tensioning wheel may comprise a high-friction material on all or a portion of its outer surface (e.g., to enhance traction between the tensioning wheel and a bobbin). It should be understood that any suitable mechanism or material may be used on the surface (e.g., the inner surface) of a tensioning wheel to engage the tensioning wheel to a bobbin.

Figure 2X:
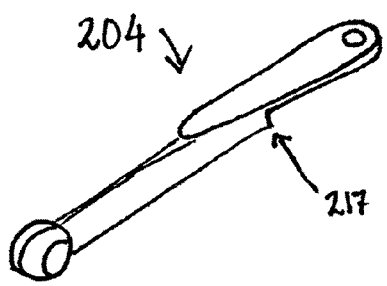
FIG. 2X is a perspective view of a lever of the handle portion of FIGS. 2B-2D.

FIG. 2X shows release lever (204) in enlarged detail. As shown there, release lever (204) comprises shoulder portion (217), which is configured to temporarily engage with a tooth of gear (220). Release lever (204) extends from double-notched aperture (246) (FIGS. 2B and 2Y), which is formed in the top surface of tensioning device (200). When release lever (204) is engaged in one notch, tensioning wheel (202) can be rotated unidirectionally, in discrete intervals. In certain variations, this configuration may only allow for the tension in a tether to be increased incrementally, but in other variations, this configuration may allow for the tension to be both increased and decreased incrementally. When release lever (204) is engaged in the other notch, tensioning wheel (202) may be rotated bidirectionally, in continuous increments. Release lever (204) may be made of any suitable material or materials, such as polymers (e.g., polycarbonate and/or ABS). It should also be understood that other variations of the release lever may not require that the lever extend from the tensioning device. For example, in certain variations, a release lever may be implemented internally and actuated by a slider or button. In some variations, a release lever may comprise one or more features that are capable of articulating with a gear tooth, other than, or in addition to, a protrusion.

As described above, in some variations, a tether may be tensioned and locked by the same device. The locking may help to maintain the tension in the tether (e.g., thereby maintaining a cinching effect created by the tensioned tether). For example, tether tensioning device (200) includes locking element (212) at the distal portion of elongated member (206). Thus, in addition to being used to tension a tether, tether tensioning device (200) may also be used to lock a tether. However, in certain variations, two different devices may be used to tension and lock a tether, with one device being used to tension the tether, and the other device being used to lock the tether. In some variations, a single device may be used to tension, lock, and cut a tether. Cutting devices are described in further detail below. It should also be noted that in certain variations, a device that is configured to tension a tether and to lock and/or cut a tether may be used only to tension a tether or only to lock and/or cut a tether.

The mechanism and components that may be employed to lock a tether using tether tensioning device (200) will now be described. Referring to FIG. 2D, small-hole button slider (207) may be used to actuate inner member (211), which functions as a pushing member that pushes a plug of locking element (212) into a locking tube of locking element (212). Prior to actuation of inner member (211), a tether may be routed into the locking tube. Thus, when inner member (211) is actuated, it pushes the plug into the locking tube, securing the tether between the plug and the locking tube and thereby locking the tether.

In certain variations, after locking element (212) has been used to lock a tether, the locking element may be released from the rest of tether tensioning device (200). For example, once the tether has been tensioned and locked, the locking element may be released from the device to leave the locking element in the body. This allows any other portions of the device that are within the body to then be removed from the body. Referring again to FIG. 2D, large-hole button slider (209) may be actuated to decouple locking element (212) from elongated member (206), thereby releasing the locking element from the rest of tether tensioning device (200).

Figure 2Y:
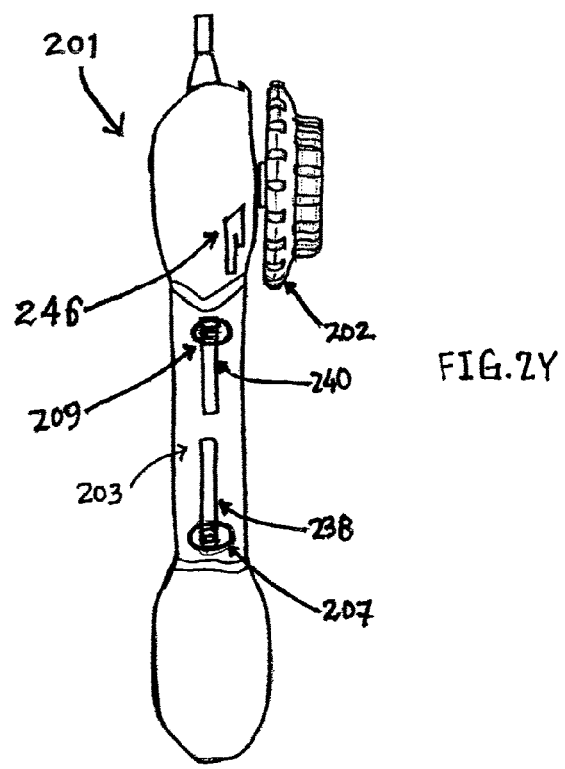
FIG. 2Y is a top view of the handle portion of FIGS. 2B-2D.
Figure 2Z:
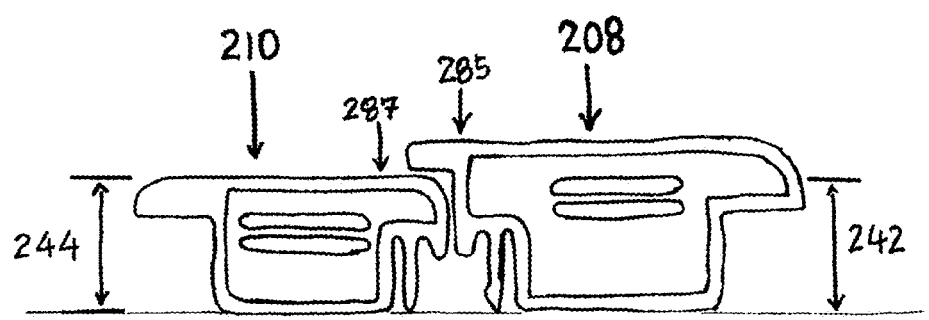
FIG. 2Z is a side view of the first retainer of FIG. 2V and the second retainer of FIG. 2W, as they may be assembled when used in the handle portion of FIG. 2D.

First and second retainers (208) and (210) may be used to help ensure that locking element (212) is deployed and released properly. In other words, the first and second retainers may be used to ensure that the locking element is deployed prior to being released, and that the locking element is not deployed or released prematurely. Referring to FIG. 2Y (which depicts handle portion (201) without release lever (204)), small-hole button slider (207) is slidably disposed within a slot (238) in housing (203) of handle portion (201). When moved within the slot, small-hole button slider (207) can actuate inner member (211), allowing the inner member to push a plug of locking element (212) into a locking tube of the locking element. Similarly, large-hole button slider (209) is slidably disposed within a slot (240) in housing (203) of handle portion (201). Moving large-hole button slider (209) within slot (240) can result in the decoupling of locking element (212) from elongated member (206). First and second retainers (208) and (210) may be temporarily disposed in slots (238) and (240), respectively, to prevent button sliders (207) and (209) from being actuated at the wrong time (e.g., prematurely, or in the wrong order). It should be noted that while both retainers may be used simultaneously (e.g., during shipping), in some variations, only one retainer may be used.

During use, both retainers (208) and (210) may initially be disposed within slots (238) and (240), respectively, to prevent unintentional actuation of either small-hole button slider (207) or large-hole button slider (209). First retainer (208) may then be removed from slot (238) to allow for the actuation of small-hole button slider (207), while the actuation of large-hole button slider (209) is still prohibited by the presence of second retainer (210) within slot (240). After the small-hole button slider has been actuated to lock a tether, second retainer (210) may be removed from slot (240) to permit the movement of large-hole button slider (209) within the slot, which may result in the release of locking element (212) from elongated member (206). While retainers (208) and (210) are depicted as external to housing (203) of handle portion (201), in some variations, one or more retainers may be internally disposed relative to a housing of a handle portion.

FIGS. 2H-2J show small-hole button slider (207) in enlarged detail. Small-hole button slider (207) may be made of, for example, one or more polymers such as polycarbonate and/or ABS. The diameter of aperture (224) in small-hole button slider (207) may be selected to allow aperture (224) to receive inner member (211) of elongated member (206). The inner member may form a friction fit with the aperture, such that movement of small-hole button slider (207) within slot (238) results in corresponding movement of inner member (211). In certain variations, the inner member may be further coupled to small-hole button slider (207) (e.g., using one or more adhesives, and/or by applying heat to fuse the inner member to the small-hole button slider).

FIGS. 2K-2M show large-hole button slider (209) in enlarged detail. Large-hole button slider (209) may be made of, for example, one or more polymers, for example, polycarbonate and/or ABS. The large-hole button slider may be made of one or more of the same materials as the small-hole button slider, or the button sliders may be made of different materials. The diameter of aperture (222) in large-hole button slider (209) may be selected to allow aperture (224) to receive outer member (290) of elongated member (206). The outer member may form a friction fit with the aperture, such that movement of large-hole button slider (209) within slot (240) results in corresponding movement of outer member (290). In some variations, outer member (290) may be in the form of a sheath that temporarily retains locking element (212). When the large-hole button slider is actuated, it may result in the proximal withdrawal of outer member (290), which may in turn result in the release of locking element (212) from elongated member (206).

FIG. 2V shows first retainer (208) in enlarged detail. First retainer (208) may be made of, for example, one or more polymers such as polycarbonate and/or ABS. As described above, first retainer (208) is sized and shaped to fit within slot (238) and thereby immobilize small-hole button slider (207) (e.g., preventing unintentional actuation of locking element (212)). The size and shape of first retainer (208) may also be selected so that the first retainer fits well with the second retainer when both retainers are disposed within their respective slots in housing (203) of handle portion (201).

FIG. 2W shows second retainer (210) in enlarged detail. Second retainer (210) may be made of, for example, one or more polymers such as polycarbonate and/or ABS. As described above, second retainer (210) is sized and shaped to fit within slot (240) and thereby immobilize large-hole button slider (209) (e.g., preventing unintentional release of locking element (212) from elongated member (206)).

First and second retainers (208) and (210) may be configured such that second retainer (210) cannot easily be removed from slot (240) until first retainer (208) has been removed from slot (238). This configuration may ensure that large-hole button slider (209) will not be actuated prior to actuation of small-hole button slider (207). As a result, locking element (212) may not inadvertently be released from elongated member (206) prior to being actuated to lock a tether. For example, and referring specifically to FIG. 2Z, a height (242) of first retainer (208) may be greater than a height (244) of second retainer (210). When the first and second retainers are both placed in their respective slots in housing (203) of handle portion (201), this height differential causes a top edge (285) of first retainer (208) to extend over a top edge (287) of second retainer (210), as shown in FIG. 2Z. It should be understood that this is only one retainer configuration, and other variations of retainer configurations may be used to prevent the unintentional actuation of button slider (207) and/or (209), and/or to ensure that small-hole button slider (207) is actuated prior to large-hole button slider (209).

In some variations, a tether tensioning device may comprise one or more retainers that are disposed within a housing of the device. Alternatively or additionally, a tether tensioning device may comprise one or more retainers that do not protrude into or out of a housing of the device. For example, a retainer may be in the form of an adhesive strip that temporarily covers a slot to limit movement of a button slider within the slot. In certain variations, one or more retainers may be labeled with numbers, and/or colored-coded, to indicate the order in which the button sliders are to be actuated. In some variations, a tether tensioning device may comprise one or more retainers that are not coupled to a handle portion of the device, while in other variations, a tether tensioning device may comprise one or more retainers that may be affixed to a handle portion of the device (e.g., with a tether, a snap-in mechanism, etc.). In certain variations, a single retainer may be used to perform the functions of both first retainer (208) and second retainer (210).

As described above, after a tether has been tensioned, the tether may then be locked or secured into place to maintain the tension. Different non-limiting variations of locking devices are described in further detail below.

Figure 3:
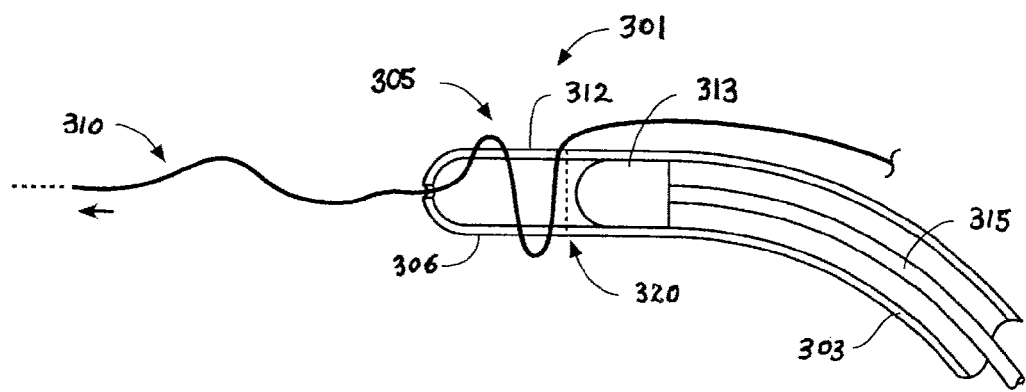
FIG. 3 shows a variation of a device that may be used to lock a tether.

For example, FIG. 3 shows a locking device (301) including a locking element (305) comprising a plug (313) and a hollow locking member (306). Hollow locking member (306) is releasably coupled to a tubular elongated member (303) in a distal region of the device. Elongated member (303) may be flexible over all or a portion of its length. As shown in FIG. 3, hollow locking member (306) is in the form of a distal extension of elongated member (303) (i.e., hollow locking member (306) extends beyond the distal end of elongated member (303)). However, in some variations, a locking device may comprise an elongated member and a locking member that is coupled to the elongated member, but that does not form a distal extension of the elongated member. Referring again to FIG. 3, hollow locking member (306) maintains the profile of elongated member (303), and may share a common wall with the elongated member. In some cases, though, a locking device may comprise an elongated member and a locking member that is smaller or larger than the elongated member in profile. Alternatively or additionally, the elongated member and the locking member may not share a common wall.

While the device shown in FIG. 3 is configured as a catheter, other configurations may be used. Moreover, the device may be scaled up (e.g., for use in a surgical procedure) or down (e.g., for use in a minimally invasive procedure), depending, for example, on the requirements of the particular procedure in which the device is to be used.

As shown in FIG. 3, a tether (310) is threaded through the distal region of locking device (301), particularly through hollow locking member (306). Although any suitable locking element may be included as part of a locking device, locking element (305) locks a tether when plug (313) is advanced into hollow locking member (306) such that the tether is secured between the plug and a wall of the locking member. As shown, tether (310) is threaded through multiple apertures in the wall (312) of hollow locking member (306). However, in some variations, a tether may be threaded through only one aperture in a wall of a locking member. Alternatively or additionally, a tether may pass through one or more apertures (e.g., passages or holes) in one or more other locations of a locking device (e.g., distally of the locking element).

Until the locking element is secured, the device may be moved along the tether (e.g., by sliding), or the tether may be pulled through the device. Thus, the tether may be used to provide a cinching effect by sliding the device distally down the tether. The apertures through the device shown in FIG. 3 may be positioned such that the device can still easily slide along the tether. In some variations, the tether may be threaded into the locking element in such a way that it winds in and out of the locking element, as suggested by FIG. 3.

In certain variations, the device may be slid along the tether until the tether has been pulled by the desired amount through the anchors, at which point the tether may be secured into position using the locking element. For example, and as described above, tether (310) of FIG. 3 may be secured into position by pushing plug (313) into hollow locking member (306) of locking element (305). In the variation shown in FIG. 3, plug (313) secures tether (310) by compressing at least a portion of the tether between the plug and the inner walls of hollow locking member (306).

A tether may be threaded or coupled to one or more components of a tensioning device by, for example, an operator of the tensioning device. For example, to thread a tether through a locking member comprising a wall portion with one or more apertures therethrough, a lasso may first be threaded through one or more of the apertures. The lasso may then be used to engage the tether and to thread the tether through the aperture or apertures (e.g., by pulling on the opposite end of the lasso). A tether may be coupled to one or more components of a handle portion of a tether tensioning device by, for example, grasping the tether and directly coupling it to the component or components. For example, the tether may be grasped, routed through a notch in a bobbin of a rotatable tensioning member, and wound around an axis element of the rotatable tensioning member. In some variations, a lasso may be used to thread a tether through an elongated member of a tether tensioning device (e.g., comprising a locking element and/or cutting element), and may thereafter be routed out of the elongated member and engaged with one or more components of a rotatable tensioning member by hand.

The plug and/or hollow locking member of the locking element may comprise one or more features that limit the likelihood of the plug being released from the hollow locking member. For example, the plug and/or hollow locking member may include adhesive, glue, or cement, and/or may be at least partially deformable so that once the plug has been inserted into the hollow locking member, the plug is retained within the locking member. As an example, the plug may comprise a material which is compressible or elastic to aid in locking the plug into the locking member. In certain variations, the plug may have polygonal (e.g., hexagonal) sides that interact with the inner surface of the locking member. The plug may be solid or hollow. The plug may have bumps, dimples, ribs, grooves, or holes on its surface to increase traction on the tether. The locking member may also include or comprise structures (e.g., rims, brackets, etc.) to help hold the plug in the locked configuration. In some variations, the locking member itself may alternatively or additionally be polygonal in cross-section. In certain variations, the plug and the locking member may have corresponding geometries, as described below. In some variations of devices, the plug and the locking member may each include different features that enhance the retention of the plug in the locking member.

The device shown in FIG. 3 further includes a pushing member (315) for pushing plug (313) into position to secure tether (310) within hollow locking member (306). The pushing member (shown in FIG. 3 as a rod, although other suitable forms of pushing members may be used) may be slidable within the lumen of the device. In some variations, the pushing member may include one or more guides (e.g., that guide the pushing member's direction) and/or stops (e.g., that limit the distance traveled by the pushing member and/or the force applied by the pushing member). Thus, there may be motion-limiting features on the device and/or pushing member to prevent the pushing member from being pushed too far forward, or from applying too much force, which could disturb either the locking element or the tissue (e.g., after separation of the locking element from the rest of the device).

As described above, a locking element may be releasably coupled to the rest of a device. Any appropriate method may be used to provide such a releasable coupling. In some variations, the locking element (or a portion thereof) may include a releasable coupling region, such as a region that can be separated or broken to release the locking element from the rest of the device. As an example, a locking element may be frangibly connected to the rest of a device, and may be decoupled from the device by breaking the frangible connection. For example, a locking element may be fused to another portion of the device (e.g., a distal portion of an elongated member). The fused region may later be broken to decouple the locking element from the other portion of the device. The amount of heat and/or pressure that is applied during the fusion process, as well as the number of fused regions and their locations, may be selected so that a specific amount of force can be applied to the fused regions to break them.

Different regions of a locking device may comprise different materials, or may comprise the same material or materials. In some variations, a locking device comprises a locking element formed of a first material, another portion formed of a second material, and a fused region between the locking element and the other portion that is formed of a third material (or combination of materials). Using different materials for different regions of a locking device may be advantageous if the different regions have different material requirements. For example, a more distal region of the device may be formed of one or more materials that provide relative flexibility, while a more proximal region may be formed of one or more materials that provide relative stiffness, or vice-versa. Moreover, while locking devices comprising one or more fused regions and multiple different materials have been described, some variations of locking devices may comprise fused regions and may be formed entirely of one material or combination of materials, and other variations of locking devices may comprise multiple different materials (e.g., 2, 3, 4, or 5 different materials) without comprising any fused regions.

In certain variations, a locking device may comprise a detachable locking element that is coupled to the rest of the device by a structurally weakened region. The structurally weakened region may, for example, be scored, etched, perforated, fractured, creased, slotted, and/or dimpled. An example of a perforated region (320) is shown in FIG. 3. The locking element may be made of the same material as the rest of the device, or the locking element and the rest of the device may be made of different materials. When a sufficient amount of force is applied to the structurally weakened region, the locking element may become separated from the rest of the device. Force may be applied to the structurally weakened region using, for example, a pushing member or any other suitable mechanism.

In some variations, a locking element may be releasably coupled to another portion of a locking device via at least one adhesive and/or a friction fit, so that the application of a certain amount of force causes the locking element to decouple from the other portion of the locking device. Additional non-limiting methods of releasably coupling a locking element to another portion of a locking device include fusing, brazing, soldering, and snap-locking. In some variations of locking devices, two or more different releasable coupling methods may be used in conjunction with each other.

Figure 4:
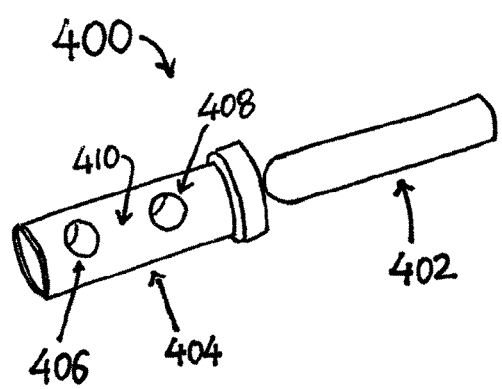
FIG. 4 is a perspective view of a variation of a tether-locking element.

Other variations of locking elements and/or members may be used, as appropriate. For example, FIG. 4 depicts a variation of a locking element (400) comprising a plug (402) and a tubular member (404) configured to receive plug (402). Tubular member (404) comprises a wall portion (410) with two apertures (406) and (408) therethrough. While two apertures are shown, in some variations, a wall portion of a tubular member may have just one aperture, or more than two apertures. Plug (402) and tubular member (404) may be made of the same material or materials, or may be made of different materials. In some variations, plug (402) and/or tubular member (404) may be made of one or more radiopaque materials (e.g., to provide visibility under X-ray fluoroscopy), and/or may also include one or more materials that allow them to be visible under other imaging modalities.

A tether may be routed through tubular member (404) in any of a number of different configurations, such that the tether is sufficiently engaged, yet slidable, within the tubular member. To lock the tether (e.g., after a desired tension has been applied), a pushing member (not shown) may be used to urge plug (402) into tubular member (404), thereby trapping the tether between plug (402) and wall portion (410) of tubular member (404).

As described above, in some variations, a locking element may be controllably decoupled from the rest of a device by applying a force. Force may be applied in any appropriate manner. For example, force may be applied by pushing on a pushing member, or may be in the form of hydraulic force (using saline, water, or the like), magnetic force, pressurized gas, etc. As an example, the same pushing member (315) of FIG. 3, used to push plug (313) and secure the locking element, may also be used to decouple the locking element from the rest of the device (e.g., by pushing the pushing member with additional force). In some variations, one force applicator (e.g., a pushing member) may be used to secure the locking element and another force applicator (e.g., a second pushing member) may be used to decouple the locking element from the rest of the device.

The amount of force required to decouple a locking element from the rest of a device may be predetermined. In variations where the same force applicator (e.g., a pushing member, fluid line, magnet, etc.) is used both to lock the tether and to decouple the locking element, the force required to decouple the locking element may be greater than the force required to secure the locking element and thereby lock the tether. For example, a device may be configured for its locking element to decouple after the application of greater than about 2 lbs of force, greater than about 3 lbs of force, greater than about 4 lbs of force, greater than about 5 lbs of force, greater than about 10 lbs of force, greater than about 20 lbs of force, or between about 2 lbs and about 5 lbs of force. The amount of force that is needed to decouple a locking element from the rest of a locking device can depend on any of a number of different factors. Such factors may include, for example, the thickness of the coupling region, the material or materials that form the coupling region, and/or the location of scoring, perforations, or other weakened points in the coupling region. In some cases, the amount of force that is required to decouple a locking element from the rest of a locking device, as well as the way in which the force is applied to decouple the locking element, may be controlled to prevent damage to the locking element, the tether, the anchors, and/or the surrounding tissue.

While the application of force to decouple a locking element from the rest of a locking device has been described, other decoupling methods may alternatively or additionally be employed. As an example, a locking element may be decoupled by cutting a joint between the locking element and the rest of the device using, for example, a cutter. In some variations, the cutter may be in the form of a shearing blade that slides to shear the joint between the locking element and the rest of the device. In certain variations, a cutter that cuts the connection between a locking element and the rest of a locking device may also be used to cut a tether being secured by the locking device. For example, the cutter may cut both the tether and the joint in a combined manner, thus completely releasing the locking element with the tether severed.

It should be understood that any of the methods and device components described here for actuating a locking device (e.g., threading a tether through the locking device, advancing a plug into a locking member of the locking device, etc.) and/or decoupling one or more components of the locking device from the rest of the locking device may be employed with any of the other locking devices described here, if suitable to do so. Moreover, any suitable variation of a locking device may be included in a tether tensioning device.

It may be necessary, in some instances, to load a tether into a device, such as a tether tensioning device comprising a locking element, a tether tensioning device comprising a cutting element, or a tether tensioning device comprising both a locking element and a cutting element. Various methods and/or devices may be used to accomplish this loading.

Figure 5A:
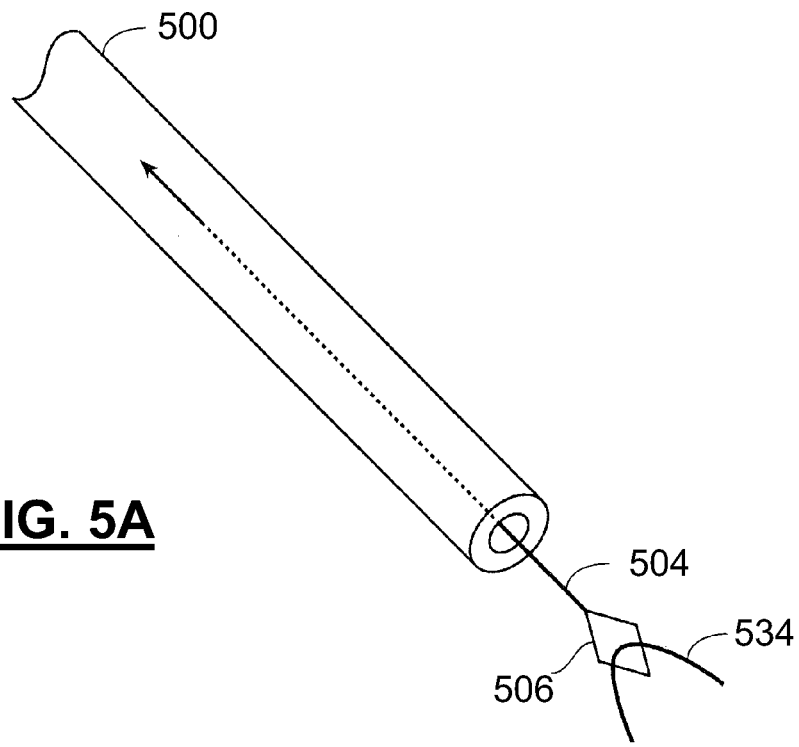
FIGS. 5A and 5B are illustrative variations of devices for loading tethers into devices or device components, such as catheters.
Figure 5B:
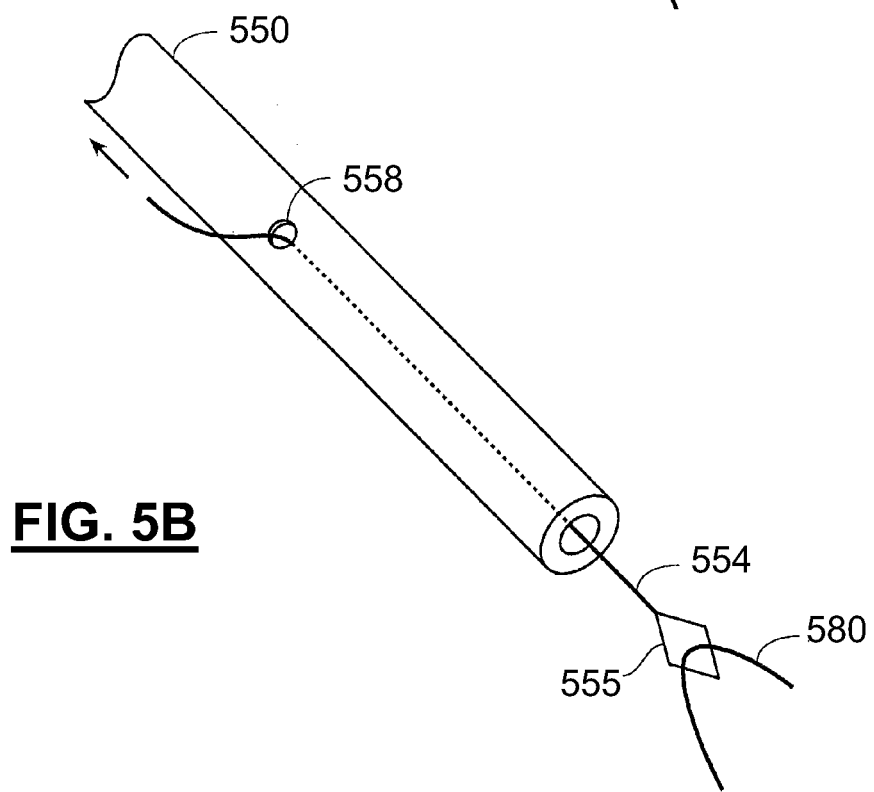

As an example, and referring now to FIGS. 5A and 5B, in some variations, a tether (534) is loaded into a device (500) using a lasso (504) comprising a loop (506) at one end. One end of tether (534) is threaded through loop (506) of lasso (504). Lasso (504) may then be pulled along the longitudinal axis of device (500) (FIG. 5A), to load tether (534) into device (500). In alternative implementations, shown in FIG. 5B, a lasso (554) having a loop (555) may be pulled through a side hole (558) in a device (550) to load a tether (580) into the device. Device (500) or device (550) may be used to perform one or more functions, such as locking and/or cutting. Lassos may be made from, for example, conventional materials such as wire, suture, cable, string, or a monofilament. A lasso may comprise a loop (as show in FIGS. 5A and 5B), a hook, a coil, a tube, an elongate element with a hole, or any other structure or material that can "grab" a tether.

While the use of tether-loading devices to load tethers into locking elements or devices has been described, such tether-loading devices may have other uses, such as to load tethers into cutting elements or devices, or into combination locking and cutting elements or devices. Other uses may also apply. Moreover, any of the features described herein with respect to a locking element or device may also be used, as appropriate, in a cutting element or device, or in a combined locking and cutting element or device.

Figure 6A:
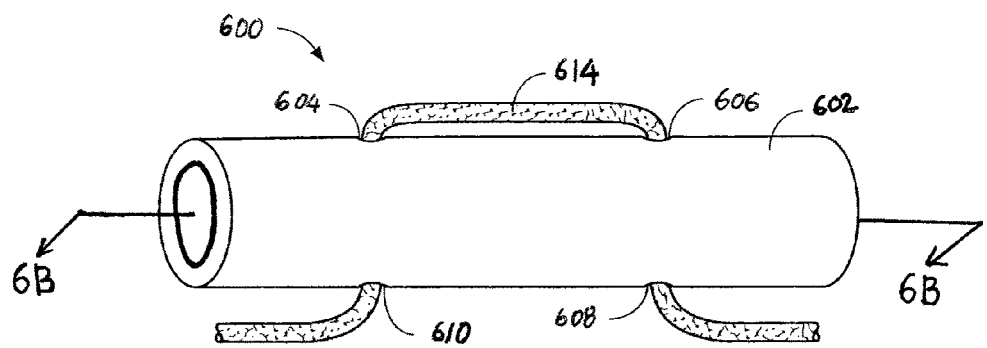
FIG. 6A is a perspective view of a tether-locking catheter.
Figure 6B:
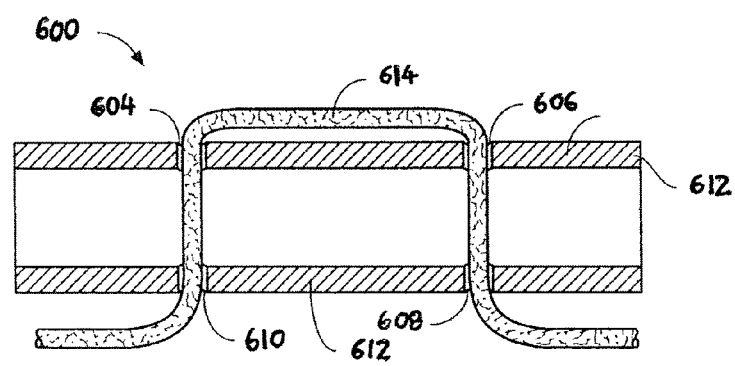
FIG. 6B is a cross-sectional view of the tether-locking catheter of FIG. 6A, taken along line 6B-6B.

Tethers may be routed through a device, such as a locking device or a cutting device, in any of a number of different configurations. For example, FIGS. 6A and 6B show a variation of a locking device (as shown, a locking catheter (600)). Locking catheter (600) includes a tubular member (602) having a wall (612) with four openings (604), (606), (608), and (610) formed in it. A locking catheter such as locking catheter (600) may be used, for example, to maintain tension in a tether, and to stabilize the tether for cutting. In FIGS. 6A and 6B, a tether (614) has been threaded into locking catheter (600), through openings (604), (606), (608), and (610). The tether may be threaded into the locking catheter using, for example, a lasso, such as one of the lassos described above. The lasso may have a relatively flexible loop which may enhance the maneuverability of the lasso through the openings in the locking catheter.

While locking catheter (600) is shown as including four openings through which tether (614) is threaded, locking catheters can include other numbers of openings. For example, some variations of locking catheters may include fewer openings (e.g., two openings), while other variations of locking catheters may include more openings (e.g., six openings, eight openings, etc.). As the number of openings in a locking catheter increases, the likelihood of movement by a tether that is threaded through the openings may decrease.

Figure 7A:
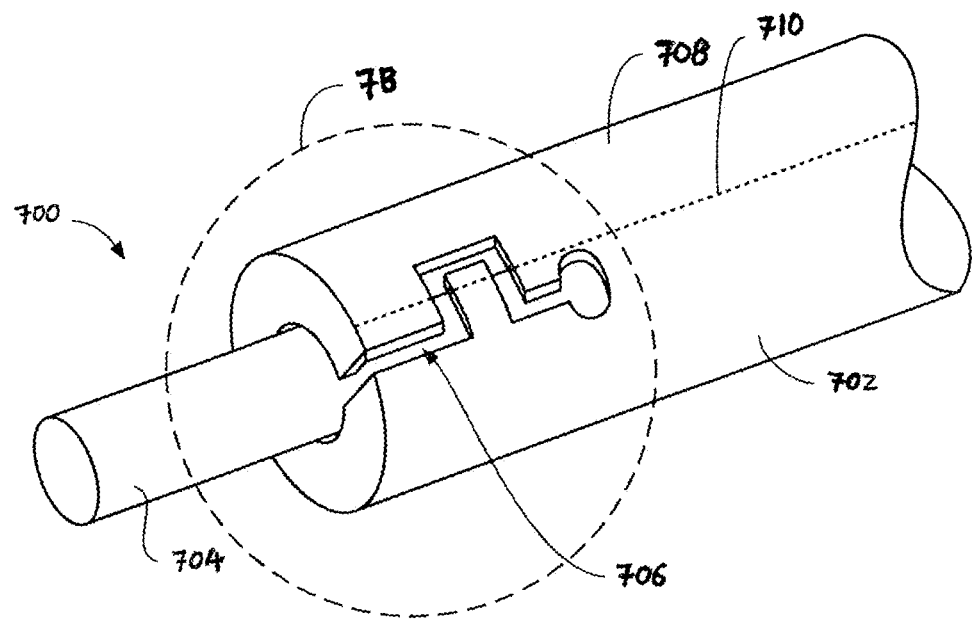
FIG. 7A is a perspective view of a variation of a device that may be used to lock a tether.
Figure 7B:
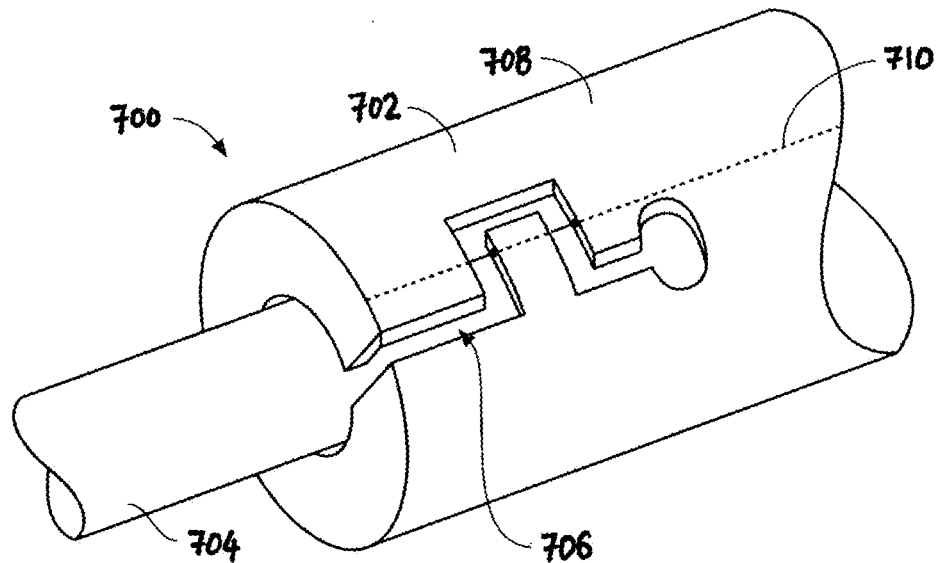
FIG. 7B is an enlarged view of region 7B of FIG. 7A.

An additional example of a locking device is shown in FIGS. 7A and 7B. As shown there, a locking device (700) includes a tubular elongated member (702) that is coupled to a locking element (704). Elongated member (702) has an interlocking feature (706) cut into its wall (708). Interlocking feature (706) is held locked by a coupling line (710) that is routed through the interlocking feature. When coupling line (710) is pulled out, interlocking feature (706) is released, thereby eliminating the hoop strength of elongated member (702). This causes the elongated member to decouple from locking element (704) (e.g., by disengaging from a shoulder feature (not shown) on the locking element). While one coupling line is shown, in some variations, an interlocking feature may be locked and unlocked using multiple (e.g., 2, 3, 4, or 5) coupling lines. In some variations, a tether tensioning device may comprise one or more features (e.g., an outer member) that may be actuated (e.g., using a button slider) to withdraw a coupling line from an interlocking feature of a locking element or device incorporated into the tether tensioning device.

Figure 8A:
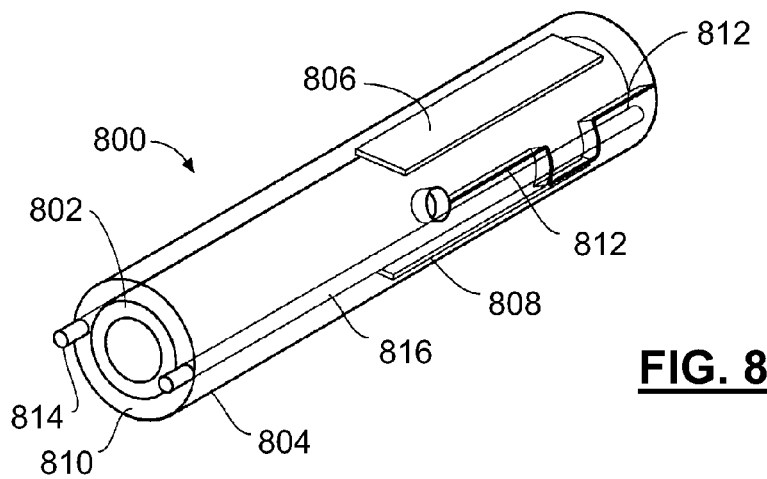
FIG. 8A is a perspective view of a variation of a device that may be used to lock a tether.
Figure 8B:
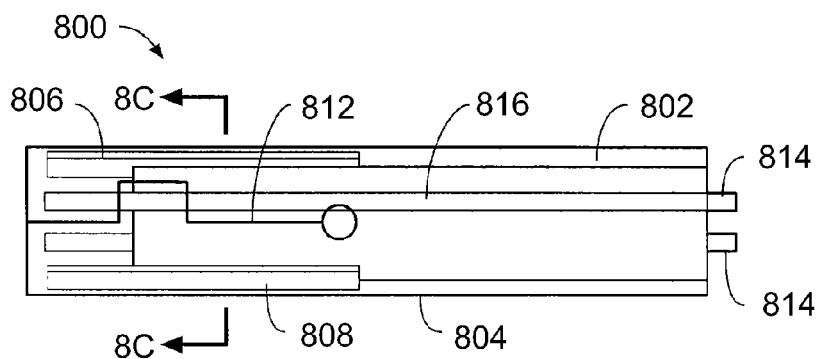
FIG. 8B is a side view of the device of FIG. 8A.
Figure 8C:
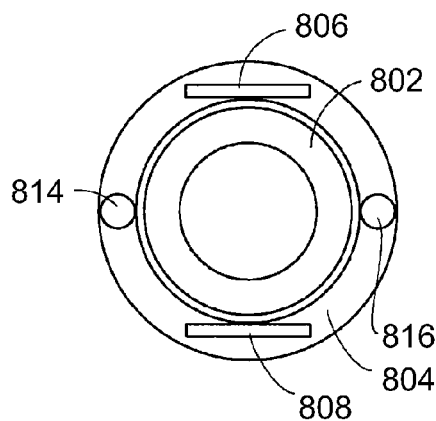
FIG. 8C is a cross-sectional view of the device of FIGS. 8A and 8B, taken along line 8C-8C in FIG. 8B.

FIGS. 8A-8C also show an interlocking feature in a locking device. As shown in FIGS. 8A-8C, a distal portion (800) of a locking device comprises a locking tube (802) disposed within a tubular elongated member (804). While not shown, tubular elongated member (804) may, for example, extend proximally for an additional length to form the rest of the locking device, or may be coupled to another elongated member to form the rest of the locking device. Other configurations may also be used.

As shown in FIGS. 8A-8C, two pieces of Nitinol flat wire (806) and (808) are embedded within the wall (810) of elongated member (804) to provide the elongated member with enhanced rigidity. While Nitinol has been described, other materials may be used. Moreover, in some variations, the locking device may not include flat wire, or may include only one piece of flat wire or more than two pieces of flat wire.

Elongated member (804) includes two interlocking features in its wall (810). While FIGS. 8A-8C only show one interlocking feature (812), a corresponding interlocking feature is located on the other side of the elongated member. However, some variations of locking devices may include only one interlocking feature, or may include multiple interlocking features having different configurations.

The interlocking features in elongated member (804) are comprised of slits that are cut into wall (810), although different types of interlocking features are possible. For example, an interlocking feature may be formed of a combination of polygonal openings. As shown in FIGS. 8A and 8B, the portions of wall (810) on either side of the slits are held together (and thereby kept in a locked configuration) by two wires (814) and (816) that extend through lumens within wall (810). The use of wires that extend through lumens in the wall of elongated member (804) may allow the elongated member to maintain a relatively low profile. While wires have been described, any other suitable coupling lines (e.g., cables, threads, sutures, tethers, etc.) may be used. Moreover, certain variations of devices may comprise only one coupling line, or multiple (e.g., 2, 3, 4, 5) coupling lines. In device variations comprising multiple coupling lines, the coupling lines may be the same type of coupling line, or may be different from each other. For example, a device may include one coupling line in the form of a wire, and a second coupling line in the form of a suture.

Locking tube (802) may be decoupled from elongated member (804) by withdrawing wires (814) and (816) (e.g., using button sliders on the handle of the locking device) and thereby unlocking the interlocking features. In some cases, this unlocking alone may be sufficient to release the locking tube from the elongated member. In other cases, additional assistance (e.g., pushing the locking tube with a pushing member) may be required to release the locking tube from the elongated member.

Figure 9A:
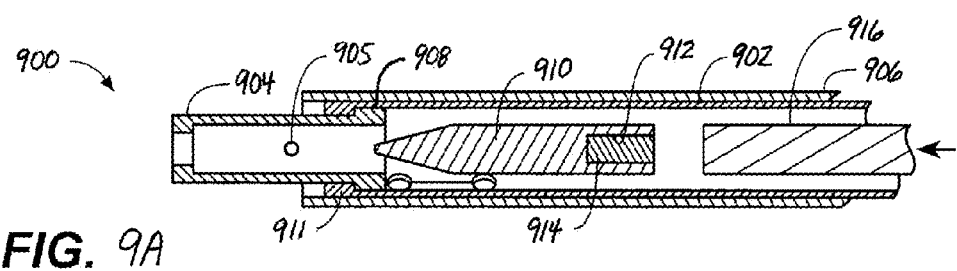
FIGS. 9A-9D show a variation of a device for locking a tether.

FIGS. 9A-9D illustrate a method of locking a tether using another variation of a locking device. Referring first to FIG. 9A, a locking device (900) includes a coupling tube (902) having a distal portion that is coupled to a locking element (904). As shown, locking element (904) is in the form of a locking tube having an opening (905) configured for passage of a tether therethrough. While a locking tube is shown, other suitable configurations may be used for a locking element. Locking element (904) can be formed of one or more metals, metal alloys, and/or polymers. As an example, in some variations, locking element (904) is formed of a nylon and bismuth trioxide composite, and includes a layer of PEBAX® polymer.

A sheath (906) surrounds coupling tube (902), as well as a portion of locking element (904). However, in some variations, a sheath may cover the entirety of a locking element, and may even extend distally beyond the locking element. Moreover, in certain variations, a sheath may surround only a portion of a coupling tube. Sheath (906) helps to couple coupling tube (902) to locking element (904) by compressing the coupling tube to the locking element. Additionally, locking element (904) includes a shoulder (908), and coupling tube (902) is configured to latch onto shoulder (908) when sheath (906) compresses coupling tube (902) to locking element (904). As shown, coupling tube (902) comprises a shoulder (911) that latches to shoulder (908). While shoulders (908) and (911) are shown as generally angular, in some variations, a locking element shoulder and/or a coupling tube shoulder may be ramp-shaped, or may have any other suitable shape. A ramp-shaped coupling tube shoulder may, for example, provide for relatively easy decoupling of the coupling tube from the locking element when such decoupling is desired.

Locking device (900) is configured such that if sheath (906) is proximally retracted, locking element (904) is decoupled from coupling tube (902). However, in certain variations, a sheath may be proximally retracted, while a coupling tube and locking element are distally pushed upon, in order to decouple the locking element from the coupling tube. Alternatively or additionally, the coupling element and locking tube may be distally pushed upon before and/or after the sheath is proximally retracted. Any other suitable methods for decoupling the locking element from the coupling tube may also be employed.

As shown in FIG. 9A, a plug (910) is disposed within coupling tube (902), and has a generally missile-shaped configuration, although other appropriate configurations (e.g., a cylindrical plug, a plug having a hexagonal cross-section, etc.) may also be used. The plug can be formed of any appropriate material or materials, such as one or more polymers, and may in some variations be relatively rigid. In certain variations, plug (910) is formed of a nylon and bismuth trioxide composite. As shown in FIG. 9A, plug (910) includes a bore (912) containing a radiopaque marker (914). This can allow for ready viewing of the plug via X-ray fluoroscopy. A pushing member (916) is also disposed within coupling tube (902), and may be used to push plug (910) into locking element (904).

Figure 9B:
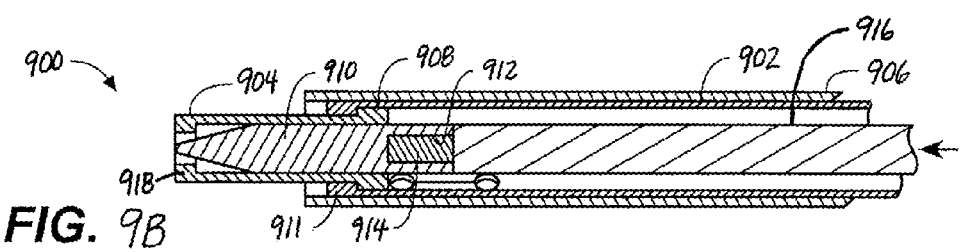

During use of locking device (900), a tether (not shown) may be threaded through locking element (904) and coupling tube (902). Any appropriate method may be used to thread the tether including, for example, one or more of the methods described above. As an example, a lasso may be used to capture the distal end of the tether, and to thread the tether first through opening (905), and then through coupling tube (902). In some methods, the locking device may be advanced along the tether to a desired position. As shown in FIG. 9B, once the tether has been threaded through locking element (904) and coupling tube (902), pushing member (916) may be advanced toward the distal end of the locking device. This advancement of pushing member (916) pushes plug (910) into locking element (904), compressing the tether between plug (910) and the inner walls of locking element (904). Because coupling tube (902) engages shoulder (908) of locking element (904), a resistive force is provided during plug advancement. This resistive force may help to limit the likelihood of locking element (904) becoming prematurely decoupled from coupling tube (902), as a result of the advancement of pushing member (916). A step (918) at the distal end of the locking element prevents the plug from exiting the locking element.

Figure 9C:
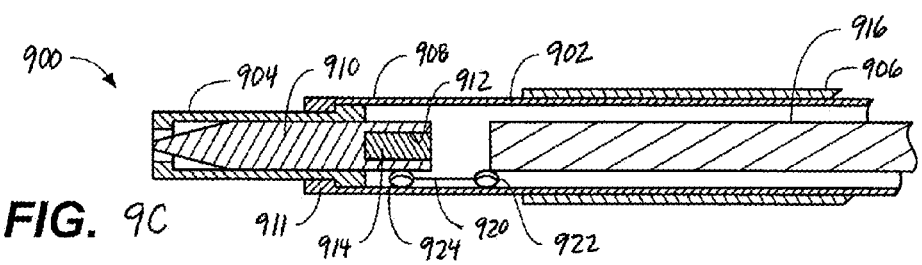

Referring now to FIG. 9C, after plug (910) has been pushed into locking element (904), sheath (906) may be proximally retracted. Prior to being proximally retracted, sheath (906) compresses coupling tube (902) to locking element (904), thereby engaging coupling tube (902) with the shoulder (908) of locking element (904) and coupling the coupling tube to the locking element. However, once sheath (906) has been proximally retracted, this compressing force is no longer present. Coupling tube (902) is configured such that in the absence of this compressing force, coupling tube (902) no longer forms a tight fit around locking element (904). Rather, the removal of the compressing force allows coupling tube (902) to assume a more relaxed configuration, essentially opening up and thereby disengaging coupling tube (902) from shoulder (908) of locking element (904). As a result, coupling tube (902) and locking element (904) are decoupled from each other. This assumption of a more relaxed configuration by coupling tube (902) is enhanced by the presence of a slit (920) in the distal portion of the coupling tube, as well as two openings (922) and (924) along the slit that provide stress relief. While not shown, in some variations, a coupling tube may include more than one slit in its distal portion. Moreover, while openings (922) and (924) are circular, in certain variations, a coupling tube may alternatively or additionally include one or more non-circular (e.g., rectangular, triangular, etc.) openings.

Figure 9D:
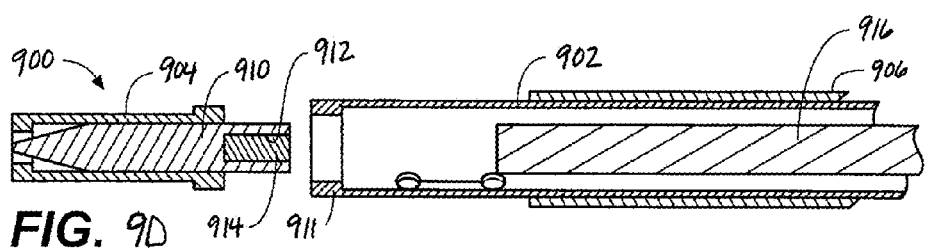

Referring finally to FIG. 9D, and as discussed above, the proximal retraction of sheath (906) causes locking element (904) to be released from coupling tube (902). Plug (910), which was previously pushed into locking element (904), is released along with locking element (904). The locking element and plug, now separated from the other elements of the locking device, remain within the body, securing the tether, while the other elements of the locking device are removed from the body. In this way, sheath (906) can function as a safety mechanism, preventing locking element (904) from being released prematurely, and providing the operator with enhanced control over the release of locking element (904).

Although only a few of the ways in which a locking element may be releasably coupled to a device have been described, it should be understood that any appropriate coupling may be used, including snap fits and other coupling mechanisms (e.g., threads, etc.). Additionally, the couplings described herein may be readily scaled in size for use even with applications that may require very small locking elements (e.g., for use in percutaneous applications and/or certain surgical applications, such as microsurgical applications). Locking elements that are releasably coupled to devices are described, for example, in U.S. Patent Application Publication No. US 2008/0172035 A1, which was previously incorporated by reference in its entirety. Additional examples of locking devices are described, for example, in U.S. patent application Ser. No. 12/480,568, filed on Jun. 8, 2009, which is hereby incorporated by reference in its entirety.

Figure 18A:
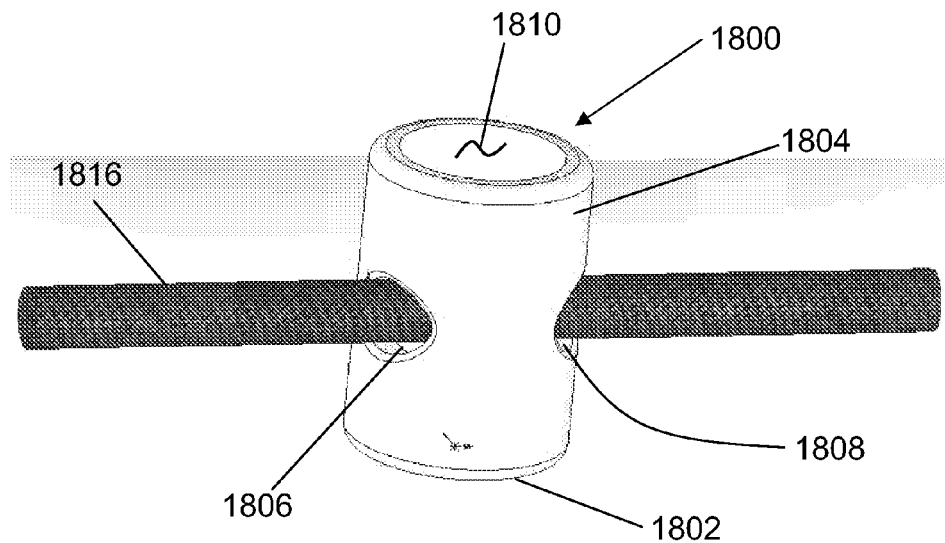
FIGS. 18A-18H depict variations of a device and method for locking a tether.
Figure 18B:
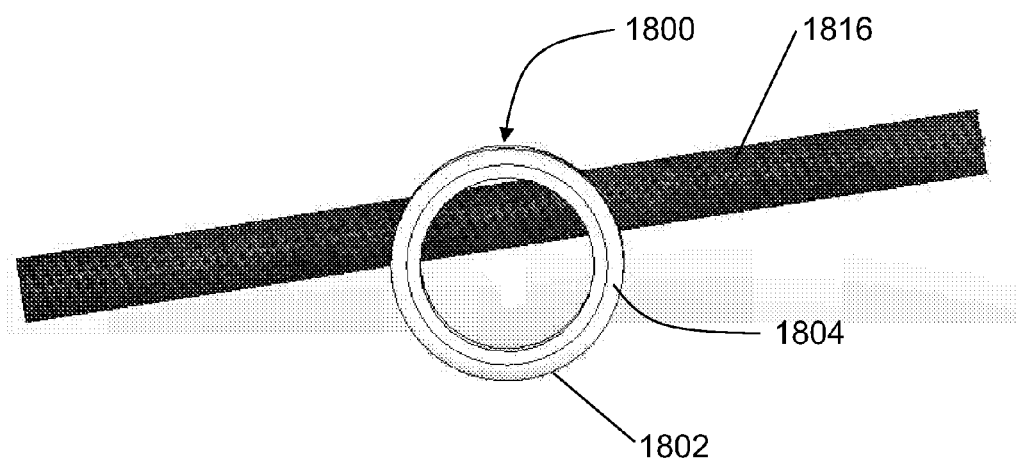
Figure 18C:
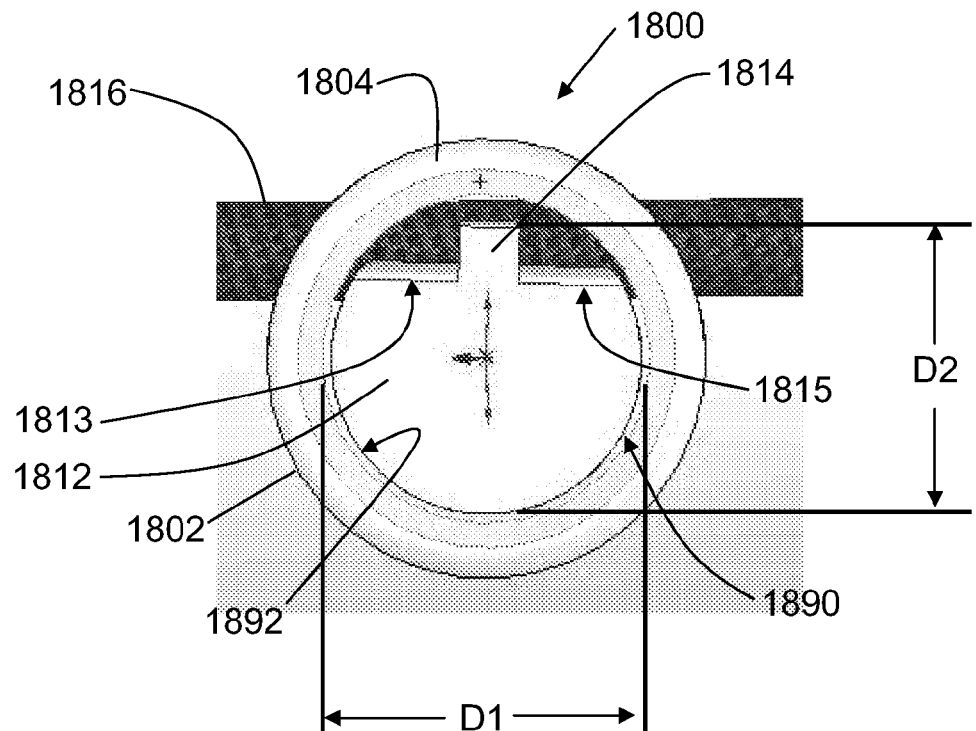

Still other variations of locking elements may be used. For example, in some variations, a locking element may comprise a hollow locking member and a rotatable plug configured to rotate within the hollow locking member. As an example, FIGS. 18A-18C show a locking element (1800) comprising a locking tube (1802) comprising a wall portion (1804) with two apertures (1806) and (1808) therethrough. Locking tube (1802) has a lumen (1810), within which is disposed a rotatable plug (1812) (shown in FIG. 18C, while FIGS. 18A and 18B depict the locking element without the rotatable plug). Plug (1812) has a protrusion (1814) located between two flat surfaces (1813) and (1815). In some variations, protrusion (1814) may protrude from flat surfaces (1813) and (1815) by a distance of 0.003 inch to 0.005 inch. As shown in FIG. 18C, plug (1812) has a dimension (D1) and a dimension (D2) that is smaller than dimension (D1). With the exception of the portion of plug (1812) comprising protrusion (1814) and flat surfaces (1813) and (1815), the remainder of plug (1812) is generally cylindrical in shape. However, any other suitable rotatable plug configurations may be used. When plug (1812) is disposed within lumen (1810) and a tether (1816) is threaded through apertures (1806) and (1808), thereby crossing the lumen, protrusion (1814) contacts the tether.

Figure 18D:
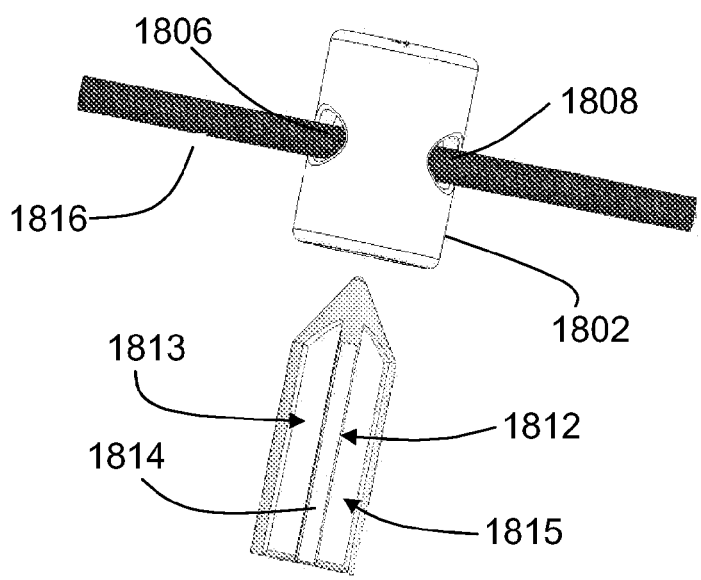
Figure 18E:
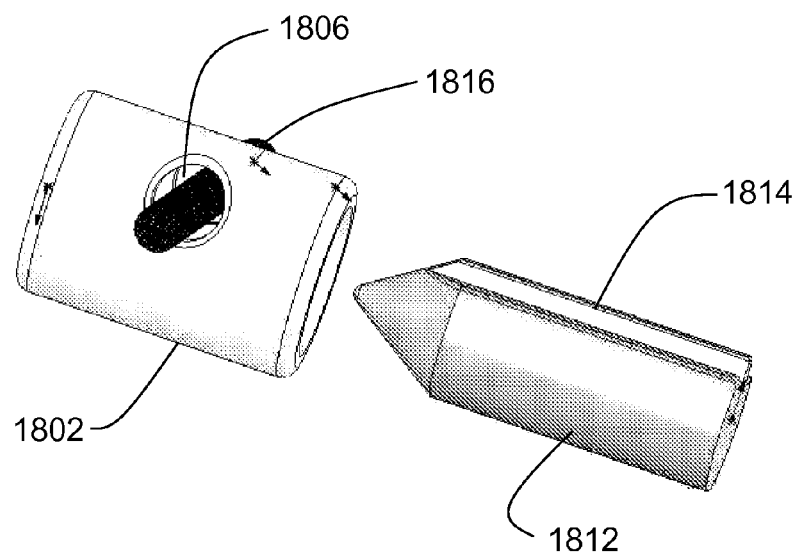

Referring now to FIGS. 18D and 18E, plug (1812) may, in some variations, be a separate component from locking tube (1802). Alternatively, a plug may be coupled to a locking member during manufacturing, or may be integrally formed with the locking member. As shown in FIGS. 18D and 18E, tether (1816) may be threaded through apertures (1806) and (1808) in wall portion (1804) when the plug is not yet disposed within the lumen of the locking tube. Of course, in certain variations, a tether may be threaded through the apertures during and/or after advancement of the plug into the locking tube. As shown, the tether crosses the lumen of the locking tube such that the tether is off-center with respect to the lumen. However, in some variations, the apertures may be positioned so that a tether passing through them crosses the center of the lumen.

Figure 18F:
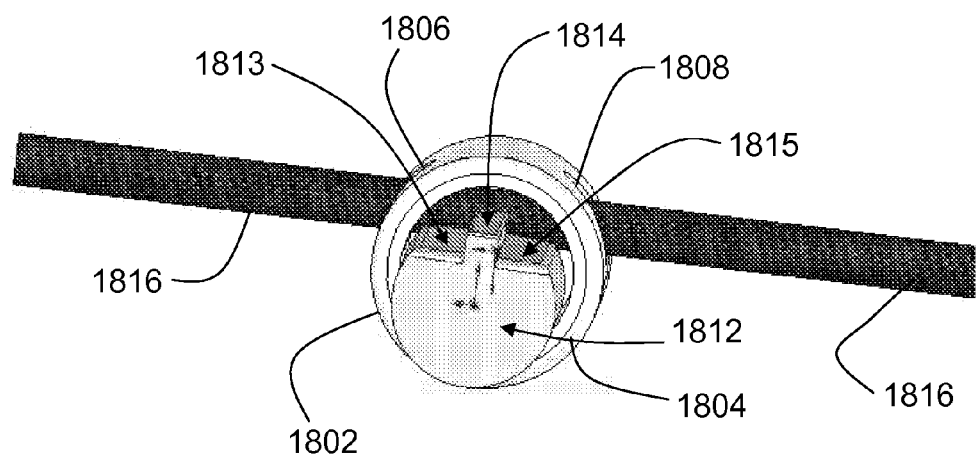
Figure 18G:
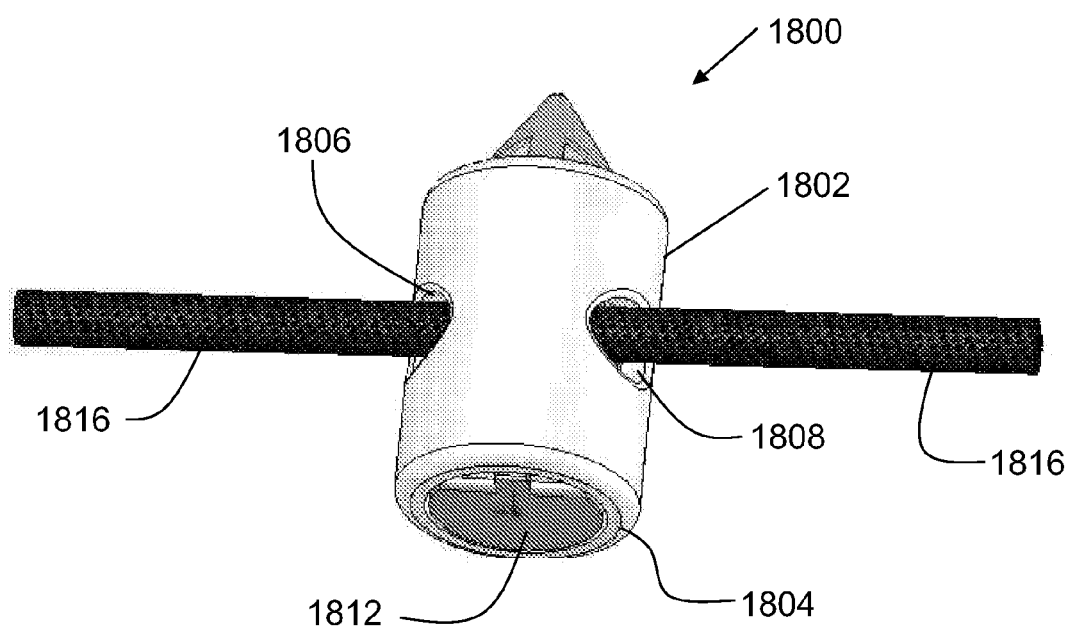
Figure 18H:
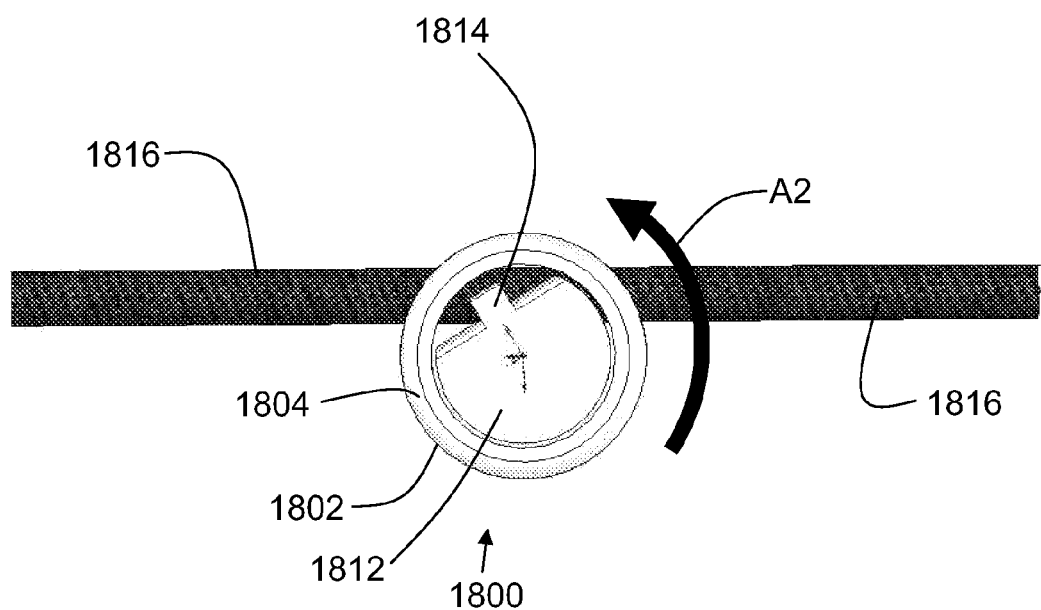

As shown in FIG. 18F, after tether (1816) has been threaded through apertures (1806) and (1808) in locking tube (1802), plug (1812) may be advanced into the lumen of the locking tube (e.g., using a pushing member), such that protrusion (1814) on plug (1812) contacts the tether. Typically, this advancement of the plug into the locking tube may take place at least partially within a sheath or other elongated member that may later be withdrawn or otherwise removed from the plug and the locking tube. When the plug is fitted into the locking tube such that the protrusion contacts the tether, the contact between the protrusion and the tether provides friction that helps to hold the plug and the tether in place with respect to each other (i.e., minimizing relative motion between the plug and the tether). FIG. 18G shows plug (1812) when it is disposed within locking tube (1802). Referring back to FIG. 18C, which also shows the plug disposed within the locking tube, plug (1812) has an exterior surface (1890) with a curvature alignable with an interior surface (1892) of the locking tube. Referring now to FIG. 18H, tether (1816) may be tensioned, thereby causing the plug to rotate within the lumen of the locking tube (e.g., in the direction of arrow A2) because of the contact between the tether and the protrusion on the plug. The tensioning of the tether will generally cause the plug to rotate toward the direction in which the tether is being tensioned. This rotation may, in turn, result in more contact between the plug and the tether, such that the tether may become further secured. In some variations, plug (1812) may be rotated by at least about 1° (e.g., at least about 10°, at least about 20°, at least about 45°, at least about 90°, at least about 135°) and/or at most about 180° (e.g., at most about 135°, at most about 90°, at most about 45°, at most about 20°, at most about 10°).

In some variations, a relatively low plug force may be used to plug locking tube (1802) with plug (1812). Even though a relatively low plug force may be used, the resulting lock force may be relatively high. Thus, in certain variations, a tether may be locked very securely by applying minimal force to a locking element that locks the tether.

Figure 18I:
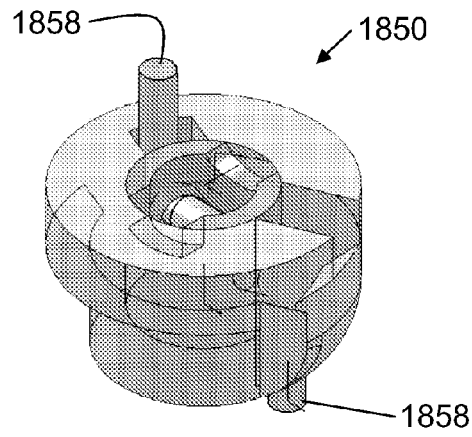
FIGS. 18I-18P show variations of components of devices for locking a tether.
Figure 18J:
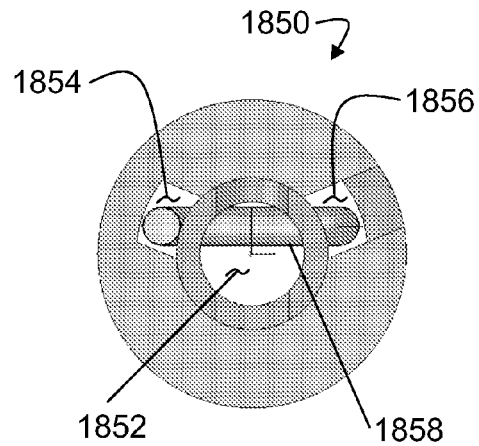
Figure 18K:
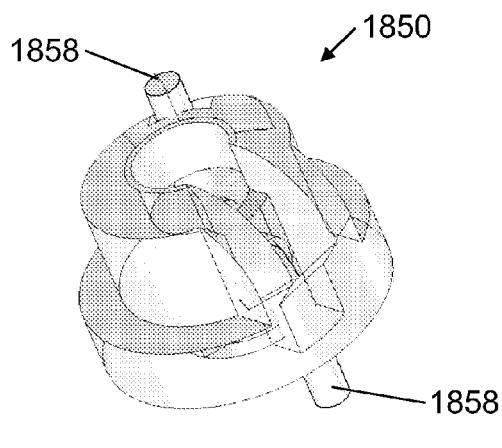
Figure 18L:
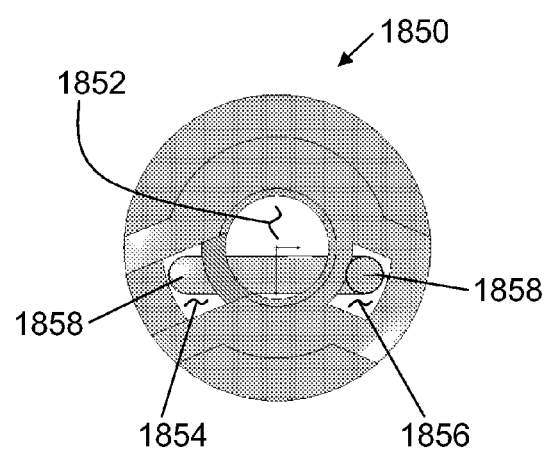
Figure 18M:
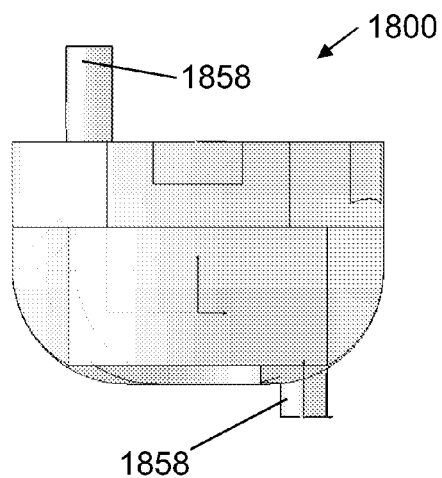
Figure 18N:
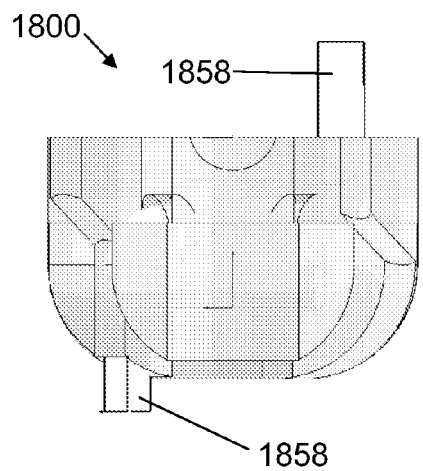

Other variations of plugs and/or locking members may also be used. As an example, FIGS. 18I-18N show different views of another variation of a locking member configured to receive a plug (e.g., a rotatable plug) to secure a tether therebetween. FIG. 18I shows a bottom angled perspective view of the locking member (1850), while FIG. 18J shows a bottom view of locking member (1850), FIG. 18K shows a top angled perspective view of locking member (1850), FIG. 18L shows a top view of locking member (1850), FIG. 18M shows a front view of locking member (1850), and FIG. 18N shows a back view of locking member (1850). As most clearly shown in FIGS. 18J and 18L, locking member (1850) has a lumen (1852) configured to receive a plug, as well as two apertures (1854) and (1856) configured for passage of a tether (1858) therethrough. The configuration of locking member (1850) may, for example, provide for relatively controlled tether routing through the locking member. This, in turn, may help to control the way in which locking member (1850) lies against body tissue and/or one or more anchors during use.

Figure 18O:
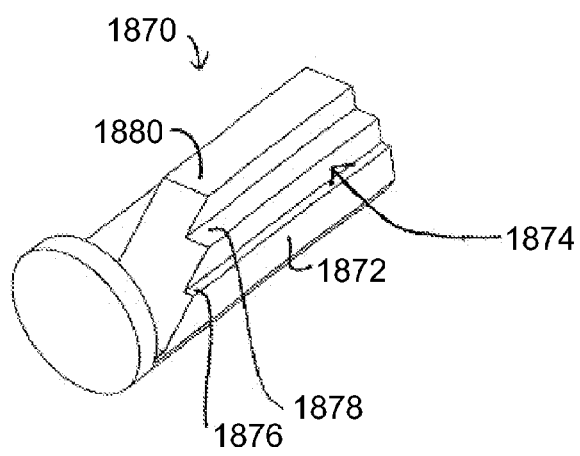
Figure 18P:
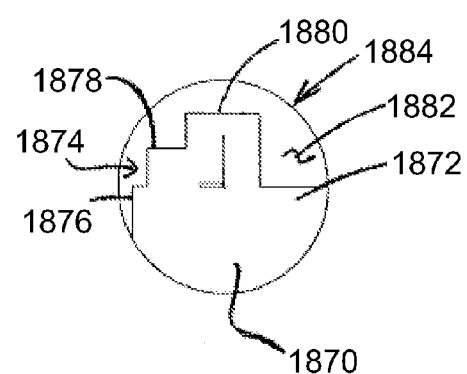

FIGS. 18O and 18P show another variation of a plug that may be used to secure a tether. In some variations, the plug may be rotatable (e.g., within a lumen of a locking tube). As shown in FIGS. 18O and 18P, a plug (1870) comprises a body (1872) and a plurality of protrusions (as shown, three protrusions, although a greater or lesser number of protrusions may also be used) in the form of a stepped configuration (1874) extending from the body. The radial length for each protrusion (1876), (1878), and (1880) is longer than the previous protrusion. During use, plug (1870) may be fitted into a lumen (1882) of a locking tube (1884) (FIG. 18P) or other locking member (e.g., by advancing the plug into the lumen with a pushing member). As the plug is rotated, the progressively longer protrusions may contact a tether crossing the lumen, and may secure the tether within the lumen. Other configurations may also be used. For example, in some variations, a rotatable plug may comprise a gear-shaped portion comprising a plurality of teeth of different lengths (e.g., with each tooth progressively longer than the previous tooth).

In certain variations, a locking element may lock a tether using one or more methods that are different from those described above. The method or methods may be used in addition to, or as an alternative to, tensioning a tether to rotate a rotatable plug and thereby lock the tether.

Figure 18Q:
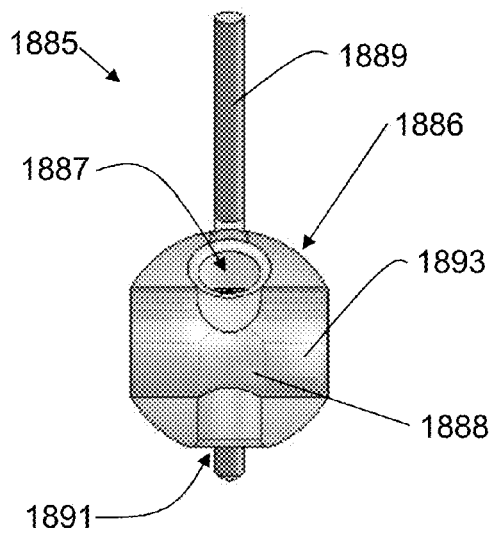
FIGS. 18Q-18X depict additional variations of a device and method for locking a tether.
Figure 18R:
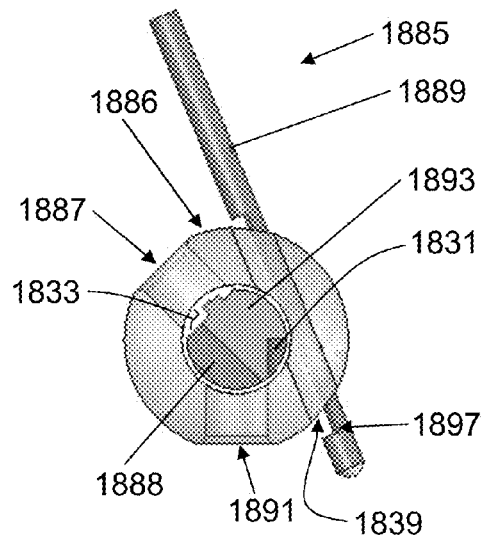
Figure 18S:
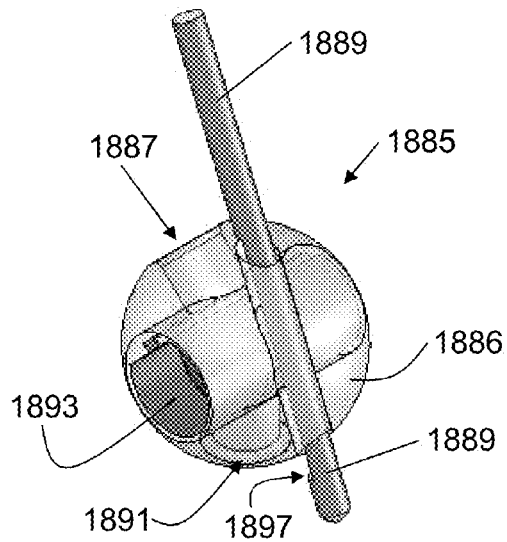
Figure 18T:
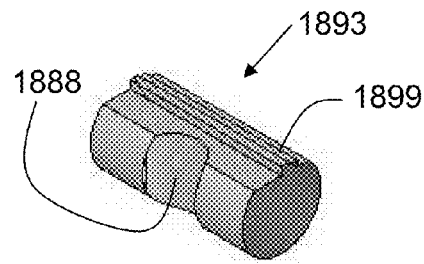
Figure 18U:
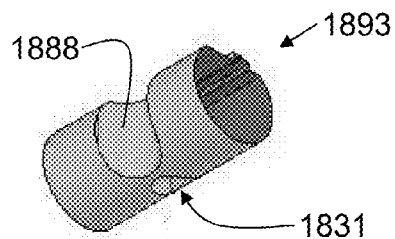
Figure 18V:
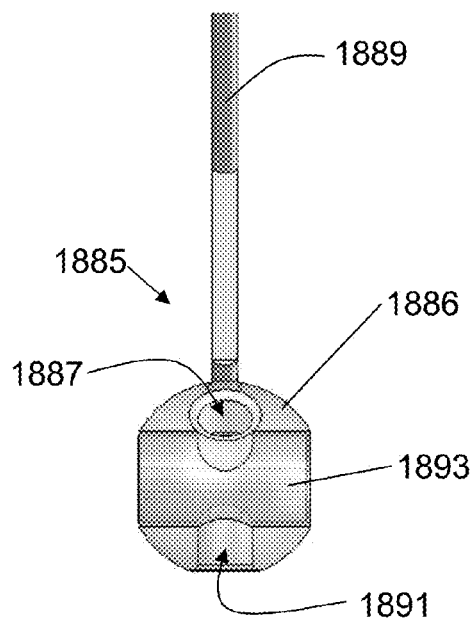
Figure 18W:
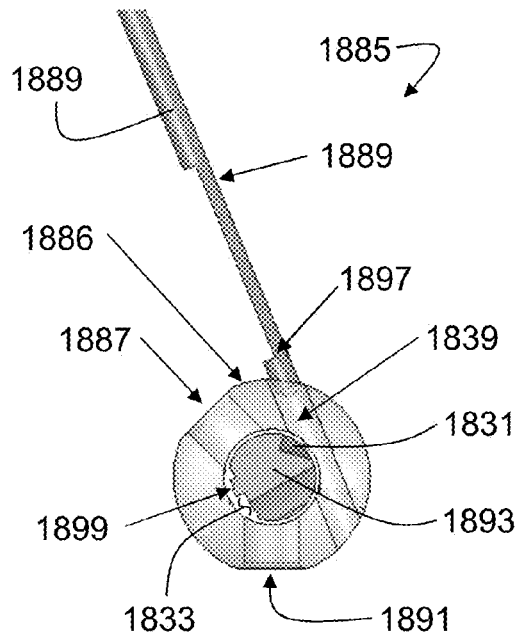
Figure 18X:
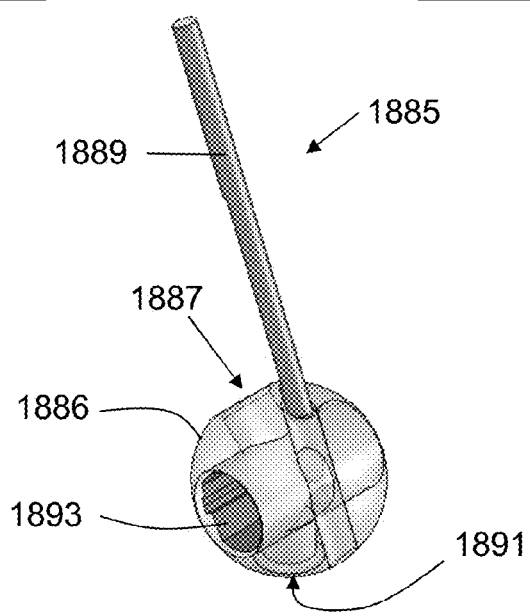

For example, FIGS. 18Q-18X show a variation of a locking element comprising a rotatable plug, where the locking element uses a pullwire mechanism to lock a tether. As shown there, a locking element (1885) comprises a generally spherical locking member (1886), a rotatable plug or cam (1893) disposed within a lumen (1833) of locking member (1886), and a pullwire (1889) passing through a channel (1839) in locking member (1886) (FIG. 18R). FIGS. 18Q-18S depict locking device (1885) in its unlocked or open position, and FIGS. 18V-18X depict locking device (1885) in its locked or closed position.

In use, plug (1893) may be advanced into lumen (1833) of locking member (1886), and a tether (not shown) may be routed through the locking member when the locking member is in its unlocked position. It should be noted that in some variations, a locking element may comprise a locking member and a rotatable plug that are preassembled. Locking member (1886) includes two apertures (1887) and (1891) configured for passage of a tether therethrough, and plug (1893) also has a slot (1888) configured for passage of a tether when the locking element is in its unlocked position.

After a tether has been routed through locking element (1885), pullwire (1889) may be actuated (e.g., by pulling on the pullwire) to transition locking element (1885) into its locked position. Plug (1893) includes a notch (1831) (FIG. 18U) configured to interface with a notch (1897) (FIGS. 18R, 18S, and 18W) on pullwire (1889). More specifically, when pullwire (1889) is actuated, notch (1897) on pullwire (1889) engages notch (1831) on plug (1893), thereby causing plug (1893) to rotate. The rotation of the plug helps to secure the tether. Additionally, plug (1893) includes steps (1899) configured to engage the tether as the plug is rotated, thereby helping to lock the tether in place. Other suitable devices and methods for locking a tether using a rotatable plug, and/or using any other suitable mechanism, may alternatively or additionally be employed, as appropriate. Tether-locking devices are described, for example, in U.S. Patent Application Publication Nos. US 2006/190030 A1 and US 2006/0122633 A1, U.S. patent application Ser. No. 12/480,568, filed on Jun. 8, 2009, and U.S. Provisional Application No. 61/104,681, filed on Oct. 10, 2009, all of which were previously incorporated by reference in their entirety.

As described above, in operation, a locking element may be secured to a tether to fix the length of the tether and/or to prevent the tether from moving. After the tether has been locked, any excess length of the tether may be cut and removed. In some variations in which a detachable locking element is used, a tether may be cut to remove excess material either before or after detaching the locking element from the rest of the device. Generally, the tether is cut proximal to the locking mechanism. In many cases, it may be desirable to cut the tether as closely as possible to the locking mechanism, while leaving enough excess length to allow for any slippage that may occur.

In certain variations, a tether may be tensioned prior to being cut. The tensioning may or may not provide a cinching effect. In some cases, the tensioning may make a portion of the tether easier to cut. In certain variations, a single device may be used to both tension and cut a tether, while in other variations, one device may be used to tension a tether and a different device may be used to cut the tether. In some variations, different devices may be used for each of the following functions: the tensioning of a tether, locking of the tether, and cutting of the tether. In other variations, one device may be used to perform at least two of the above functions, and a single device may perform all three of the functions.

Figure 10A:
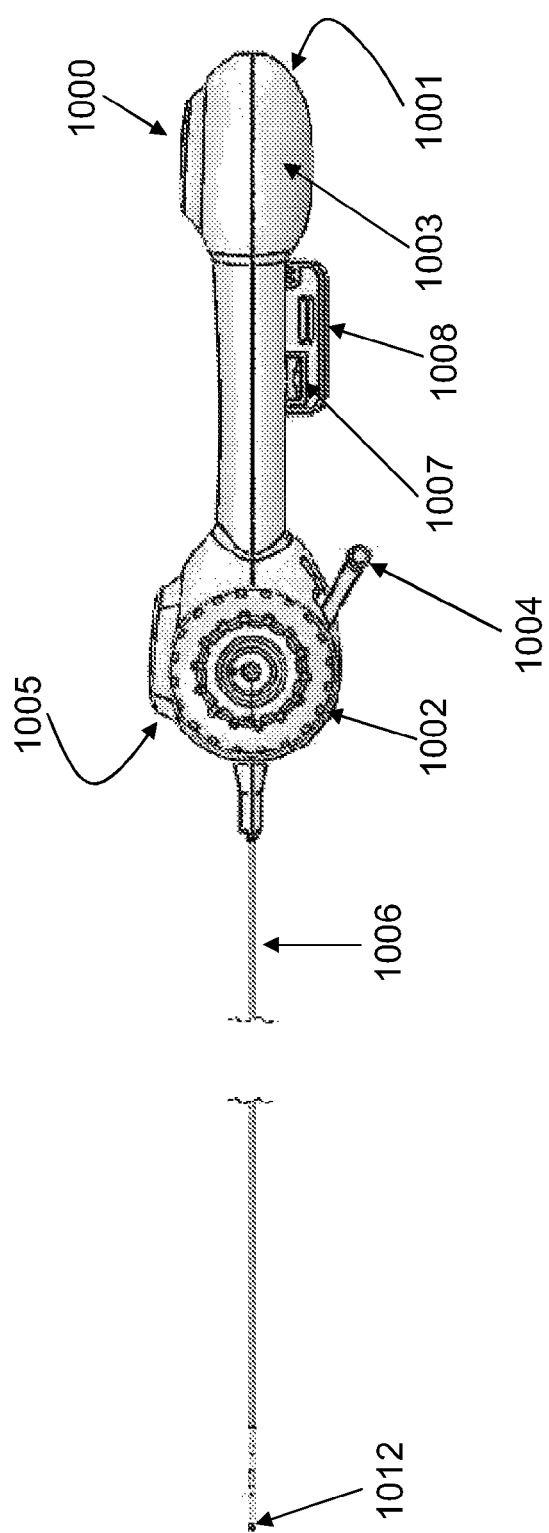
FIG. 10A is a side perspective view of a variation of a device for tensioning and/or cutting a tether.
Figure 10B:
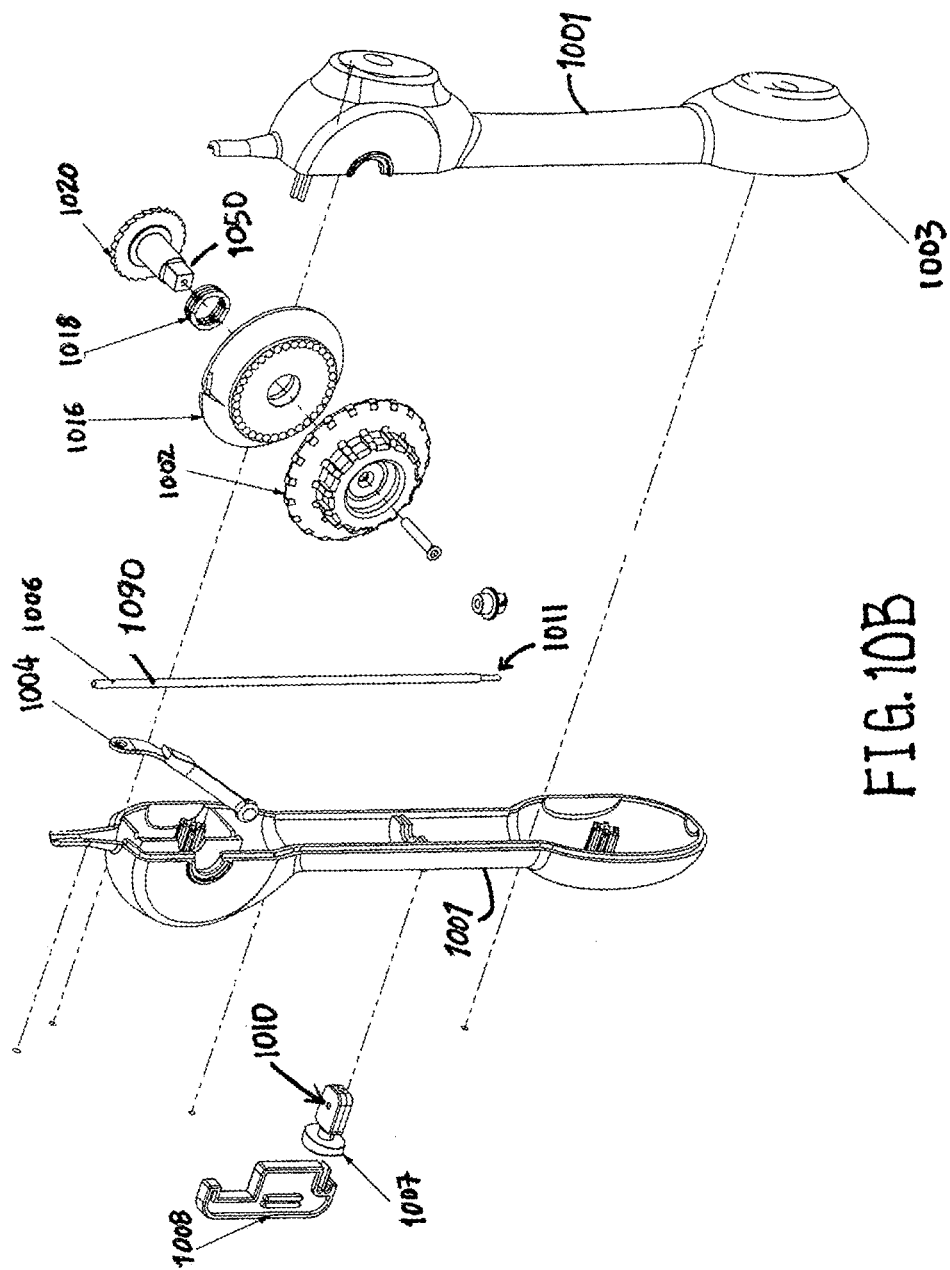
FIG. 10B is an exploded view of a handle portion of the device of FIG. 10A.

FIGS. 10A and 10B show a variation of a tether tensioning device (1000) that may also be used to cut a tether. As shown there, tether tensioning device (1000) comprises a handle portion (1001) coupled to an elongated member (1006). Elongated member (1006) comprises an inner member (1011) at least partially disposed within a lumen of an outer member (1090), and may, for example, be in the form of a catheter. Handle portion (1001) comprises a housing (1003), a rotatable tensioning member (1005) coupled to housing (1003), and a button slider (1007) and retainer (1008) disposed within a slot (not shown) in housing (1003). Tether tensioning device (1000) further comprises a cutting element (1012) in a distal portion of elongated member (1006). For tensioning a tether, rotatable tensioning member (1005) functions in the same way as rotatable tensioning member (205) of tether tensioning device (200) above.

Rotatable tensioning member (1005) comprises a tensioning wheel (1002), a bobbin (1016), a compression spring (1018), and a gear (1020). Rotatable tensioning member (1005) is configured to apply tension to a tether that is engaged to bobbin (1016). Tensioning wheel (1002) and gear (1020) may be coupled together in a variety of ways. As shown here, gear (1020) may comprise a rectangular protrusion (1050) that couples to a corresponding indentation (not shown) in tensioning wheel (1002). Alternatively or additionally, a gear and tensioning wheel may be coupled by one or more screws, or may even be manufactured as one continuous piece. Compression spring (1018) seats tensioning wheel (1002) and bobbin (1016) together so that tensioning wheel (1002) and bobbin (1016) can rotate in unison. When the tension on the tether generates a torque force that exceeds the force generated by compression spring (1018), then tensioning wheel (1002) and bobbin (1016) may disengage, such that the tether may not be further tensioned using tether tensioning device (1000).

Compression springs having varying levels of stiffness may be used to vary the upper bound of tension that may be applied to a tether being tensioned by tether tensioning device (1000). As an alternative to using a compression spring or in addition to using a compression spring, one or more high-friction elements may be used to couple a tensioning wheel and a bobbin. The coefficient of friction of the material or materials of the high-friction elements may determine the upper bound of tension that can be applied to the tether.

In certain variations, a tether tensioning device (e.g., comprising one or more locking and/or cutting elements, or not comprising any locking or cutting elements) may not comprise a mechanism that prevents over-tensioning of the tether. Moreover, in some variations, a tether tensioning device may not comprise a rotatable tensioning member. In certain variations, a tether tensioning device may comprise a lever-arm, and/or a slidable and/or depressible button, that may expand previously compressed members to adjust the tension on the tether. The tensioning device may comprise the lever-arm and/or slidable and/or depressible button either as an alternative to, or in addition to, a rotatable tensioning member. Other expanding mechanisms may alternatively or additionally be used, as appropriate.

Tensioning wheel (1002), bobbin (1016), and/or gear (1020) may be made of any suitable material, such as polycarbonate and/or ABS. The tensioning wheel, bobbin, and/or gear may be made one or more of the same materials, or may all be made of different materials. Compression spring (1018) may be made of any suitably stiff material or materials, such as stainless steel and/or cobalt-chromium.

Release lever (1004) is seated in a double-notched aperture in housing (1003) of handle portion (1001). When in one notch, the release lever allows bidirectional continuous rotation of tensioning wheel (1002). However, when in the other notch, the release lever allows only unidirectional discrete rotation of tensioning wheel (1002). In certain variations, a release lever may not protrude from a handle portion housing, and/or may be located internally of a tether tensioning device (e.g., actuated by a button or slider).

As described above, button slider (1007) is disposed within a slot (not shown) in housing (1003) of handle portion (1001). Button slider (1007) has an aperture (1010) therethrough. The diameter of aperture (1010) may be selected to allow aperture (1010) to receive inner member (1011) of elongated member (1006). The inner member may form a friction fit with the aperture, such that movement of button slider (1007) within the slot results in corresponding movement of inner member (1011). In certain variations, the inner member may be further coupled to button slider (1007) (e.g., using one or more adhesives, and/or by applying heat to fuse the inner member to the button slider). Inner member (1011) may be coupled to cutting element (1012), and may be used to actuate the cutting element to cut a tether. Examples of cutting elements are further described below.

Figure 10C:
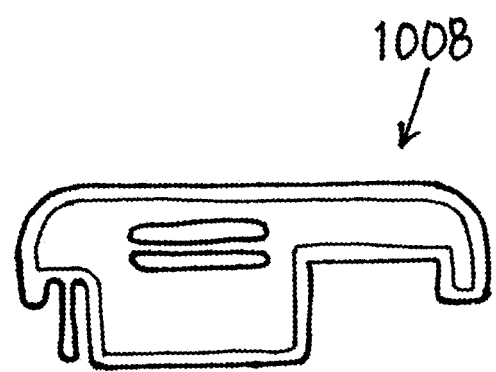
FIG. 10C is a side view of a retainer of the handle portion of FIG. 10B.

FIG. 10C shows retainer (1008) in enlarged detail. Retainer (1008) is configured to immobilize button slider (1007) when retainer (1008) is disposed within the same slot as the button slider. This immobilization may help to prevent unintentional button slider movement. Retainer (1008) may be any suitable shape or size that substantially blocks the movement of the button slider. The retainer may be made of any suitable material or materials, such as polymers (e.g., polycarbonate, ABS). In certain variations, retainer (1008) may be internal to tether tensioning device (1000), and may be actuated by a button or slider on an external surface of the tether tensioning device. In some variations, retainer (1008) may be engaged to tether tensioning device (1000) by a tether and/or a snap closure. Other suitable engagement mechanisms may alternatively or additionally be used. Moreover, a retainer may have one or more other features (e.g., color-coding), as discussed above.

Figure 11A:
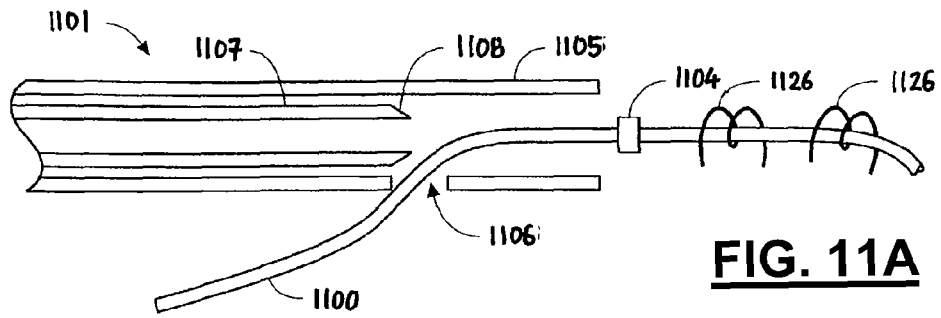
FIGS. 11A-11F illustrate various examples of devices that may be used to cut a tether.

A variety of different suitable cutting elements and devices may be used to cut a tether. As an example, FIG. 11A shows a cutting device (1101) that may be used to cut a tether (1100) extending through anchors (1126). Cutting device (1101) comprises a catheter (1105) and a tubular cutter (1107) disposed within catheter (1105). As shown in FIG. 11A, tether (1100) has been fixed by a locking element (1104), and has been threaded into catheter (1105) such that it exits through a side opening (1106) in the catheter. Tether (1100) can be threaded into catheter (1105) by any suitable method including, for example, one or more of the methods described above. Tubular cutter (1107) has an edge (1108) that is sufficiently sharp to cut a tether. For example, tubular cutter (1107) may be in the form of a metal tube having a sharpened edge. During use, tubular cutter (1107), which is attached to a flexible tube or a rod, is advanced within catheter (1105) such that the tubular cutter passes over side opening (1106). As tubular cutter (1107) is advanced over tether (1100), tubular cutter (1107) shears off the excess portion of the tether. While tubular cutter (1107) is tubular in shape, other configurations of cutters may be used. For example, a cutter may be semitubular (e.g., having a shape similar to a half-pipe), or may have any other suitable configuration. In some variations, a cutter may not be tubular or semitubular. As an example, a cutter may be in the form of a flat blade.

Figure 11B:
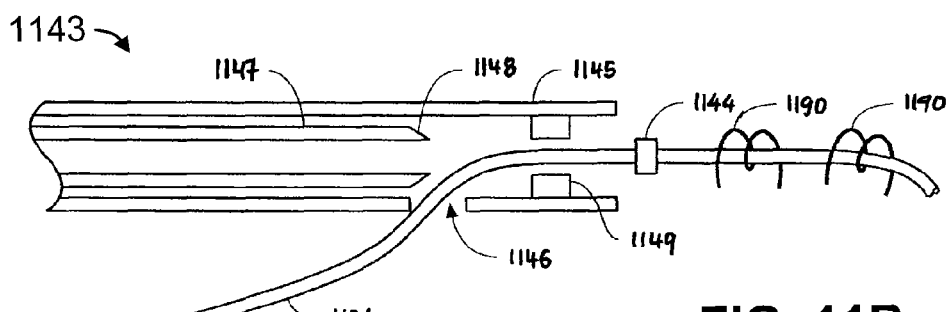

In some variations, and as shown in FIG. 11B, a cutting device (1143) comprises a catheter (1145), a base (1149) positioned on an interior surface of the catheter, and a tubular cutter (1147) concentrically disposed within the catheter. While cutter (1147) is tubular, other configurations of cutters may be used, as described above. Base (1149) can, for example, be in the form of a block that is attached to the interior surface of catheter (1145), or that is integral with the interior surface of catheter (1145). Base (1149) can be formed of any suitable material, such as any elastomeric or rigid material. FIG. 11B shows cutting device (1143) being used to cut a tether (1134) extending through anchors (1190), into catheter (1145), and through a side opening (1146) in catheter (1145). Prior to being cut, tether (1134) is fixed in place by a locking element (1144). Then, tubular cutter (1147) is advanced to cut tether (1134). Tubular cutter (1147) is advanced against base (1149), which assists tubular cutter (1147) in cutting tether (1134). In some variations, tubular cutter (1147) can be spun or rotated to improve cutting.

Figure 11C:
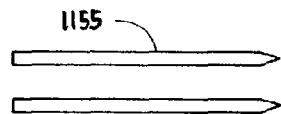
Figure 11D:
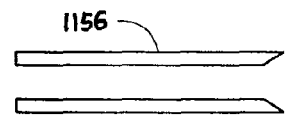
Figure 11E:
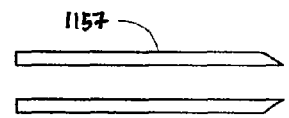

Tubular cutters can have any suitable cutting edge configuration. For example, a tubular cutter may have a beveled cutting edge, as exemplified by tubular cutter (1155) of FIG. 11C, a sharpened outer cutting edge, as exemplified by tubular cutter (1156) of FIG. 11D, or a sharpened inner cutting edge, as exemplified by tubular cutter (1157) of FIG. 11E. In addition, a tubular cutter may have a serrated or saw-tooth pattern of sharp protrusions around its perimeter to aid in cutting. Such variations may be used, for example, when the tubular cutter is spun or rotated during the cutting process.

Figure 11F:
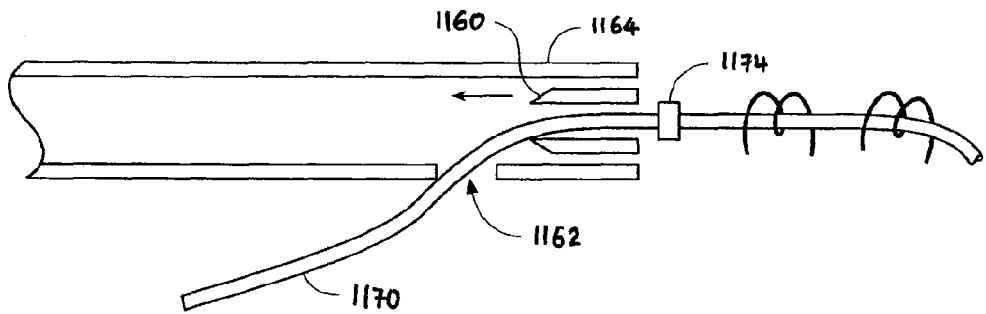

In some variations, and as shown in FIG. 11F, a tubular cutter (1160) can be positioned in front of a side opening (1162) in a catheter (1164). Tubular cutter (1160) can then be pulled in a proximal direction toward side opening (1162) (indicated by solid arrow) to cut a tether (1170) extending through side opening (1162), which has been fixed by a locking element (1174). Pulling a cutter proximally may provide for a relatively easy and/or efficient way of cutting a tether.

Figure 12:
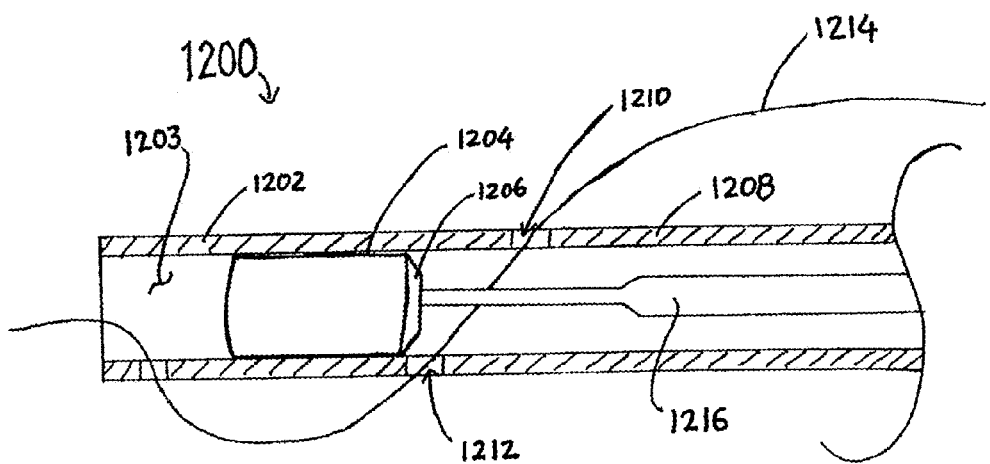
FIG. 12 is a side view in partial cross-section of a variation of a device that may be used to cut a tether.

FIG. 12 shows another variation of a cutting device. As shown there, a cutting device (1200) comprises a tubular elongated member (1202) having a lumen (1203), and a cutter (1204) disposed within the lumen of the elongated member. Cutter (1204) has a cutting blade (1206) that faces in a proximal direction. Elongated member (1202) comprises a side wall (1208) having two openings (1210) and (1212) through which a tether (1214) is threaded, such that the tether crosses the lumen of the elongated member. While two side wall openings are shown, other variations of devices may include a different number of side wall openings, such as three or four side wall openings. When it is desired to sever tether (1214), cutter (1204) is pulled proximally using a pulling member (1216) that is attached to cutter (1204). This causes cutting blade (1206) to contact and sever tether (1214). While cutter (1204) is pulled proximally using pulling member (1216), in some variations, a cutter disposed within the lumen of an elongated member may alternatively or additionally be pushed in a proximal direction. For example, a pushing member may be placed into the elongated member at its distal end, and used to push the cutter toward the proximal end of the elongated member.

While cutting devices comprising catheters and cutters that are located internally of their catheters have been shown, some variations of cutting devices may include a catheter and one or more cutters that are located externally of the catheter. Such variations of cutting devices may or may not additionally include one or more cutters that are located internally of the catheter.

A tether cutter may comprise any appropriate structure or material. Moreover, in addition to the tubular cutters described above, other examples of tether cutters include tether cutters that cut by heat, electricity, chemical reaction, or the like. For example, in some variations, a tether cutter may comprise an electrode or filament through which electrical energy is applied to cut a tether.

Figure 13A:
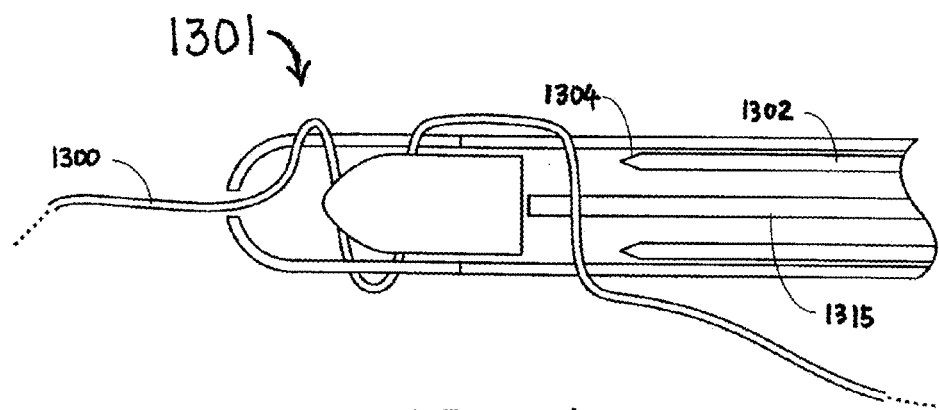
FIGS. 13A and 13B show different variations of devices that may be used to lock and cut a tether.
Figure 13B:
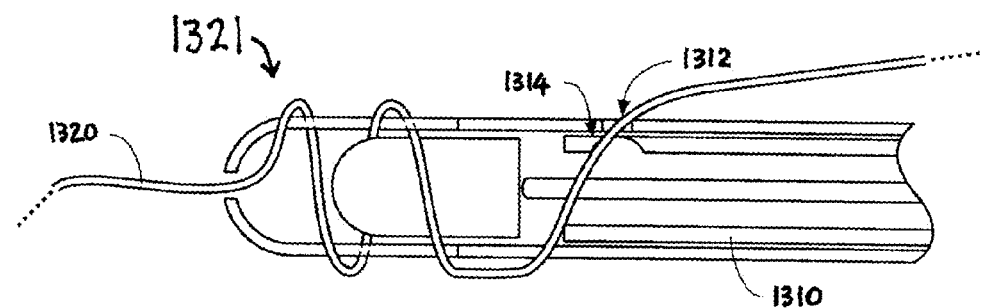

While locking devices and cutting devices have been described, in some variations, a single device can provide both locking and cutting functions. As an example, in some variations, a tether tensioning device may comprise both a tether-locking element and a tether-cutting element. FIGS. 13A and 13B illustrate different examples of tether cutters that may be incorporated into a device that also includes a locking element.

FIG. 13A shows a device (1301) that is in the form of a catheter and that comprises a detachable locking element. The device also includes a tubular tether cutter (1302) having a sharpened outer edge (1304), and a pushing member (1315) that passes through cutter (1302). Device (1301) further includes guides which can guide a tether (1300) through the device and position the tether for cutting. As shown in FIG. 13A, tether (1300) is positioned through the device so that it can be readily cut by cutter (1302) when the cutter is brought forward (e.g., moving the cutter distally). In FIG. 13A, cutter (1302) has at least one edge (e.g., over half of the cutter's circumference) so that at least one end of the tether (e.g., the end contacting the more proximal end of the tether) is cut by the cutter.

As described above, other types of tether cutters may be used as well. For example, FIG. 13B shows a device (1321) comprising a similar tubular tether cutter (1310) that is configured to cut the tether when the cutter is retracted proximally. In FIG. 13B, cutter (1310) has a passage (1312) through which a tether (1320) passes, and where at least a portion (1314) of the cutter is sharp. Tether (1320) also passes through the wall of the device (configured as a catheter in FIG. 13B, although other suitable configurations may be used). The end of the tether can be cut by drawing the tether taut after securing the locking element of the device and then moving the cutter against the tether so that it is cut.

Additional variations of devices that serve both a tether-locking function and a tether-cutting function may be used. For example, in certain variations, a device may comprise a tether cutter that is configured to cut a tether when the cutter is pulled proximally (e.g., like cutter (1204) in FIG. 12 above), as well as a locking element comprising an interlocking feature, such as interlocking feature (812) (shown in, and described with reference to, FIGS. 8A-8C). Other suitable combinations of locking and cutting elements may also be used, as appropriate.

While tensioning devices comprising locking and/or cutting elements have been described above, in some variations, separate tensioning devices and locking and/or cutting devices may be employed. Moreover, in certain variations, a tensioning device may serve one or more other functions. As an example, a tensioning device may be used to deliver one or more therapeutic agents to a target site.

While certain variations of tensioning, locking, and cutting devices and methods have been described above, other variations may be used. As an example, in some variations, a cutting device may be used to cut a tether that is not under tension. In such variations, the tether may be cut, for example, by forcing the tether against a wall of the cutting device and using the wall as a backing for cutting the tether. Locking, cutting, and tensioning devices are described, for example, in U.S. Patent Application Publication Nos. US 2006/0190030 A1, US 2006/0122633 A1, and US 2008/0172035 A1, all of which were previously incorporated by reference in their entirety.

EXAMPLES

The following examples describe the use of anchors and tensioning devices for treating a cardiac valve tissue. These examples are only intended to illustrate one possible use of the anchors, tensioning devices, and related methods, and should not be considered limiting.

In some variations, one or more of the devices described here may be used for treatment of a cardiac valve dysfunction. For example, one or more anchor delivery devices may be positioned at a target site in tissue in the vicinity of a valve annulus using a guide tunnel, a plurality of slidably coupled anchors may be delivered from the delivery device(s), and the anchors may be drawn together to tighten a valve annulus. The devices used for anchor delivery may include an elongate catheter with a housing at or near the distal end for releasably housing one or more anchors, as well as guide devices for facilitating advancement and/or positioning of an anchor delivery device. The devices may be positioned such that the housing abuts or is close to valve annular tissue, such as the region within the upper left ventricle bound by the left ventricular wall, a mitral valve leaflet and chordae tendineae. Self-securing anchors having any of a number of different configurations may be used in certain variations. After the tethered anchors have been delivered to a target tissue, the tether may be tensioned, locked, and/or cut using any of the devices described here or any other suitable devices.

Figure 14:
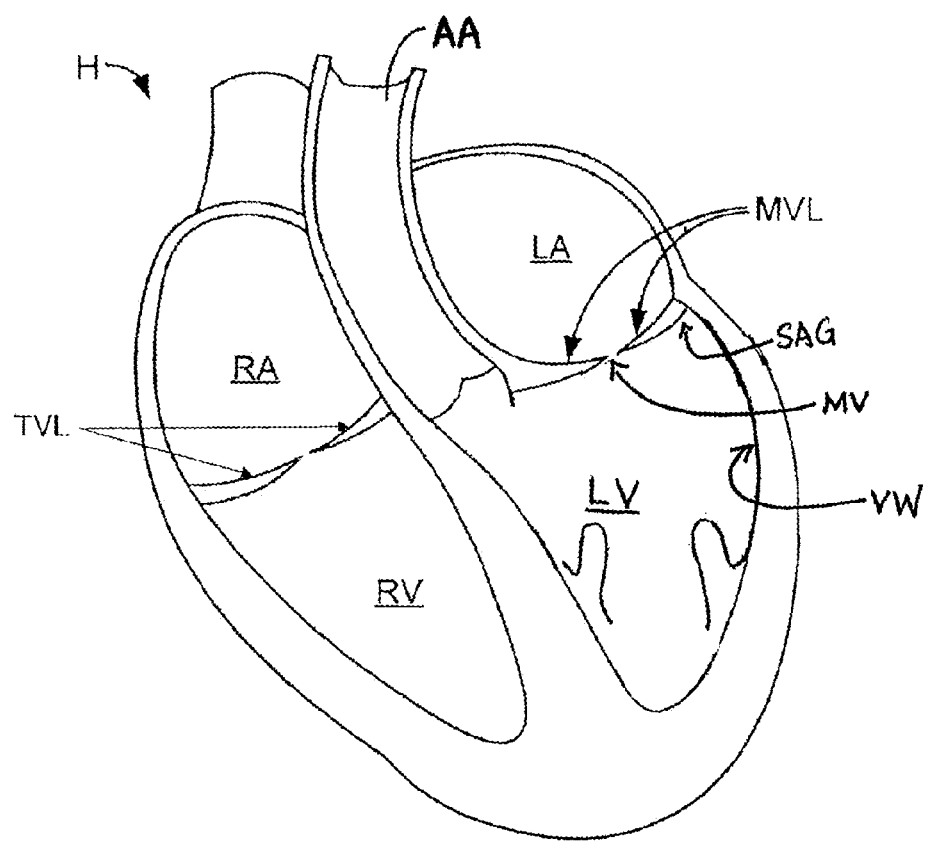
FIG. 14 is a schematic view of a heart.

For example, FIG. 14 is a schematic diagram illustrating the chambers of the heart (H), including the right atrium (RA), left atrium (LA), right ventricle (RV), and left ventricle (LV). The mitral valve (MV) is the valve between left atrium (LA) and left ventricle (LV), and includes mitral valve leaflets (MVL). The subannular groove region (SAG), as used herein, includes the space bordered by the inner surface of the left ventricular wall, the inferior surface of valve leaflets (MVL), and third order chordae tendineae connected directly to the ventricular wall (VW) and valve leaflets (MVL). Blood exits the heart through the aorta (AA).

Figure 15A:
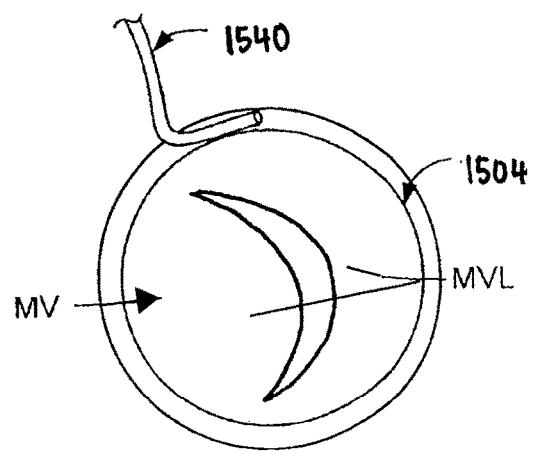
FIGS. 15A-15I schematically depict a variation of a method for delivering multiple tissue anchors to tissue in the vicinity of a heart valve.
Figure 15B:
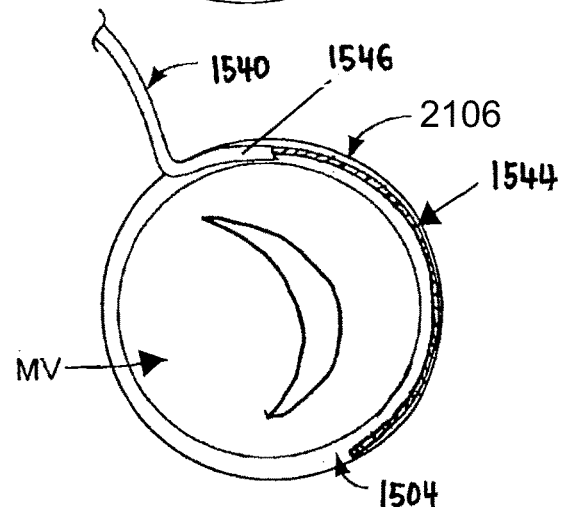

FIGS. 15A-15I depict a variation of a method for repairing a malfunctioning mitral valve. As shown there, mitral valve (MV) is depicted schematically from an inferior perspective looking in a superior direction. It should be noted that in other variations of methods, the tricuspid valve, pulmonary valve or aortic valve may alternatively or additionally be accessed. Referring to FIG. 15A, a guide catheter (1540) may be advanced to a subannular groove region (1504) using any suitable access route, such as one the access routes described, for example, in U.S. Patent Application Publication No. US 2009/0222083 A1, which is hereby incorporated by reference in its entirety. Guide catheters are described, for example, in U.S. Provisional Application No. 61/145,964, filed on Jan. 20, 2009; No. 61/160,670, filed on Mar. 16, 2009; and No. 61/178,938, filed on May 15, 2009, all of which are hereby incorporated by reference in their entirety. As shown in FIG. 15B, after guide catheter (1540) has been positioned at the desired location in subannular groove region (1504), a guidewire (1544) is advanced through the lumen of guide catheter (1540). Guidewire (1544) may be advanced beyond the distal end (1546) of guide catheter (1540), so that guidewire (1544) extends further along subannular groove region (1504) than guide catheter (1540), as shown in FIG. 15B.

Figure 15C:
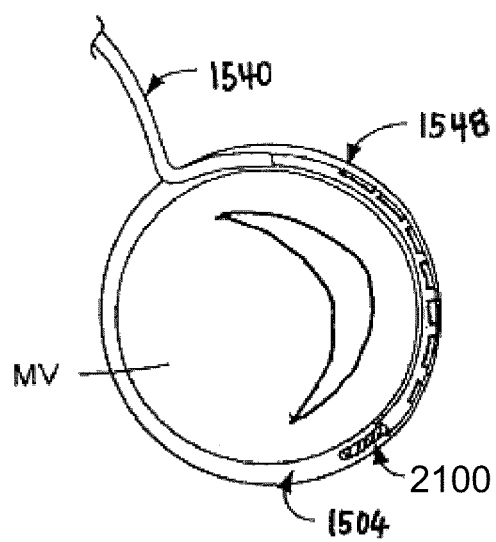

After guidewire (1544) has been positioned in the subannular groove region (1504), a guide tunnel or tunnel catheter (1548) is advanced through guide catheter (1540), over guidewire (1544), as shown in FIG. 15C. Tunnel catheter (1548) may be any suitable catheter, and in some instances, it is desirable that the tunnel catheter be pre-shaped or pre-formed at its distal end, such as the tunnel catheter illustrated in FIG. 15C. In some variations, tunnel catheter (1548) may have a pre-shaped distal portion that is curved. In this way, the tunnel catheter may more easily conform to the geometry of the atrio-ventricular valve. It should also be understood that any of the catheters or guidewires described here may be pre-shaped or pre-formed to include any number of suitable curves, angles or configurations. Of course, the guidewires and/or catheters described here may also be steerable. Catheters, such as tunnel catheters, are described, for example, in U.S. Patent Application Publication No. US 2009/0222083 A1, which was previously incorporated by reference in its entirety.

Figure 15D:
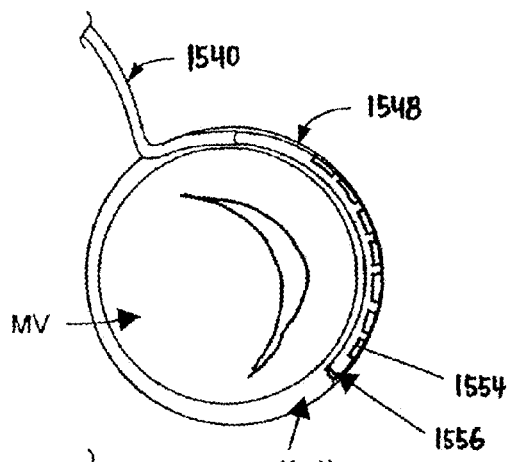

After tunnel catheter (1548) has been positioned in the subannular groove region (1504), guidewire (1544) may be withdrawn proximally, as shown in FIG. 15D. A delivery catheter (not shown) may then be advanced through the lumen of tunnel catheter (1548) and toward opening (1554) at or adjacent to the distal tip (1556) of tunnel catheter (1548). In the variation depicted in FIG. 15E, the delivery catheter remains within tunnel catheter (1548), and an anchor (1558) is deployed through opening (1554) to attach to the body tissue. In other variations, however, the delivery catheter may be extended through opening (1554) of tunnel catheter (1548). Exemplary variations of delivery catheters are described, for example, in U.S. Patent Application Publication No. US 2009/0222083 A1, which was previously incorporated by reference in its entirety, and in U.S. Provisional Application No. 61/160,230, filed on Mar. 13, 2009, and No. 61/178,910, filed on May 15, 2009, both of which are hereby incorporated by reference in their entirety.

In some variations, opening (1554) is the distalmost anchor delivery opening of tunnel catheter (1548), but in certain variations, one or more openings may have a separate lumen in tunnel catheter (1548), so that any anchors deployed from such openings would not interfere with, or restrict the deployment of, subsequent tissue anchors distal to those openings. Furthermore, although FIG. 15E depicts opening (1554) as a side opening of tunnel catheter (1548), in some variations, opening (1554) may be located at the distal tip (1556) and may be the same opening shown with a distally protruding guidewire (1544) in FIG. 15C.

Figure 15E:
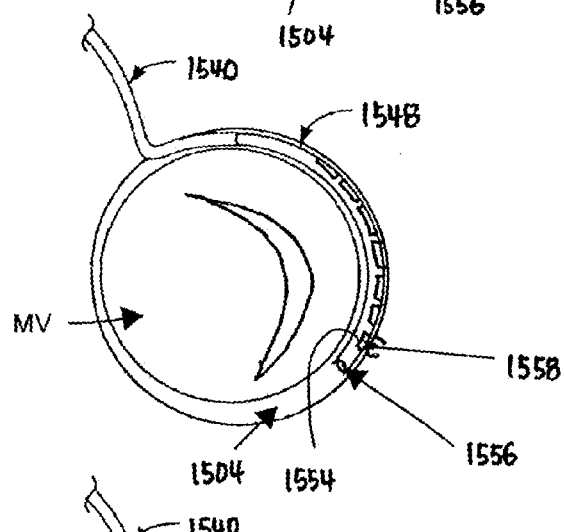

Anchor (1558), shown in FIG. 15E, is preferably a self-expanding design as it exits the delivery catheter and tunnel catheter (1548) to self-secure into the annular tissue accessible from subannular groove region (1504). It should be understood that one or more anchors of an implant may be deployed into the annulus directly, while other anchors may be secured to other tissue in the vicinity of the subannular groove region (1504). For example, one or more anchors may be secured to the tissue below the annulus. After anchor (1558) has been deployed, the delivery catheter may be proximally withdrawn. A tether (1560), attached to anchor (1558) and seen best in FIGS. 15G and 15H, may be used to facilitate the insertion of additional delivery catheters toward the implantation site.

Figure 15F:
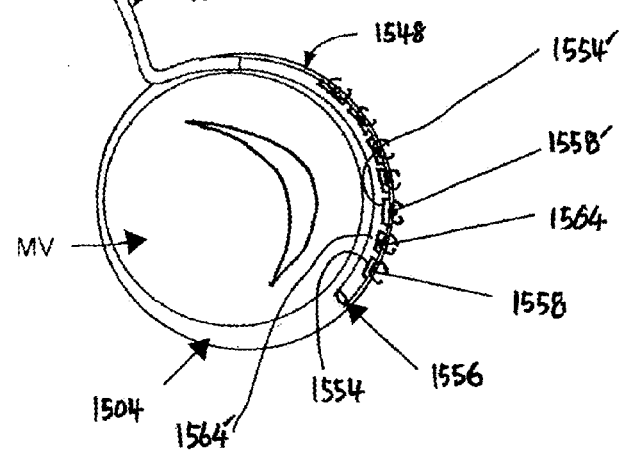
Figure 15G:
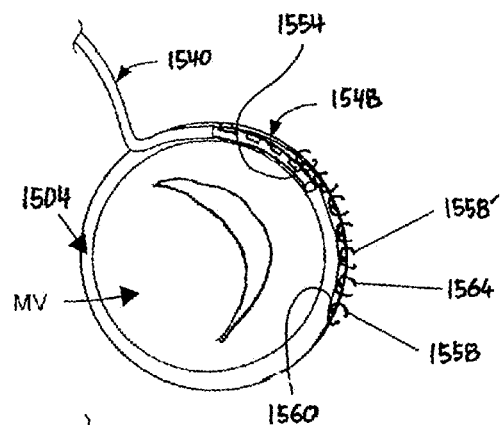
Figure 15H:
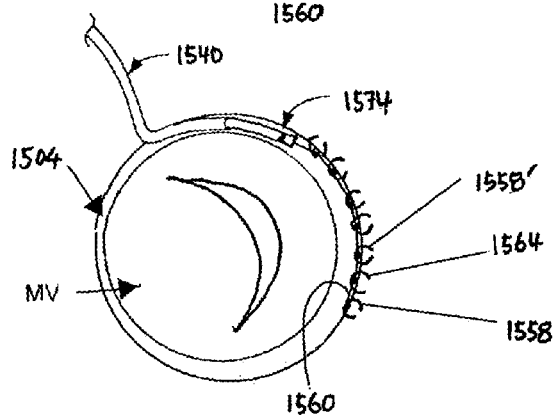
Figure 15I:
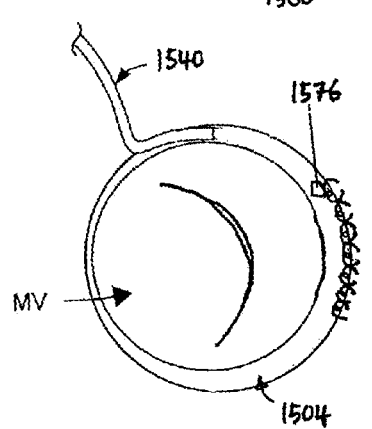

In this particular method variation, as demonstrated in FIG. 15F, tunnel catheter (1548) is maintained in the same position while additional anchors (1564) and (1558') are deployed from additional openings (1564') and (1554') along tunnel catheter (1548). In some variations, one or more delivery catheters may be serially inserted into tunnel catheter (1548) using tether (1560) to serially guide anchors (1564) and (1558') through openings (1564') and (1554'). In certain variations, the delivery catheters may be loaded with one or more anchors at the point-of-use, while in other variations the delivery catheters may be pre-loaded at the point-of-manufacture. The delivery catheters may also be reloaded at the point-of-use, or may be single-use devices that are discarded after anchor deployment. In some variations, the delivery catheters may be configured to hold two or more anchors (1558), (1558') and (1564) and can deliver multiple anchors without requiring withdrawal of the delivery catheter between anchor deployments. Still other multi-anchor delivery catheters may be configured to deliver multiple anchors simultaneously through multiple openings of tunnel catheter (1548). Anchors (1558), (1558') and (1564) may be deployed from the delivery catheter and tunnel catheter (1548) in any suitable fashion, including but not limited to using a push-pull wire, a plunger, and/or any other suitable actuation technique. Similarly, anchors (1558), (1558') and (1564) may be coupled to tether (1560) by any suitable attachment method. For example, one or more knots, welded regions, and/or adhesives may be used. Alternate variations for anchor deployment and anchor attachments are described, for example, in U.S. Patent Application Publication No. US 2008/0172035 A1, which was previously incorporated by reference in its entirety, and in U.S. patent application Ser. No. 12/505,332, filed on Jul. 17, 2009, which is hereby incorporated by reference in its entirety.

After anchor deployment and positioning, the reshaping of cardiac tissue may be achieved by tensioning the tether to cause a cinching effect that brings the tissue closer together. In some variations, the anchor deployment device may be removed, and the tether may be threaded into a tether tensioning device (e.g., using a loading tool, such as one of the loading tools described above) comprising a locking element and/or cutting element. For example, the loading tool may be used to thread the tether through the locking element and/or cutting element. Thereafter, the tether may be coupled to one or more tensioning components of the tether tensioning device. For example, the tether may be coupled to a rotatable tensioning member of the tether tensioning device. After the tether has coupled to the tensioning component or components, tension may be applied to the tether by retracting the tether proximally. In one variation, this may be achieved by winding the tether around a bobbin, and rotating the bobbin to provide the desired tension. Optionally, the tether may be tensioned manually, or by winding the tether around a screw (e.g., on a tether tensioning device), and rotating the screw. In certain variations, tether tension may be increased and decreased to achieve the desired amount of tissue cinching. As described above, to limit the likelihood of over-tensioning a tether (and, e.g., potentially damaging tissue, such as cardiac tissue) certain variations of tether tensioning devices may comprise one or more mechanisms that prevent a tether from being tensioned beyond a pre-determined threshold.

In some instances, the effect of tether tensioning upon tissue may be measured or otherwise evaluated using physiological and/or imaging feedback. In certain variations, the level of desired tissue cinching may be determined by one or more imaging techniques, such as X-ray fluoroscopy, ultrasound, Echo Doppler, etc. In some variations, in the treatment of mitral regurgitation, an echocardiologist may monitor the effect of tether-tensioning on the amount of regurgitation using transesophageal or transthoracic echo. The transesophageal or transthoracic echo may provide feedback as to the minimization of leakage.

Figure 16:
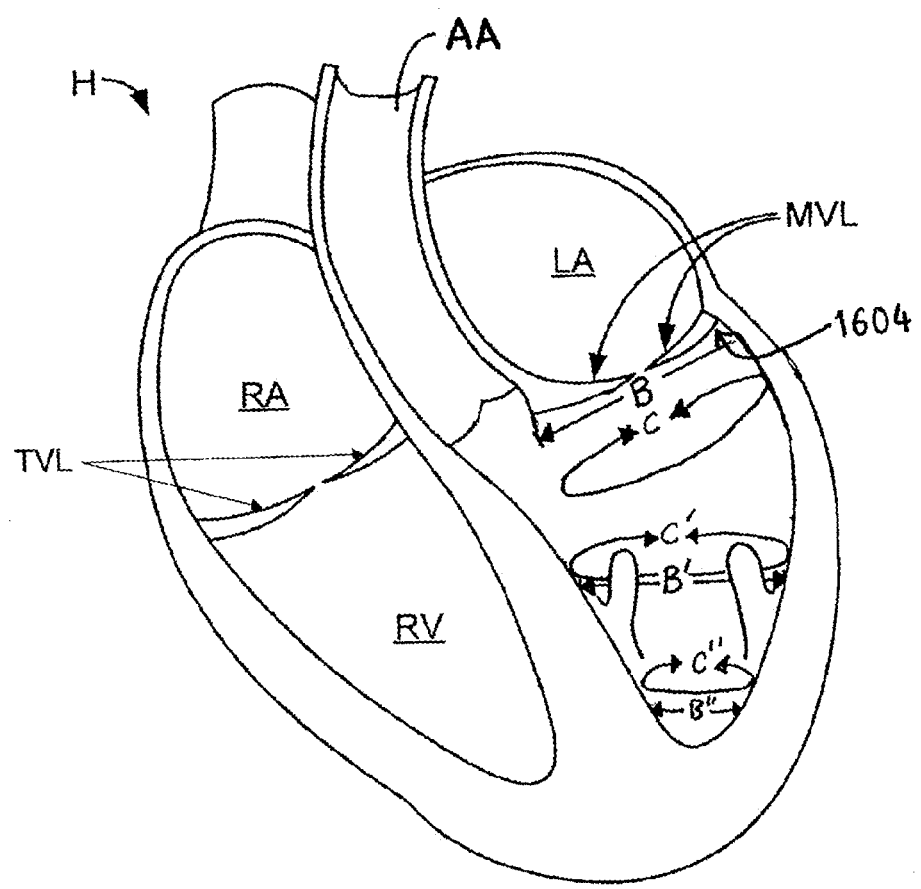
FIG. 16 is a schematic view of a heart illustrating various dimensions of a chamber of the heart.

In some variations, the reshaping of a ventricle may be performed using a multi-opening guide tunnel with a releasable tether retaining mechanism, along any of a variety of dimensions or vectors. For example, referring to FIG. 16, in certain variations, the reshaping of a ventricle or a valve may occur with respect to the diameter (B) or the circumference (C) about a valve orifice. For example, diameter (B) and circumference (C) may be reshaped with respect to subannular groove region (1604). In addition to the reshaping of valvular structures, reshaping can also be performed with respect to the non-valvular structures of a heart chamber. For example, one or more of the diameters or circumferences of a heart ventricle may be reshaped. As shown in FIG. 16, the diameter (B') and the circumference (C') of the ventricle located generally at or above the papillary muscles may be reshaped. The diameter (B") and circumference (C") of the ventricle at or below the papillary muscles may also be reshaped. The orientation of the diameter and circumference that is reshaped or assessed can vary, but in some variations, the diameter or circumference may be in a generally perpendicular orientation with respect to a longitudinal axis of a ventricle. One of skill in the art will understand that the longitudinal axis may be characterized in a number of ways, including but not limited to a longitudinal axis from a valve orifice to an apex of a heart chamber, or from the apex of a heart chamber to a point that generally splits the ventricular volume in half. Similarly, some of the implantation dimensions or vectors may also be oriented with respect to the anterior-posterior axis or the septo-lateral axis of the heart chamber.

Figure 17:
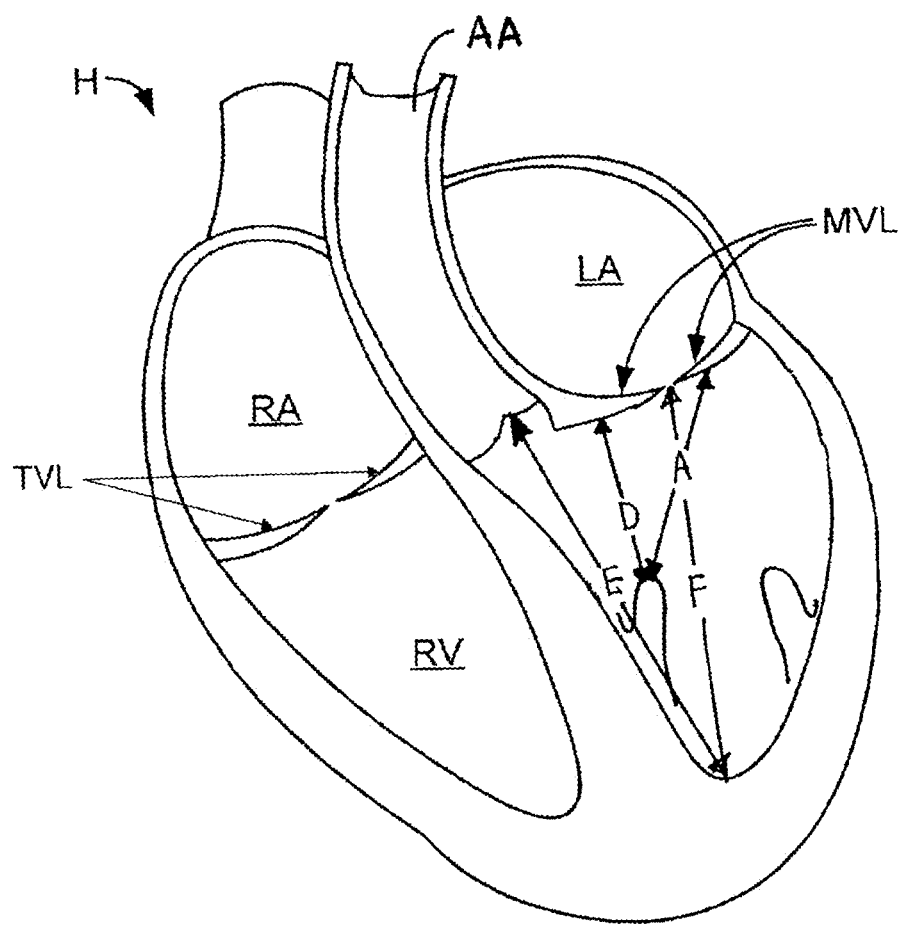
FIG. 17 is another schematic view of a heart illustrating various dimensions of a chamber of the heart.

Referring to FIG. 17, in some variations, the myocardium along vectors (A) and (D) between a papillary muscle and a valve leaflet may be reshaped. Vectors (D) or (A) may be between a papillary muscle and its associated valve leaflet, or between a papillary muscle and an unassociated valve leaflet, respectively. Although vectors (A) and (D) depicted in FIG. 17 are shown from the tip of the papillary muscle, these pathways may also be assessed from the base of the papillary muscle. Similarly, myocardial pathways including a valve leaflet may be assessed from the distalmost section, the middle or the base of the valve leaflet. In certain variations, the reshaping of the heart may occur between the apex of a heart chamber and one or more valves. For example, reshaping may occur along the vector (E) between the outlet valve and the apex of a heart chamber, and/or along the pathway (F) between the inlet valve and the apex. Cardiac valve repair methods are further described, for example, in U.S. Patent Application Publication No. US 2009/0222083 A1, which was previously incorporated by reference in its entirety.

Kits are also described here. In some variations, the kits may include at least one tether tensioning device and at least one tether-locking device and/or tether-cutting device. In certain variations, the kit may include at least one tether-cutting device and at least one tether tensioning device that also has tether-locking capabilities, or may include at least one tether-locking device and at least one tether tensioning device that also has tether-cutting capabilities. In some variations, a kit may include multiple (e.g., 2, 3, 4, 5) different tether tensioning devices, such as tether tensioning devices having different maximum tether tensioning thresholds. In certain variations, a kit may include one or more anchor delivery devices. Of course, instructions for use may also be provided with the kits.

While methods, devices, and kits have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A device for tensioning a tether comprising:
   a handle portion comprising:
      a housing;
      a rotatable tensioning member comprising a tensioning wheel having detents and a bobbin having bearings, wherein the bobbin is external to the housing and the tensioning wheel detents and the bobbin bearings are configured to engage each other; and
      a gear connecting the tensioning wheel and the bobbin to the housing,
      wherein the rotatable tensioning member is configured to engage a tether and to rotate in a first direction to increase the tension of the tether and in a second direction to decrease the tension of the tether, and wherein the rotatable tensioning member further comprises a lock-out mechanism that provides for a maximum amount of tensioning of a tether engaged by the rotatable tensioning member.

2. The device of claim 1, wherein the rotatable tensioning member further comprises at least one compression spring that is in contact with the bobbin and that exerts a force on the bobbin that biases the bobbin toward the tensioning wheel and determines the rotatability of the bobbin.

3. The device of claim 2, wherein the tensioning wheel is configured to disengage from the bobbin when the tension of a tether engaged by the rotatable tensioning member reaches a predetermined value.

4. The device of claim 3, wherein the bobbin comprises a body defining a notch sized and shaped to engage a tether.

5. The device of claim 3, wherein the at least one compression spring has a spring constant of at least about 10 lb/inch.

6. The device of claim 5, wherein the at least one compression spring has a spring constant of at most about 30 lb/inch.

7. The device of claim 3, further comprising an elongated member coupled to a distal portion of the housing of the handle portion.

8. The device of claim 7, wherein the elongated member comprises a catheter.

9. The device of claim 7, further comprising a locking element coupled to a distal portion of the elongated member, wherein the locking element is configured to secure a tether.

10. The device of claim 9, further comprising a tether cutter.

11. The device of claim 9, wherein the locking element is releasably coupled to the distal portion of the elongated member.

12. The device of claim 9, wherein the locking element comprises a plug and a locking member configured to receive the plug.

13. The device of claim 12, wherein the plug is compressible.

14. The device of claim 12, wherein the locking member comprises a lumen configured to receive the plug, and wherein the plug is rotatable when at least partially disposed within the lumen.

15. The device of claim 12, further comprising a pushing member.

16. The device of claim 15, wherein the pushing member is translatable toward the plug to push the plug into a lumen of the locking member.

17. The device of claim 3, further comprising a tether cutter.

18. The device of claim 3, wherein the gear is configured to rotate the rotatable tensioning member.

19. The device of claim 18, further comprising a lever configured to activate the rotatable tensioning member to rotate in either the first direction or the second direction.

20. The device of claim 19, wherein the lever has a first position in which the lever engages the gear, and a second position in which the lever releases the gear.

21. The device of claim 20, wherein when the lever is in the first position, it maintains the tension of a tether engaged by the rotatable tensioning member in a static state.

22. The device of claim 3, further comprising a lever configured to activate the rotatable tensioning member to rotate in either the first direction or the second direction.

23. A kit comprising:
a first device for tensioning a tether as recited in claim 1; and
an anchor delivery device.

24. The kit of claim 23, wherein the rotatable tensioning member of the first device further comprises at least one compression spring that is in contact with the bobbin and that exerts a force on the bobbin that biases the bobbin toward the tensioning wheel and determines the rotatability of the bobbin.

25. The device of claim 24, wherein the tensioning wheel is configured to disengage from the bobbin when the tension of a tether engaged by the rotatable tensioning member reaches a predetermined value.

26. The kit of claim 25, further comprising a second device for tensioning a tether.

27. The kit of claim 26, wherein the first tether tensioning device has a first maximum tether tensioning threshold, and the second tether tensioning device has a second maximum tether tensioning threshold.

28. The kit of claim 25, further comprising a tether locking device.

29. The kit of claim 28, further comprising a tether cutting device.

30. The kit of claim 25, further comprising a tether cutting device.

* * * * *